United States Patent
Brown et al.

(10) Patent No.: US 10,065,943 B2
(45) Date of Patent: Sep. 4, 2018

(54) PYRROLIDINE DERIVATIVES AS ANGIOTENSIN II TYPE 2 ANTAGONISTS

(71) Applicant: NOVARTIS AG, Basel (CH)

(72) Inventors: Jane Brown, Bingham (GB); Thomas David McCarthy, Westport, CT (US); Alan Naylor, Royston (GB); John Paul Watts, Southwell (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/542,071

(22) PCT Filed: Jan. 12, 2016

(86) PCT No.: PCT/IB2016/050122
§ 371 (c)(1),
(2) Date: Jul. 6, 2017

(87) PCT Pub. No.: WO2016/113668
PCT Pub. Date: Jul. 21, 2016

(65) Prior Publication Data
US 2017/0369473 A1   Dec. 28, 2017

(30) Foreign Application Priority Data

Jan. 13, 2015 (AU) ................................ 2015900077
Jul. 23, 2015 (AU) ................................ 2015902922

(51) Int. Cl.
| | | |
|---|---|---|
| *C07D 403/04* | (2006.01) | |
| *C07D 413/04* | (2006.01) | |
| *C07D 495/04* | (2006.01) | |
| *C07D 471/04* | (2006.01) | |
| *C07D 401/04* | (2006.01) | |
| *C07D 417/04* | (2006.01) | |

(52) U.S. Cl.
CPC ......... *C07D 403/04* (2013.01); *C07D 401/04* (2013.01); *C07D 413/04* (2013.01); *C07D 417/04* (2013.01); *C07D 471/04* (2013.01); *C07D 495/04* (2013.01)

(58) Field of Classification Search
CPC .. C07D 403/04; C07D 413/04; C07D 495/04; C07D 471/04; C07D 417/04; C07D 401/04
See application file for complete search history.

(56) References Cited

U.S. PATENT DOCUMENTS

| 5,789,434 A | 8/1998 | Kluender et al. |
|---|---|---|
| 2018/0057477 A1 | 3/2018 | Brown et al. |

FOREIGN PATENT DOCUMENTS

| AU | 2013202982 | | 11/2013 | |
|---|---|---|---|---|
| WO | 2010/017401 A1 | | 11/2010 | |
| WO | WO 2013/102242 | * | 7/2013 | ........... C07D 207/16 |
| WO | 2016/142867 A1 | | 9/2016 | |

* cited by examiner

*Primary Examiner* — Erich A Leeser
(74) *Attorney, Agent, or Firm* — Laura K. Madden

(57) ABSTRACT

The invention relates to heterocyclic angiotensin II type 2 (AT$_2$) receptor antagonists of formula (I), and pharmaceutically acceptable salts thereof, ((I) in which all of the variables are as defined in the specification, pharmaceutical compositions thereof, combinations thereof, and their use as medicaments, particularly for the treatment of neuropathic or inflammatory pain.

(I)

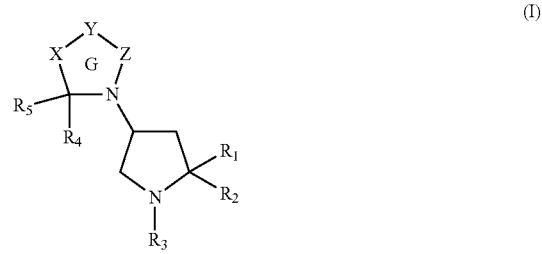

21 Claims, No Drawings

PYRROLIDINE DERIVATIVES AS ANGIOTENSIN II TYPE 2 ANTAGONISTS

This application is a U.S. national Phase filing of International Serial No. PCT/IB2016/050122 filed Jan. 12, 2016, and claims priority to Australian provisional application No. 2015900077 filed Jan. 13, 2015, and Australian provisional application No. 2015902922 filed Jul. 23, 2015, the contents of which are incorporated herein by reference in their entirety.

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although the $AT_2$ receptor has been known since the 1980s, much less is known about its biological function than the angiotensin II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain, particularly inflammatory pain [WO 2007/106938] and neuropathic pain [WO 2006/066361], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohumeral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells. Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

Heterocyclic $AT_2$ receptor antagonists are known to have activity in treatment of neuropathic pain, inflammatory pain, impaired nerve conduction velocity, cell proliferative disorders, conditions associated with conditions characterized by neuronal hypersensitivity, disorders associated with an imbalance between bone resorption and bone formation and disorders associated with aberrant nerve regeneration (WO 2013/102242, WO 2013/110134 and WO 2013/110135).

However, the present invention is predicated in part on the discovery of new heterocyclic compounds that have improved $AT_2$ receptor antagonist activity.

SUMMARY OF THE INVENTION

In a first aspect of the present invention there is provided a compound of formula (I):

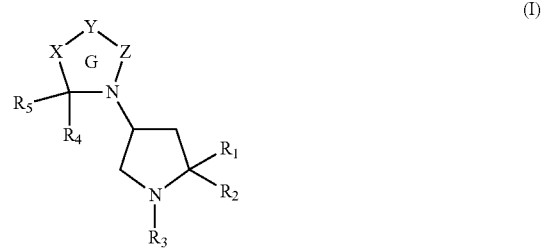

wherein Ring G is a 5 to 8 membered ring and

X is absent or is selected from —$(CR_6R_7)_n$—, —W—, —$(CR_6R_7)_m$—W—, —W—$(CR_6R_7)_m$— and —$(CR_6R_7)_p$—W—$(CR_6R_7)_p$—;

Y is —$CR_8CR_9$— wherein $R_8$ and $R_9$ together with the carbon atoms to which they are attached form an optionally substituted aromatic or heteroaromatic ring or optionally substituted aromatic or heteroaromatic ring system;

Z is absent or is selected from —$CR_4R_5$—, —$CR_6R_7CR_4R_5$— and —W—$(CR_4R_5)$—;

W is selected from —O—, —S—, —S(O)—, —$S(O)_2$—, —C(O)—, —$NR_{10}$—, —$C(O)N(R_{11})$—, —$N(R_{11})C(O)$—, —C(O)O—, —OC(O)—, —$S(O)_2N(R_{11})$—, —$N(R_{11})S(O)_2$—, —$N(R_{11})C(O)N(R_{11})$— and —$N(R_{11})S(O)_2N(R_{11})$—;

$R_1$ is selected from —$CO_2H$, —$CH_2CO_2H$, —C(O)C(O)OH, —$CH_2OH$, —$C(O)NH_2$, —CN, —$CH_2C(O)NH_2$, —$CH_2CN$, a carboxylic acid bioisostere and —$CH_2$carboxylic acid bioisostere;

$R_2$ is selected from hydrogen, alkyl, alkenyl, alkynyl, —$C_{1-6}$alkyl$R_{12}$, —$C_{2-6}$alkenyl$R_{12}$ and —$C_{2-6}$alkynyl$R_{12}$;

$R_3$ is selected from —C(O)CH(aryl)(aryl) and —C(O)N(aryl)(aryl);

Each $R_4$ and $R_5$ are independently selected from hydrogen, alkyl, alkenyl, alkynyl, —OC($R_{14}$)$_3$, —CN, —NO$_2$, —N($R_{13}$)$_2$, —CO$_2R_{13}$, —C(O)$R_{13}$, —C(O)N($R_{13}$)$_2$, —S(O)$_2R_{13}$, —S(O)$_2$N($R_{13}$)$_2$, —C($R_{14}$)$_3$, cycloalkyl, cycloalkenyl, aryl, heterocyclyl and heteroaryl, or $R_4$ and $R_5$ taken together from a carbonyl group;

$R_6$ and $R_7$ are independently selected from hydrogen, alkyl, alkenyl, alkynyl, —OR$_{13}$, —SR$_{13}$, halo, —CN, —NO$_2$, —N($R_{13}$)$_2$, —CO$_2R_{13}$, —C(O)$R_{13}$, —C(O)N($R_{13}$)$_2$, —S(O)$_2R_{13}$, —S(O)$_2$N($R_{13}$)$_2$, —C($R_{14}$)$_3$, —OC($R_{14}$)$_3$, cycloalkyl, cycloalkenyl, aryl, heterocyclyl and heteroaryl, or $R_6$ and $R_7$ taken together form a carbonyl group;

$R_{10}$ is selected from hydrogen, alkyl, alkenyl, alkynyl, cycloalkyl, cycloalkenyl, aryl, heterocyclyl, heteroaryl, —C($R_{14}$)$_3$, —C(O)$R_{13}$, —C(O)N($R_{13}$)$_2$, —S(O)$R_{13}$, —S(O)$_2R_{13}$, —S(O)$_2$N($R_{13}$)$_2$ and —CO$_2R_{13}$;

$R_{11}$ is selected from hydrogen and alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;

m is selected from an integer from 1 to 3;

p is selected from an integer of 1 or 2;

wherein each alkyl, alkenyl, alkynyl, cycloalkyl, cycloalkenyl, aryl, heterocyclyl and heteroaryl may be optionally substituted; or a pharmaceutically acceptable salt thereof.

In another aspect, the present invention provides a pharmaceutical composition comprising the compounds of formula (I) or a pharmaceutically acceptable salt thereof and a pharmaceutically acceptable carrier.

In a further aspect of the invention there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "AT$_2$ receptor" means an angiotensin II type 2 (AT$_2$) receptor polypeptide that can bind angiotensin II and/or one or more other ligands. The term "AT$_2$ receptor" encompasses vertebrate homologs of AT$_2$ receptor family members, including, but not limited to, mammalian, reptilian and avian homologs. Representative mammalian homologs of AT$_2$ receptor family members include, but are not limited to, murine and human homologs.

The term "antagonist" as used herein refers to a compound that decreases or inhibits the biological activity and/or function of an AT$_2$ receptor, including binding to the AT$_2$ receptor and blocking access to angiotensin II, inhibiting a gene that expresses AT$_2$ receptor, or inhibiting an expression product of that gene. By the term "selective", is meant that the compound binds to and/or inhibits AT$_2$ receptor activity to a greater extent than binding and inhibition of the AT$_1$ receptor. In some instances, selective refers to binding and/or inhibition of the AT$_2$ receptor with little or no binding at the AT$_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally considered painful. A hyperalgesia condition is one that is associated with increased pain caused by a stimulus that is normally mildly or minimally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, n-hexyl, 2-methylpentyl, 3-methylpentyl, 4-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "alkylene" refers to a divalent saturated hydrocarbon chain having 1 to 6 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

As used herein, the term "alkenylene" refers to a divalent unsaturated hydrocarbon chain having 2 to 6 carbon atoms and at least one double bond. Where appropriate, the alkenylene group may have a specified number of carbon atoms, for example, $C_{2-6}$alkenylene includes alkenylene groups having 2, 3, 4, 5 or 6 carbon atoms in a linear arrangement. The double bonds may be in either E or Z configuration. Examples of suitable alkenylene groups include, but are not limited to, —CH=CH—, —CH=CHCH$_2$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH$_2$CH=CHCH$_2$—, —CH$_2$CH$_2$CH$_2$CH=CH—, —CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$— and —CH$_2$CH$_2$CH$_2$CH$_2$CH=CH—.

As used herein, the term "alkynylene" refers to a divalent unsaturated hydrocarbon chain having 2 to 6 carbon atoms and at least one triple bond. Where appropriate, the alkynylene group may have a specified number of carbon atoms, for example, $C_{2-6}$alkynylene includes alkynylene groups having 2, 3, 4, 5 or 6 carbon atoms in a linear arrangement. Examples of suitable alkynylene groups include, but are not limited to, —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, —C≡CCH$_2$CH$_2$CH$_2$—, —CH$_2$C≡CCH$_2$CH$_2$—, —CH$_2$CH$_2$C≡CCH$_2$—, —CH$_2$CH$_2$CH$_2$C≡C—, —C≡CCH$_2$CH$_2$CH$_2$CH$_2$—, —CH$_2$C≡CCH$_2$CH$_2$CH$_2$—, —CH$_2$CH$_2$C≡CCH$_2$CH$_2$—, —CH$_2$CH$_2$CH$_2$C≡CCH$_2$— and —CH$_2$CH$_2$CH$_2$CH$_2$C≡C—.

In some embodiments, one or more "—CH$_2$—" groups in an alkylene, alkenylene or alkynylene group may be replaced by a heteroatom or a group containing a heteroatom including —O—, —S—, —NR—, —S(O)—, —S(O)$_2$—, —C(O)—, —C(O)NR— and NHC(O)—, where R is hydrogen or alkyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclopentadienyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, indenyl, fluorenyl, phenanthrenyl, biphenyl and binaphthyl.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 8 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, coumarinyl, quinoxalinyl, quinazolinyl, pyrazolyl, indolyl, isoindolyl, indolinyl, indazolyl, benzimidazolyl, 1H,3H-1-oxoisoindolyl, benzotriazolyl, furanyl, thienyl, thiophenyl, benzothienyl, benzofuranyl, benzodioxolanyl, benzodioxanyl, benzodioxinyl, quinolinyl, isoquinolinyl, oxazolyl, isoxazolyl, benzoxazolyl, benzothiazolyl, benzopyranyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, cyclopentyl[b]pyridinyl, benzodithiolyl, benzodihydrodithiolyl, benzodithanyl, naphthyridinyl, phthalazinyl, benzoxazinyl, benzoxadiazinyl and pteridinyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, cycloalkenyl, oxo (=O), —OH, —SH, $C_{1-6}$alkylO—, $C_{2-6}$alkenylO—, $C_{3-6}$cycloalkylO—, —Ocycloalkenyl, $C_{1-6}$alkylS—, $C_{2-6}$alkenylS—, $C_{3-6}$cycloalkylS—, cycloalkenylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, —CH$_2$F, —OCH$_2$F, —SCH$_2$F, -phenyl, -heterocyclyl, -heteroaryl, —Oheteroaryl, —Oheterocyclyl, —Ophenyl, —C(=O) phenyl, —C(=O)C$_{1-6}$alkyl —SO$_2$H, —SO$_2$C$_{1-6}$alkyl, —SO$_2$phenyl, —SO$_2$NH$_2$, —SO$_2$NH(C$_{1-6}$alkyl), —SO$_2$N (C$_{1-6}$alkyl)$_2$, —SO$_2$NH(phenyl), —SO$_2$N(phenyl)$_2$, —CONH$_2$, —CONH(C$_{1-6}$alkyl), —CON(C$_{1-6}$alkyl)$_2$, —CONH(phenyl) and —CON(phenyl)$_2$. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, oxo, fluoro, chloro, bromo, iodo, cyano, nitro, —CO$_2$H, —CO$_2$CH$_3$, —CONH$_2$, —SO$_2$CH$_3$, —SO$_2$phenyl, —CONH(CH$_3$), —CON(CH$_3$)$_2$, —SO$_2$NH$_2$, —SO$_2$NH (CH$_3$), —SO$_2$N(CH$_3$)$_2$, trifluoromethyl, trifluoromethoxy, trifluoromethylthio, difluoromethyl, difluoromethoxy, difluoromethylthio, fluoromethyl, fluoromethoxy, fluoromethylthio, morpholino, amino, methylamino, dimethylamino, phenyl, phenoxy, phenylcarbonyl, benzyl and acetyl.

The term "carboxylic acid bioisostere" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—PO$_3$H$_2$), —C(OH)(CF$_3$)$_2$, N-(aryl or heteroaryl)-sulfonamides, acylsulfonamides and sulfonic acid (—SO$_3$H) [See Patani and LaVoie, 1996]. Examples of sulfonamide isosteric equivalents of carboxy groups include —C(=O)NH SO$_2$R$^a$, —C(=O)NHSO$_2$N(R$^a$)$_2$, —C(=O) NHSO$_2$NH(R$^a$), —SO$_2$NHC(=O)R$^a$, —SO$_2$NHC(=O) NHR$^a$, —SO$_2$NHR$^a$ and —NHSO$_2$R$^a$, where R$^a$ is selected from the group consisting of C$_{1-6}$alkyl, C$_{2-6}$alkenyl, C$_{3-8}$cycloalkyl, aryl, heterocyclyl, heteroaryl and —CF$_3$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognized that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

Compounds of the Invention

In a first aspect of the present invention there is provided a compound of formula (I):

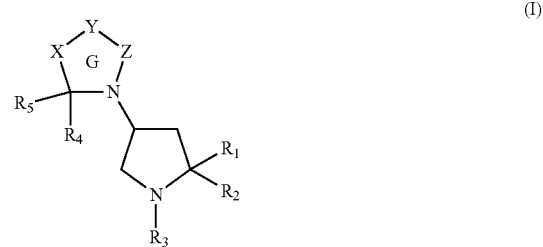

(I)

wherein Ring G is a 5 to 8 membered ring and
X is absent or is selected from —(CR$_6$R$_7$)$_m$—, —W—, —(CR$_6$R$_7$)$_m$—W—, —W—(CR$_6$R$_7$)$_m$— and —(CR$_6$R$_7$)$_p$—W—(CR$_6$R$_7$)$_p$—;

Y is —CR$_8$CR$_9$— wherein R$_8$ and R$_9$ together with the carbon atoms to which they are attached form an optionally substituted aromatic or heteroaromatic ring or optionally substituted aromatic or heteroaromatic ring system;

Z is absent or is selected from —CR$_4$R$_5$—, —CR$_6$R$_7$CR$_4$R$_5$— and —W—(CR$_4$R$_5$)—;

W is selected from —O—, —S—, —S(O)—, —S(O)$_2$—, —C(O)—, —NR$_{10}$—, —C(O)N(R$_{11}$)—, —N(R$_{11}$)C(O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;

R$_1$ is selected from —CO$_2$H, —CH$_2$CO$_2$H, —C(O)C(O) OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;

R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;

R$_3$ is selected from —C(O)CH(aryl)(aryl) and —C(O)N (aryl)(aryl);

Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together from a carbonyl group;

R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl, or R$_6$ and R$_7$ taken together form a carbonyl group;

R$_{10}$ is selected from hydrogen, alkyl, alkenyl, alkynyl, cycloalkyl, cycloalkenyl, aryl, heterocyclyl, heteroaryl, —C(R$_{14}$)$_3$, —C(O)R$_{13}$, —C(O)N(R$_{13}$)$_2$, —S(O)R$_{13}$, —S(O)$_2$R$_{13}$, —S(O)$_2$N(R$_{13}$)$_2$ and —CO$_2$R$_{13}$;

R$_{11}$ is selected from hydrogen and alkyl;

R$_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;
m is selected from an integer from 1 to 3;
p is selected from an integer of 1 or 2;
wherein each alkyl, alkenyl, alkynyl, cycloalkyl, cycloalkenyl, aryl, heterocyclyl and heteroaryl may be optionally substituted; or
a pharmaceutically acceptable salt thereof.

In particular embodiments of formula (I), one or more of the following applies:

Ring G is a 5 to 8 membered ring, especially a 6 to 8 membered ring, more especially a 7 membered ring;

X is absent or is selected from —$(CR_6R_7)_n$—, —W—, —$(CR_6R_7)_m$—W and —$(CR_6R_7)_p$—W—$(CR_6R_7)_p$—, especially —$CR_6R_7$—$CR_6R_7$—, —$CR_6R_7$—$CR_6R_7$—$CR_6R_7$—, —$CR_6R_7$—$CR_6R_7$—$CR_6R_7$—$CR_6R_7$—, —$CR_6R_7$—W—, —$CR_6R_7CR_6R_7$—W— and —$CR_6R_7$—W—$CR_6R_7$, more especially —$CR_6R_7$—$CR_6R_7$—, —$CR_6R_7$—$CR_6R_7$—$CR_6R_7$—, —$CR_6R_7$—$CR_6R_7$—$CR_6R_7$—$CR_6R_7$—, —$CR_6R_7$—$CR_6R_7$—W—, —$CR_6R_7CR_6R_7$—W— and —$CR_6R_7$—W—$CR_6R_7$, even more especially —$CH_2CH_2$—, —$CH_2CH_2CH_2$—, —$CH_2CH_2CH_2CH_2$—, —$CH_2W$—, —$CH_2CH_2W$—, —$CH_2WCH_2$—, for example —$CH_2CH_2$—, —$CH_2CH_2CH_2$—, —$CH_2CH_2CH_2CH_2$—, —$CH_2CH_2O$—, —$CH_2C(O)NH$—, —$CH_2NHC(O)$—, —$CH_2CH_2C(O)NH$—, —$CH_2CH_2NHC(O)$—, —$CH_2C(O)NHCH_2$—, —$CH_2NHC(O)CH_2$—, —$CH_2S(O)_2NH$—, —$CH_2NHS(O)_2$—, —$CH_2CH_2S(O)_2NH$—, —$CH_2CH_2NHS(O)_2$—, —$CH_2S(O)_2NHCH_2$— and —$CH_2NHS(O)_2CH_2$—, most especially —$CH_2CH_2$—, —$CH_2CH_2CH_2$—, —$CH_2CH_2CH_2CH_2$— and —$CH_2CH_2O$—;

Y is —$CR_8CR_9$— wherein $R_8$ and $R_9$ together with the carbon atoms to which they are attached form an optionally substituted five or six membered monocyclic or eight to ten membered bicyclic aromatic or heteroaromatic ring system. In particular embodiments, the aromatic or heteroaromatic ring system is selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl[b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, especially phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl and triazinyl, more especially phenyl, pyridinyl, thiophenyl, pyrrolyl pyrazolyl, imidazolyl, thiazolyl, isothiazolyl, pyridazinyl, pyrimidinyl and pyrazinyl, even more especially, phenyl, pyridinyl, thiophenyl and pyrrolyl, most especially phenyl, pyridinyl and thiophenyl, wherein each aromatic or heteroaromatic ring may be optionally substituted with one or more optional substituents. Particular optional substituents include —$C_{1-6}$alkyl, —$C_{1-6}$alkoxy, halo, —$C(R_{14})_3$ and —$OC(R_{14})_3$, especially methyl, methoxy, fluoro, chloro, —$CF_3$ and $OCF_3$; more especially methyl, methoxy, fluoro and chloro and in which sulphur atoms may be optionally substituted with one or two carbonyl groups;

Z is absent or is selected from —$CR_4R_5$— and —$CR_6R_7CR_4R_5$—, especially absent or —$CH_2$— and —$CH_2CH_2$, most especially absent.

In particular embodiments X, Y and Z together are selected from —$(CR_6R_7)CR_8CR_9$—, —$(CR_6R_7)_n$WCR$_8$CR$_9$—, —$(CR_6R_7)_p$W$(CR_6R_7)_p$CR$_8$CR$_9$—, —$(CR_6R_7)_p$CR$_8$CR$_9$$(CR_6R_7)_p$— and —$CR_6R_7$—W—CR$_8$CR$_9$—CR$_4$R$_5$—, especially —$CH_2CH_2CR_8CR_9$—, —$CH_2CH_2CH_2CR_8CR_9$—, —$CH_2CH_2CH_2CH_2CR_8CR_9$—, —$CH_2W$—$CR_8CR_9$—, —$CH_2CH_2WCR_8CR_9$—, —$CH_2WCH_2CR_8CR_9$—, —$CH_2CH_2CR_8CR_9CH_2$—, —$CH_2CR_8CR_9CH_2CH_2$— and —$CH_2WCR_8CR_9CH_2$—, more especially —$CH_2CH_2CR_8CR_9$—, —$CH_2CH_2CH_2CR_8CR_9$—, —$CH_2CH_2CH_2CH_2CR_8CR_9$—, —$CH_2CH_2OCR_8CR_9$, —$CH_2OCH_2CR_8CR_9$—, —$CH_2CH_2NH$—$CR_8CR_9$—, —$CH_2CH_2N(CH_3)$—$CR_8R_9$—, —$CH_2NHCH_2CR_8CR_9$—, —$CH_2N(CH_3)CH_2CR_8CR_9$—, —$CH_2CH_2CR_8CR_9CH_2$—, —$CH_2CR_8CR_9$—$CH_2$—, —$CH_2CR_8CR_9CH_2CH_2$—, —$CH_2OCR_8CR_9CH_2$—, —$CH_2NHCR_8CR_9CH_2$—, —$CH_2N(CH_3)CR_8CR_9CH_2$—, —$CH_2C(O)NHCR_8CR_9$—, —$CH_2NHC(O)CR_8CR_9$—, —$CH_2CH_2C(O)NHCR_8CR_9$—, —$CH_2CH_2NHC(O)CR_8CR_9$—, —$CH_2NHC(O)CH_2CR_8CR_9$—, —$CH_2C(O)NHCH_2CR_8CR_9$—, —$CH_2S(O)_2NHCR_8CR_9$—, —$CH_2NHS(O)_2CR_8CR_9$—, —$CH_2CH_2S(O)_2NHCR_8CR_9$—, —$CH_2CH_2NHS(O)_2CR_8CR_9$—, —$CH_2NHS(O)_2CH_2CR_8CR_9$— and —$CH_2S(O)_2NHCH_2CR_8CR_9$— most especially —$CH_2CH_2CR_8CR_9$—, —$CH_2CH_2CH_2CR_8CR_9$—, —$CH_2CH_2CH_2CH_2CR_8CR_9$—, —$CH_2CH_2OCR_8CR_9$, —$CH_2OCH_2CR_8CR_9$—, —$CH_2CH_2NH$—$CR_8CR_9$—, —$CH_2CH_2N(CH_3)$—$CR_8R_9$—, —$CH_2NHCH_2CR_8CR_9$—, —$CH_2N(CH_3)CH_2CR_8CR_9$—, —$CH_2CH_2CR_8CR_9CH_2$—, —$CH_2CR_8CR_9$—$CH_2$—, —$CH_2CR_8CR_9CH_2CH_2$—, —$CH_2OCR_8CR_9CH_2$—, —$CH_2NHCR_8CR_9CH_2$— and —$CH_2N(CH_3)CR_8CR_9CH_2$—.

In particular embodiments, Ring G together with $R_8$ and $R_9$ is selected from one of the following ring systems:

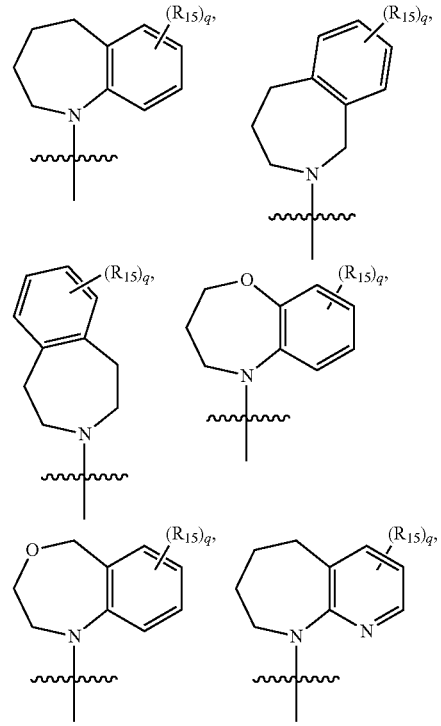

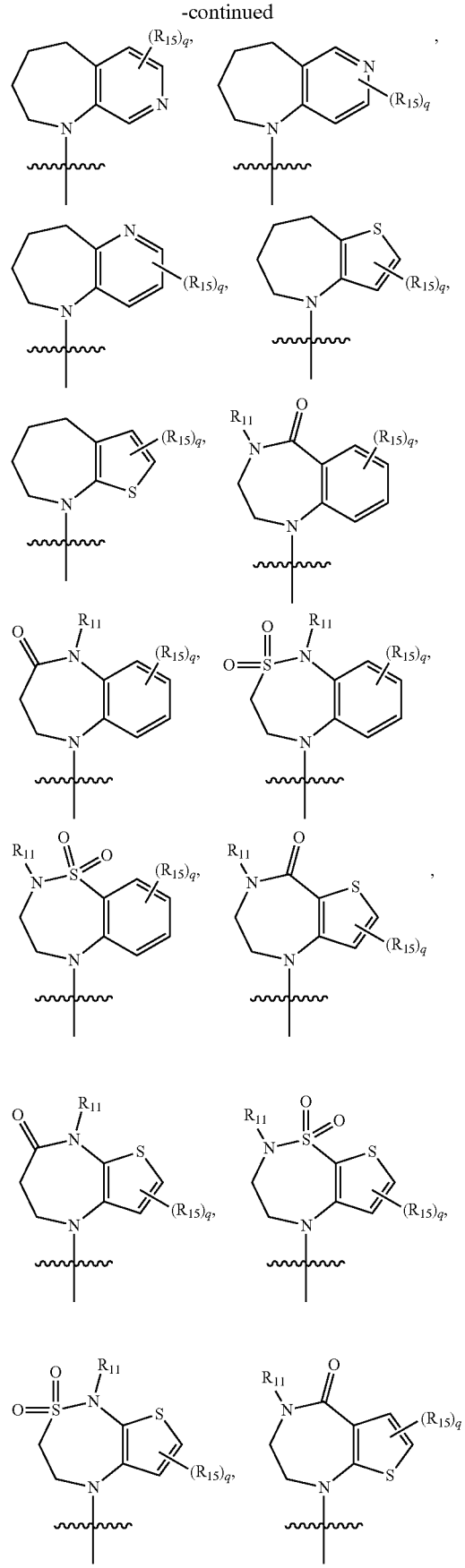
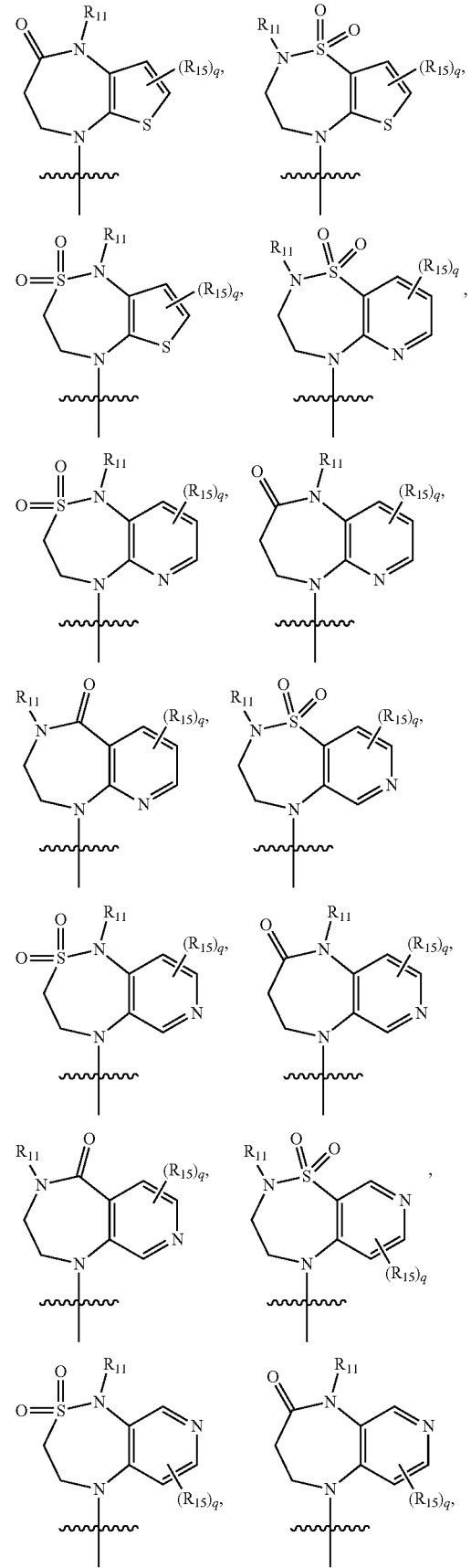

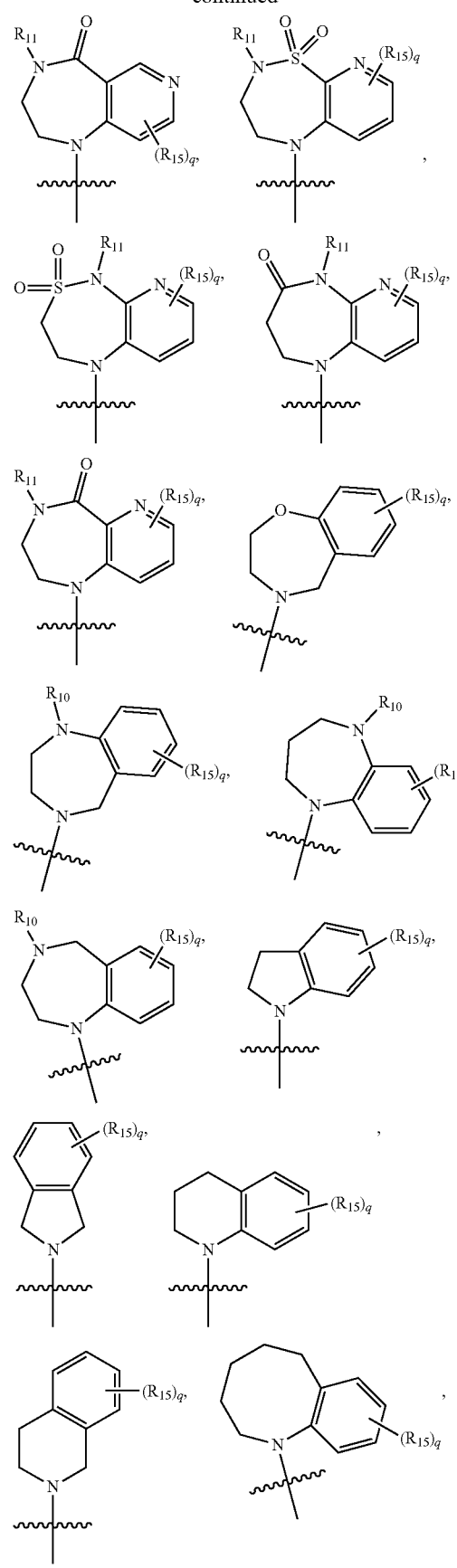
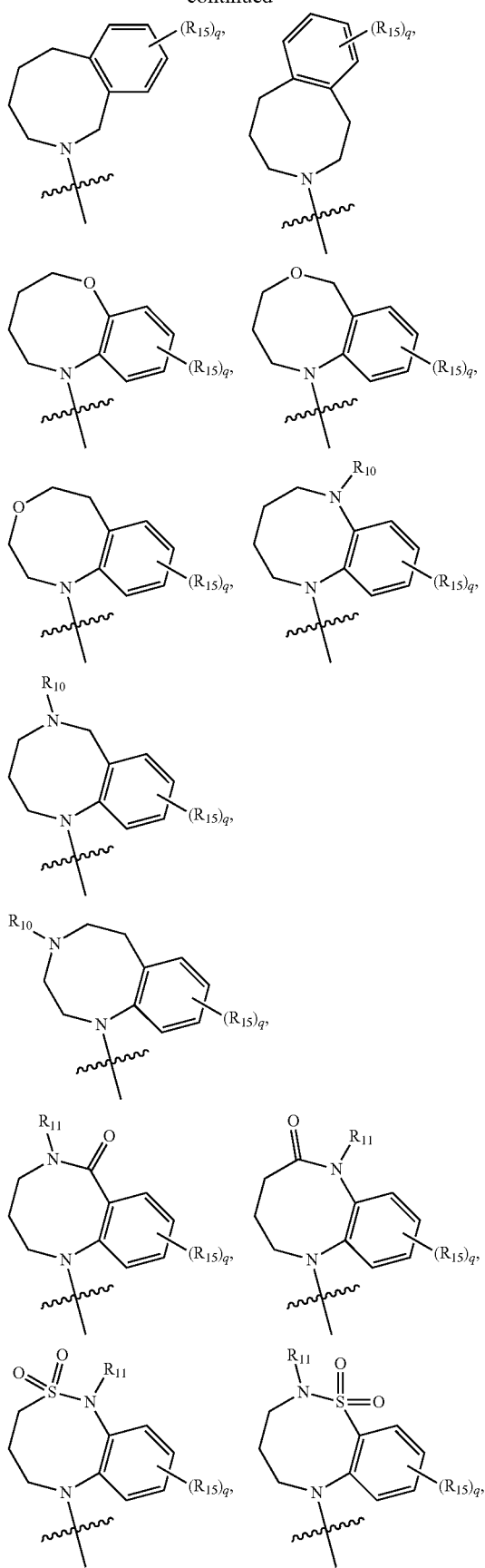

-continued
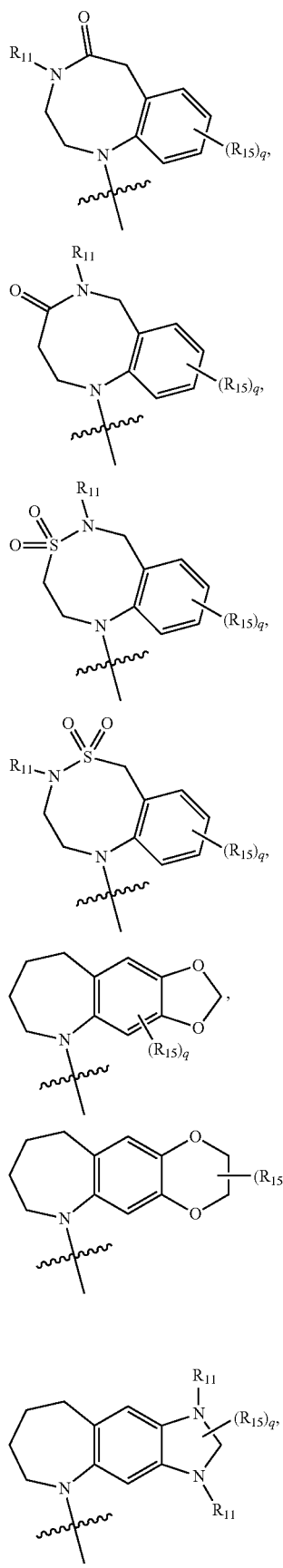
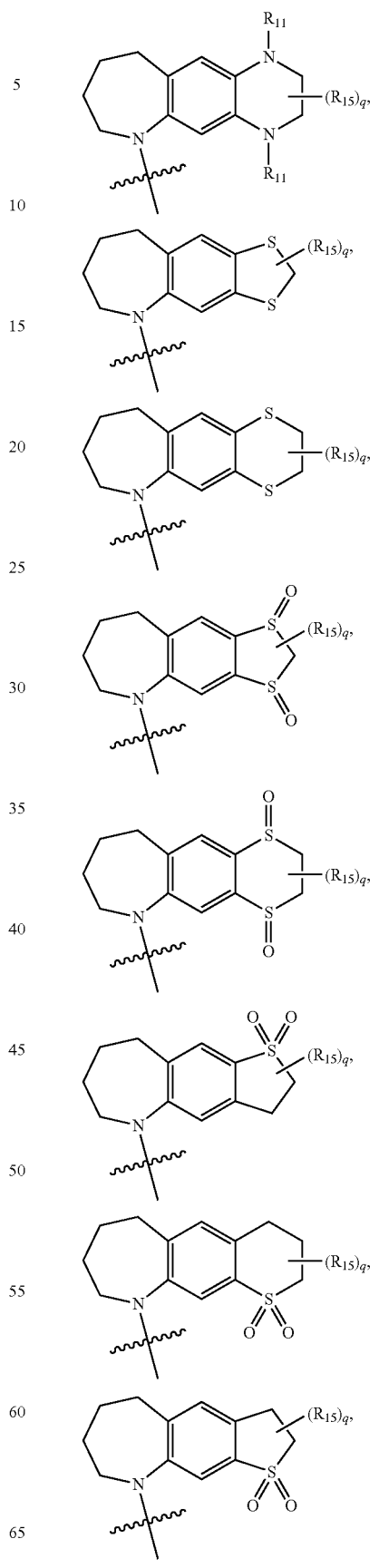

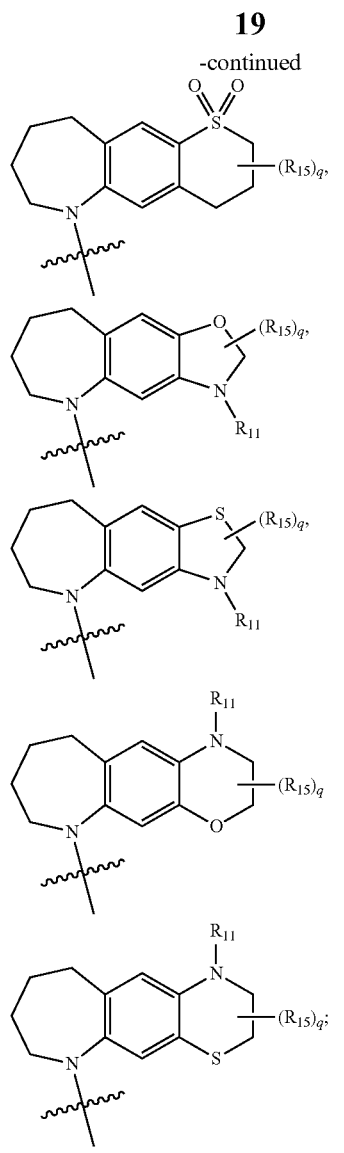
especially the following ring systems:
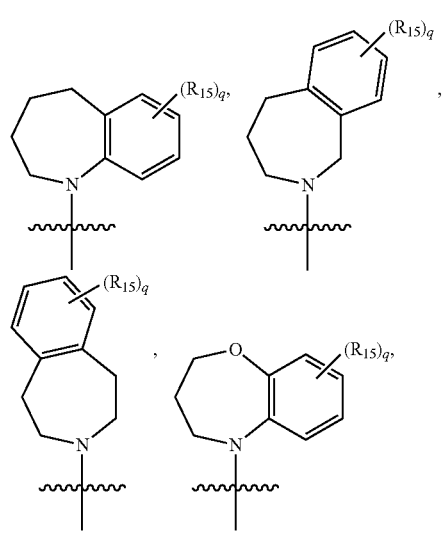
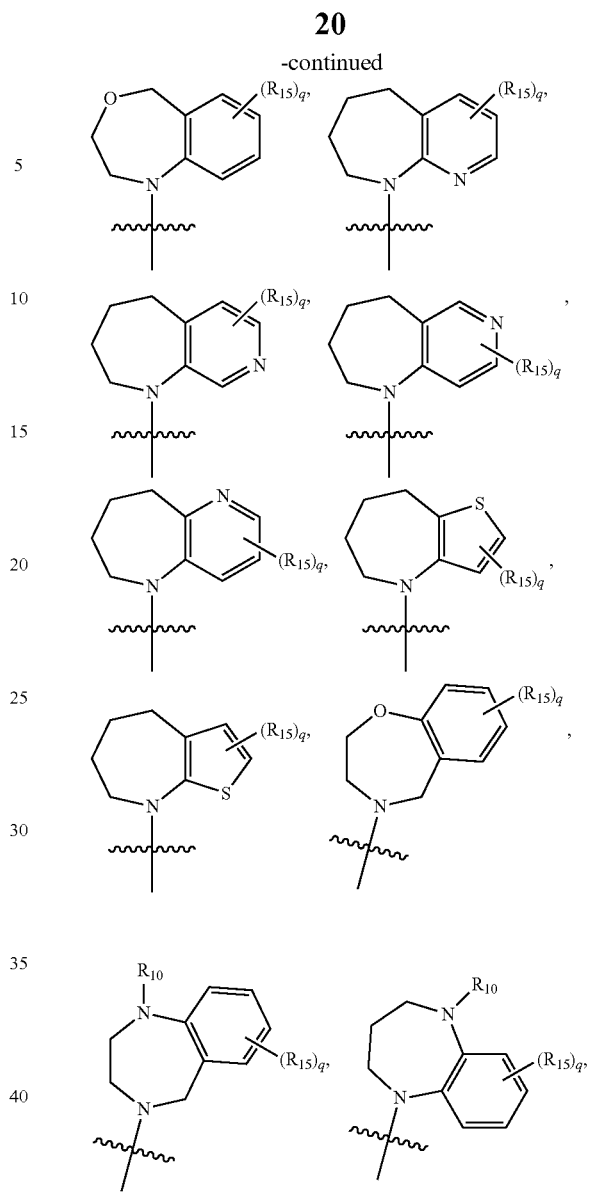
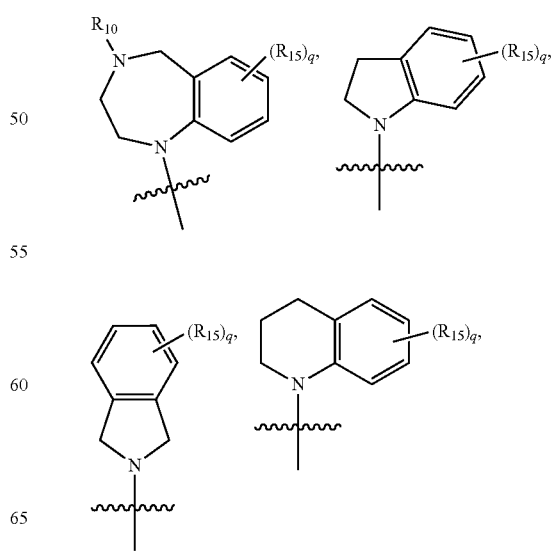

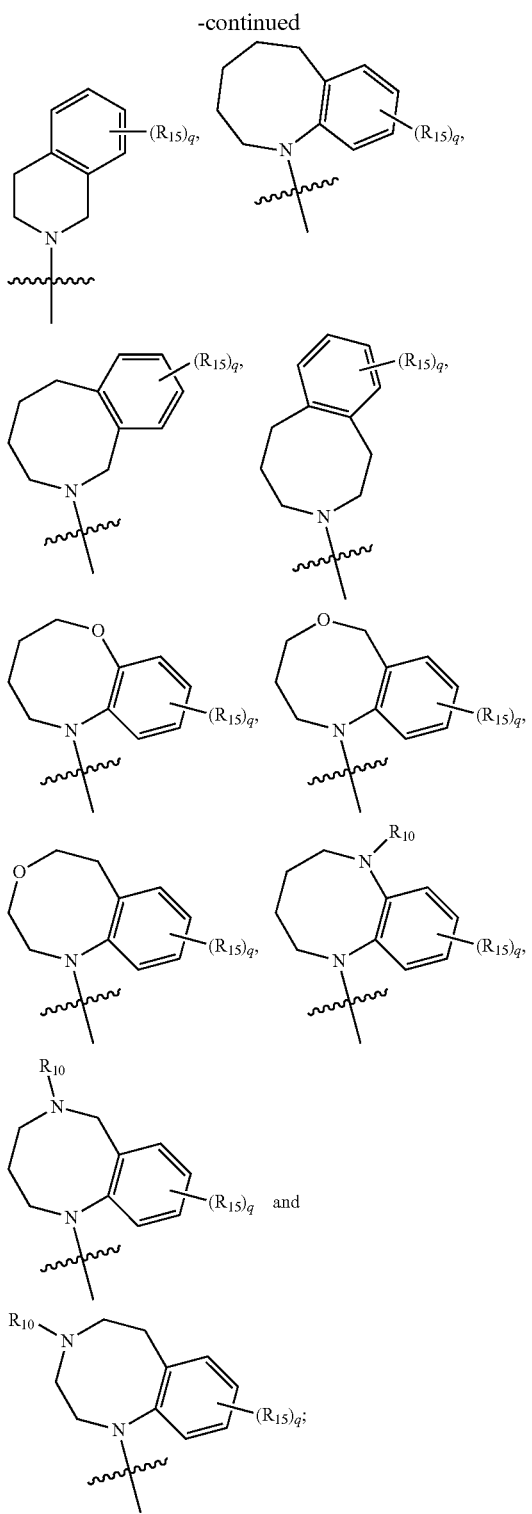

wherein each carbon atom in Ring G may be substituted with $R_4$, $R_5$, $R_6$ or $R_7$ as appropriate, each $R_{15}$ is independently selected from —$C_{1-6}$alkyl, —$C_{2-6}$alkenyl, —$C_{2-6}$alkynyl, —$OR_{13}$, —$SR_{13}$, halo, —CN, —$NO_2$, —$N(R_{13})_2$, —$CO_2R_{13}$, —$CON(R_{13})_2$, —$C(O)R_{13}$, —$S(O)_2R_{13}$, —$S(O)_2N(R_{13})_2$, —$C(R_{14})_3$, —$OC(R_{14})_3$, cycloalkyl, cycloalkenyl, aryl, heterocyclyl and heteroaryl and q is 0 or an integer from 1 to 4; and when q is less than the number of sites on the aryl or heteroaryl ring available for substitution, the carbon atoms not substituted with $R_{15}$ bear a hydrogen atom;

W is selected from —O—, —C(O)—, —S(O)$_2$—, —N($R_{10}$)—, —C(O)N($R_{11}$)—, —N($R_{11}$)C(O)—, —S(O)$_2$N($R_{11}$)— and —N($R_{11}$)S(O)$_2$—; especially —O— and —N($R_{10}$)—;

$R_1$ is selected from —$CO_2H$, —$CH_2CO_2H$, —C(O)C(O)OH, —C(O)$NH_2$, —CN, —C(O)NHSO$_2C_{1-6}$alkyl, —C(O)NHSO$_2C_{3-8}$cycloalkyl, —C(O)NHSO$_2$phenyl, —C(O)NHSO$_2$N($C_{1-6}$alkyl)$_2$, —C(O)NHSO$_2$N($C_{3-8}$cycloalkyl)$_2$, —C(O)NHSO$_2$N($C_{1-6}$alkyl)($C_{3-8}$cycloalkyl), —C(O)NHSO$_2CF_3$, tetrazole and tetrazolate, especially —$CO_2H$, —$CH_2CO_2H$, —C(O)$NH_2$, tetrazole, tetrazolate, —C(O)NHSO$_2C_{1-4}$alkyl, —C(O)NHSO$_2C_{3-6}$cycloalkyl, —C(O)NHSO$_2$phenyl, —C(O)NHSO$_2CF_3$, —C(O)NHSO$_2$N($C_{1-3}$alkyl)$_2$, —C(O)NHSO$_2$N($C_{1-3}$alkyl)($C_{3-6}$cycloalkyl) and —C(O)NHSO$_2$N($C_{3-6}$cycloalkyl)$_2$; more especially —$CO_2H$, —$CONH_2$, —C(O)NHSO$_2C_{3-6}$cycloalkyl and —C(O)NHSO$_2$N($C_{1-3}$alkyl)$_2$; most especially —$CO_2H$, —C(O)NHSO$_2C_{3-6}$cyclopropyl and —C(O)NHSO$_2$N($CH_3$)$_2$;

$R_2$ is selected from hydrogen, —$C_{1-6}$alkyl, —$C_{1-4}$alkylene$R_{12}$, —$C_{2-4}$alkenylene$R_{12}$ and —$C_{2-4}$alkynylene$R_{12}$, especially hydrogen and $C_{1-6}$alkyl, more especially hydrogen and methyl;

$R_3$ is selected from —C(O)CH(phenyl)(phenyl) and —C(O)N(phenyl)(phenyl), especially —C(O)CH(phenyl)(phenyl) wherein each phenyl group is independently optionally substituted with one or more optional substituents selected from —$C_{1-6}$alkyl, —OH, —O$C_{1-6}$alkyl, —CN, —$NO_2$, halo, —$CF_3$, —$OCF_3$, —$CHF_2$, —$OCHF_2$, —$CH_2F$, —$OCH_2F$, —$NH_2$, —NH($C_{1-6}$alkyl), —N($C_{1-6}$alkyl)$_2$, —$CO_2H$, —$CO_2C_{1-6}$alkyl, —$CONH_2$, —$SO_2C_{1-6}$alkyl and —$SO_2NH_2$;

$R_4$ and $R_5$ are each independently selected from hydrogen, —$C_{1-6}$alkyl, —$C_{2-6}$alkenyl, —$C_{2-6}$alkynyl, —OH, —$CF_3$, —$CHF_2$, —$CH_2F$, —$OCF_2$, —$OCHF_2$, —$OCH_2F$, —CN, —$NO_2$, —$NH_2$, —NH($C_{1-6}$alkyl), —N($C_{1-6}$alkyl)$_2$, —NH(aryl), —N($C_{1-6}$alkyl)(phenyl), —N(phenyl)$_2$, —$CO_2H$, —$CO_2C_{1-6}$alkyl, —$CO_2C_{2-6}$alkenyl, —$CO_2$phenyl, —C(O)$NH_2$, —C(O)NH$C_{1-6}$alkyl, —C(O)N($C_{1-6}$alkyl)$_2$, —C(O)$C_{1-6}$alkyl, —C(O)$C_{2-6}$alkenyl, —C(O)$C_{2-6}$alkynyl, —S(O)$_2C_{1-6}$alkyl, —S(O)$_2$aryl, —S(O)$_2NH_2$, —S(O)$_2$NH($C_{1-6}$alkyl) and —S(O)$_2$N($C_{1-6}$alkyl)$_2$, especially hydrogen, —$C_{1-6}$alkyl, —$CF_3$, —$CHF_2$, —$CH_2F$, halo, —OH, —$OCF_2$, —$OCHF_2$, —$OCH_2F$, —CN, —$NO_2$, —$NH_2$, —NH($C_{1-6}$alkyl), —N($C_{1-6}$alkyl)$_2$, —$CO_2H$, —$CO_2C_{1-6}$alkyl, —$CO_2NH_2$, —S(O)$_2C_{1-6}$alkyl, —S(O)$_2NH_2$, —S(O)NH($C_{1-6}$alkyl), —S(O)$_2$N($C_{1-6}$alkyl)$_2$ and —C(O)$C_{1-6}$alkyl, more especially hydrogen, —$C_{1-6}$alkyl, —$CF_3$, —$CHF_2$, —$CH_2F$, —OH, —$OCF_2$, —$OCHF_2$, —$OCH_2F$, —CN, —$NO_2$, —$NH_2$, —$CO_2H$ and —$CONH_2$, most especially hydrogen, —$C_{1-6}$alkyl and —$CF_3$;

Each $R_6$ and $R_7$ are independently selected from hydrogen, —$C_{1-6}$alkyl, —$C_{2-6}$alkenyl, —$C_{2-6}$alkynyl, halo, —OH, —O$C_{1-6}$alkyl, —O$C_{2-6}$alkenyl, —O$C_{2-6}$alkynyl, —CN, —$NO_2$, —$NH_2$, —NH($C_{1-6}$alkyl), —N($C_{1-6}$alkyl)$_2$, —NH(aryl), —N($C_{1-6}$alkyl)(phenyl), —N(phenyl)$_2$, —$CO_2H$, —$CO_2C_{1-6}$alkyl, —$CO_2C_{2-6}$alkenyl, —$CF_3$, —$CH_2F$, —$OCF_2$, —$OCHF_2$, —$OCH_2F$, —$CO_2$phenyl, —C(O)$NH_2$, —C(O)NH$C_{1-6}$alkyl, —C(O)N($C_{1-6}$alkyl)$_2$, —C(O)$C_{1-6}$alkyl, —C(O)$C_{2-6}$alkenyl, —C(O)$C_{2-6}$alkynyl, —S(O)$_2C_{1-6}$alkyl, —S(O)$_2$aryl, —S(O)$_2NH_2$, —S(O)$_2$NH($C_{1-6}$alkyl) and —S(O)$_2$N($C_{1-6}$alkyl)$_2$, especially hydrogen, —$C_{1-6}$alkyl, —$CF_3$, —$CHF_2$, —$CH_2F$, halo, —OH, —OCF₂, —OCHF₂, —OCH₂F, —OC₁₋₆alkyl, —CN, —NO₂, —NH₂, —NH(C₁₋₆alkyl), —N(C₁₋₆alkyl)₂, —CO₂H, —CO₂C₁₋₆alkyl, —CO₂NH₂, —S(O)₂C₁₋₆alkyl, —S(O)₂NH₂, —S(O)NH(C₁₋₆alkyl), —S(O)₂N(C₁₋₆alkyl)₂ and —C(O)C₁₋₆alkyl, more especially hydrogen, —C₁₋₆alkyl, —CF₃, —CHF₂, —CH₂F, halo, —OH, —OCF₂, —OCHF₂, —OCH₂F, —CN, —NO₂, —NH₂, —CO₂H and —CONH₂, most especially hydrogen, —C₁₋₆alkyl, —CF₃ and halo;

$R_{10}$ is selected from hydrogen, $C_{1-6}$alkyl, —C(O)C₁₋₆alkyl, —C(O)C₂₋₆alkenyl, —C(O)C₂₋₆alkynyl, —C(O)C₂₋₆alkynyl, —CO₂H, —CO₂C₁₋₆alkyl, —CO₂C₂₋₆alkenyl, —CO₂C₂₋₆alkynyl, —C(O)NH₂, —C(O)NH(C₁₋₆alkyl), —C(O)NH(C₂₋₆alkenyl), —C(O)NH(C₂₋₆alkynyl), —C(O)N(C₁₋₆alkyl)₂, —SO₂C₁₋₆alkyl, —SO₂C₂₋₆alkenyl, —SO₂C₂₋₆alkynyl, —SO₂NH₂, —SO₂NH(C₁₋₆alkyl), —SO₂NH(C₂₋₆alkenyl), —SO₂NH(C₂₋₆alkynyl), —SO₂N(C₁₋₆alkyl)₂, —SO₂CF₃, —SO₂NHC(O)NH₂, —SO₂NHC(O)NH(C₁₋₆alkyl) and —SO₂NHC(O)N(C₁₋₆alkyl)₂, especially hydrogen, C₁₋₆alkyl, —C(O)C₁₋₆alkyl, —CO₂H, —CO₂C₁₋₆alkyl, —C(O)NH₂, —C(O)NH(C₁₋₆alkyl), —C(O)N(C₁₋₆alkyl)₂, —SO₂alkyl, —SO₂NH₂, —SO₂NH(C₁₋₆alkyl), —SO₂N(C₁₋₆alkyl)₂, —SO₂CF₃, —SO₂NHC(O)NH₂, —SO₂NHC(O)NH(C₁₋₆alkyl) and —SO₂NHC(O)N(C₁₋₆alkyl)₂;

$R_{11}$ is selected from hydrogen or $C_{1-3}$alkyl, especially hydrogen and methyl;

$R_{12}$ is selected from cycloalkyl and aryl, especially $C_{3-6}$cycloalkyl and aryl, more especially cyclopropyl, cyclopentyl, cyclohexyl and phenyl;

Each $R_{13}$ is independently selected from hydrogen, $C_{1-6}$alkyl, $C_{3-6}$cycloalkyl, $C_{5-6}$cycloalkenyl and phenyl;

Each $R_{14}$ is independently selected from hydrogen and fluorine;

n is 1, 2 or 3, especially 2 or 3, more especially 3; and m is 1 or 2.

In particular embodiments, the stereogenic carbon atom bearing $R_1$ and $R_2$ substituents is in the S configuration.

In one embodiment, the compound of formula (I) is a compound of formula (II):

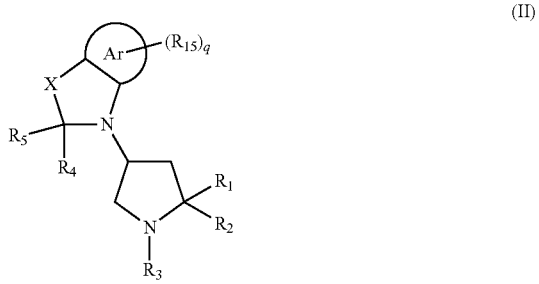

(II)

wherein
X is selected from —(CR₆R₇)ₙ—, —W—, —(CR₆R₇)ₘ—W—, —W—(CR₆R₇)ₘ— and —(CR₆R₇)ₚ—W—(CR₆R₇)ₚ—;

Ar is an aromatic or heteroaromatic ring or ring system;

$R_1$ is selected from —CO₂H, —CH₂CO₂H, —C(O)C(O)OH, —CH₂OH, —C(O)NH₂, —CN, —CH₂C(O)NH₂, —CH₂CN, a carboxylic acid bioisostere and —CH₂carboxylic acid bioisostere;

$R_2$ is selected from hydrogen, alkyl, alkenyl, alkynyl, —C₁₋₆alkyleneR₁₂, —C₂₋₆alkenyleneR₁₂ and —C₂₋₆alkynyleneR₁₂;

$R_3$ is selected from —C(O)CH(aryl)(aryl) and —C(O)N(aryl)(aryl);

Each $R_4$ and $R_5$ are independently selected from hydrogen, alkyl, alkenyl, alkynyl, —OC(R₁₄)₃, —CN, —NO₂, —N(R₁₃)₂, —CO₂R₁₃, —C(O)R₁₃, —C(O)N(R₁₃)₂, —S(O)₂R₁₃, —S(O)₂N(R₁₃)₂, —C(R₁₄)₃, cycloalkyl, cycloalkenyl, aryl, heterocyclyl and heteroaryl, or $R_4$ and $R_5$ taken together from a carbonyl group;

$R_6$ and $R_7$ are independently selected from hydrogen, alkyl, alkenyl, alkynyl, —OR₁₃, —SR₁₃, halo, —CN, —NO₂, —N(R₁₃)₂, —CO₂R₁₃, —C(O)R₁₃, —C(O)N(R₁₃)₂, —S(O)₂R₁₃, S(O)₂N(R₁₃)₂, —C(R₁₄)₃, —OC(R₁₄)₃, cycloalkyl, cycloalkenyl, aryl, heterocyclyl and heteroaryl, or $R_6$ and $R_7$ taken together form a carbonyl group;

W is selected from —O—, —S—, —S(O)—, —S(O)₂—, —C(O)—, —NR₁₀—, —C(O)N(R₁₁)—, —N(R₁₁)C(O)—, —C(O)O—, —OC(O)—, —S(O)₂N(R₁₁)—, —N(R₁₁)S(O)₂—, —N(R₁₁)C(O)N(R₁₁)— and —N(R₁₁)S(O)₂N(R₁₁)—;

$R_{10}$ is selected from hydrogen, alkyl, alkenyl, alkynyl, cycloalkyl, cycloalkenyl, aryl, heterocyclyl, heteroaryl, —C(R₁₄)₃, —C(O)R₁₃, —C(O)N(R₁₃)₂, —S(O)R₁₃, —S(O)₂R₁₃, —S(O)₂N(R₁₃)₂ and —CO₂R₁₃;

$R_{11}$ is selected from hydrogen and alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

Each $R_{15}$ is independently selected from —C₁₋₆alkyl, —C₂₋₆alkenyl, —C₂₋₆alkynyl, —OR₁₃, —SR₁₃, halo, —CN, —NO₂, —N(R₁₃)₂, —CO₂R₁₃, —CON(R₁₃)₂, —C(O)R₁₃, —S(O)₂R₁₃, —S(O)₂N(R₁₃)₂, —C(R₁₄)₃, —OC(R₁₄)₃, cycloalkyl, cycloalkenyl, aryl, heterocyclyl and heteroaryl;

m is selected from an integer from 1 to 3;
n is selected from an integer from 1 to 4;
p is selected from an integer of 1 or 2; and
q is 0 or an integer of 1 to 4;

wherein each alkyl, alkenyl, alkynyl, cycloalkyl, cycloalkenyl, aryl, heterocyclyl and heteroaryl may be optionally substituted; or
a pharmaceutically acceptable salt thereof.

In particular embodiments of formula (II), one or more of the following applies:

X is absent or is selected from —(CR₆R₇)ₙ—, —W—, —(CR₆R₇)ₘ—W— and —(CR₆R₇)ₚ—W—(CR₆R₇)ₚ—, especially —CR₆R₇—CR₆R₇—, —CR₆R₇—CR₆R₇—CR₆R₇—, —CR₆R₇—CR₆R₇—CR₆R₇—CR₆R₇—, —CR₆R₇—W—, —CR₆R₇CR₆R₇—W— and —CR₆R₇—W—CR₆R₇, more especially —CR₆R₇—CR₆R₇—, —CR₆R₇—CR₆R₇—CR₆R₇—, —CR₆R₇—CR₆R₇—CR₆R₇—CR₆R₇—, —CR₆R₇—W—, —CR₆R₇CR₆R₇—W— and —CR₆R₇—W—CR₆R₇, for example —CH₂CH₂—, —CH₂CH₂CH₂—, —CH₂CH₂CH₂CH₂—, —CH₂CH₂W—, —CH₂WCH₂—, even more especially —CH₂CH₂—, —CH₂CH₂CH₂—, —CH₂CH₂CH₂CH₂—, —CH₂CH₂O—, —CH₂C(O)NH—, —CH₂NHC(O)—, —CH₂CH₂C(O)NH—, —CH₂CH₂NHC(O)—, —CH₂C(O)NHCH₂—, —CH₂NHC(O)CH₂—, —CH₂S(O)₂NH—, —CH₂NITS(O)₂—, —CH₂CH₂S(O)₂NH—, —CH₂CH₂NHS(O)₂—, —CH₂S(O)₂NHCH₂— and —CH₂NHS(O)₂CH₂— most especially —CH₂CH₂—, —CH₂CH₂CH₂—, —CH₂CH₂CH₂CH₂— and —CH₂CH₂O—;

Ar is a 5 or 6 membered monocyclic or 8 to 10 membered bicyclic aromatic or heteroaromatic ring system, for example one selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl[b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, especially phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl and triazinyl, more especially phenyl, pyridinyl, thiophenyl, pyrrolyl pyrazolyl, imidazolyl, thiazolyl, isothiazolyl, pyridazinyl, pyrimidinyl and pyrazinyl, even more especially, phenyl, pyridinyl, thiophenyl and pyrrolyl, most especially phenyl, pyridinyl and thiophenyl. In some embodiments Ar is an aryl or heteroaryl ring system selected from one of the following:

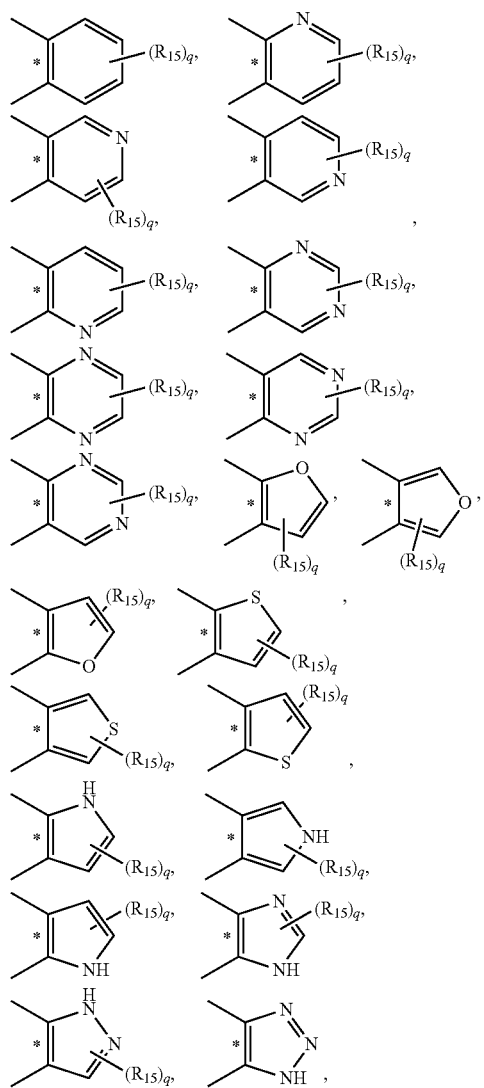

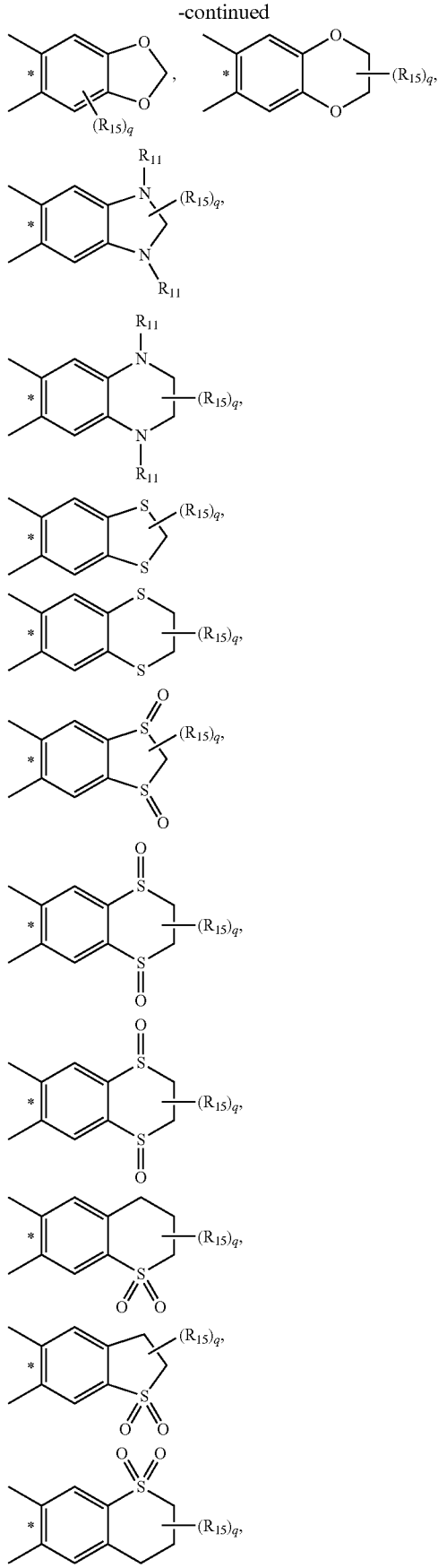

-continued

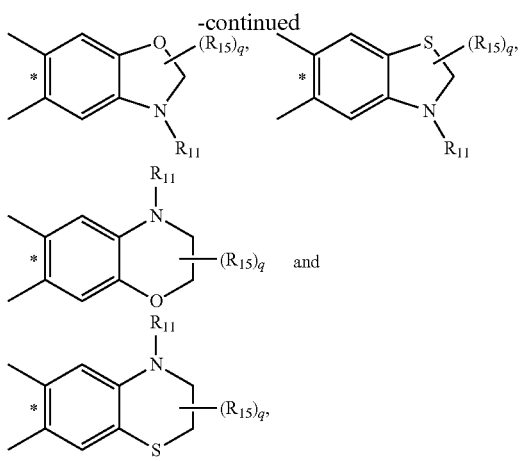

especially

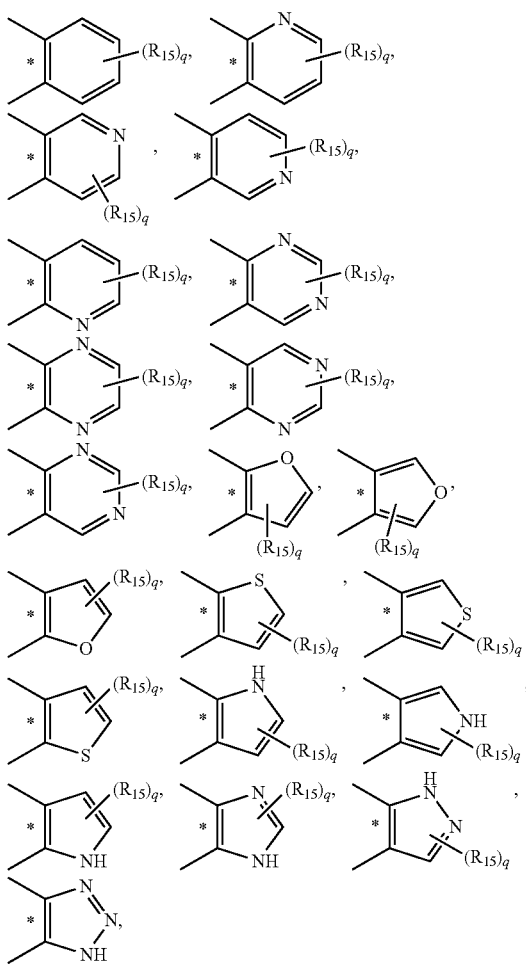

more especially

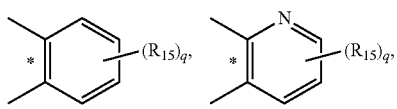

-continued

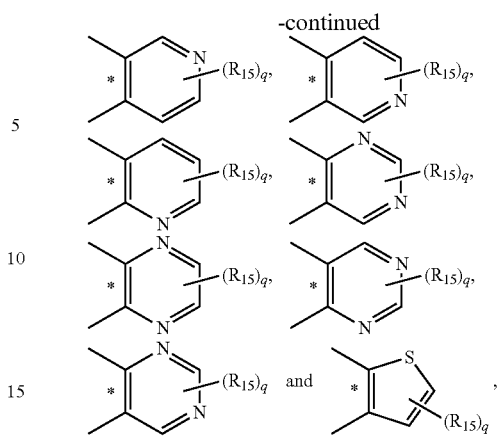

most especially

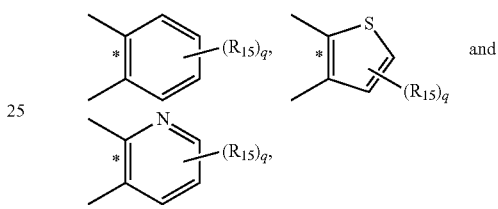

wherein * represents the common bond with Ring G; and when q is less than the number of sites on the aryl or heteroaryl ring available for substitution, the carbon atoms not substituted with $R_{15}$ bear a hydrogen atom;

$R_1$ is selected from —$CO_2H$, —$CH_2CO_2H$, —C(O)C(O)OH, —C(O)$NH_2$, —CN, —C(O)$NHSO_2C_{1-6}$alkyl, —C(O)$NHSO_2C_{3-8}$cycloalkyl, —C(O)$NHSO_2$phenyl, —C(O)$NHSO_2N(C_{1-6}$alkyl$)_2$, —C(O)$NHSO_2N(C_{3-8}$cycloalkyl$)_2$, —C(O)$NHSO_2N(C_{1-6}$alkyl$)(C_{3-8}$cycloalkyl), —C(O)$NHSO_2CF_3$, tetrazole and tetrazolate, especially —$CO_2H$, —$CH_2CO_2H$, —C(O)$NH_2$, tetrazole, tetrazolate, —C(O)$NHSO_2C_{1-4}$alkyl, —C(O)$NHSO_2C_{3-6}$cycloalkyl, —C(O)$NHSO_2$phenyl, —C(O)$NHSO_2CF_3$, —C(O)$NHSO_2N(C_{1-3}$alkyl$)_2$, —C(O)$NHSO_2N(C_{1-3}$alkyl$)(C_{3-6}$cycloalkyl) and —C(O)$NHSO_2N(C_{3-6}$cycloalkyl$)_2$; more especially —$CO_2H$, —$CONH_2$, —C(O)$NHSO_2C_{3-6}$cycloalkyl and —C(O)$NHSO_2N(C_{1-3}$alkyl$)_2$; most especially —$CO_2H$, —C(O)$NHSO_2C_{3-6}$cyclopropyl and —C(O)$NHSO_2N(CH_3)_2$;

$R_2$ is selected from hydrogen, —$C_{1-6}$alkyl, —$C_{1-4}$alkylene$R_{12}$, —$C_{2-4}$alkenylene$R_{12}$ and —$C_{2-4}$alkynylene$R_{12}$, especially hydrogen and $C_{1-6}$alkyl, more especially hydrogen and methyl;

$R_3$ is selected from —C(O)CH(phenyl)(phenyl) and —C(O)N(phenyl)(phenyl), especially —C(O)CH(phenyl)(phenyl) wherein each phenyl group is independently optionally substituted with one or more optional substituents selected from —$C_{1-6}$alkyl, —OH, —$OC_{1-6}$alkyl, —CN, —$NO_2$, halo, —$CF_3$, —$OCF_3$, —$CHF_2$, —$OCHF_2$, —$CH_2F$, —$OCH_2F$, —$NH_2$, —NH($C_{1-6}$alkyl), —N($C_{1-6}$alkyl$)_2$, —$CO_2H$, —$CO_2C_{1-6}$alkyl, —$CONH_2$, —$SO_2C_{1-6}$alkyl and —$SO_2NH_2$;

$R_4$ and $R_5$ are each independently selected from hydrogen, —$C_{1-6}$alkyl, —$C_{2-6}$alkenyl, —$C_{2-6}$alkynyl, —OH, —$CF_3$, —$CHF_2$, —$CH_2F$, —$OCF_2$, —$OCHF_2$, —$OCH_2F$, —CN, —$NO_2$, —$NH_2$, —NH($C_{1-6}$alkyl), —N($C_{1-6}$alkyl$)_2$, —NH(aryl), —N($C_{1-6}$alkyl)(phenyl), —N(phenyl$)_2$, —$CO_2H$, —CO$_2$C$_{1-6}$alkyl, —CO$_2$C$_{2-6}$alkenyl, —CO$_2$phenyl, —C(O)NH$_2$, —C(O)NHC$_{1-6}$alkyl, —C(O)N(C$_{1-6}$alkyl)$_2$, —C(O)C$_{1-6}$alkyl, —C(O)C$_{2-6}$alkenyl, —C(O)C$_{2-6}$alkynyl, —S(O)$_2$C$_{1-6}$alkyl, —S(O)$_2$aryl, —S(O)$_2$NH$_2$, —S(O)$_2$NH(C$_{1-6}$alkyl) and —S(O)$_2$N(C$_{1-6}$alkyl)$_2$, especially hydrogen, —C$_{1-6}$alkyl, —CF$_3$, —CHF$_2$, —CH$_2$F, halo, —OH, —OCF$_2$, —OCHF$_2$, —OCH$_2$F, —CN, —NO$_2$, —NH$_2$, —NH(C$_{1-6}$alkyl), —N(C$_{1-6}$alkyl)$_2$, —CO$_2$H, —CO$_2$C$_{1-6}$alkyl, —CO$_2$NH$_2$, —S(O)$_2$C$_{1-6}$alkyl, —S(O)$_2$NH$_2$, —S(O)NH(C$_{1-6}$alkyl), —S(O)$_2$N(C$_{1-6}$alkyl)$_2$ and —C(O)C$_{1-6}$alkyl, more especially hydrogen, —C$_{1-6}$alkyl, —CF$_3$, —CHF$_2$, —CH$_2$F, —OH, —OCF$_2$, —OCHF$_2$, —OCH$_2$F, —CN, —NO$_2$, —NH$_2$, —CO$_2$H and —CONH$_2$, most especially hydrogen, —C$_{1-6}$alkyl and —CF$_3$;

Each R$_6$ and R$_7$ are independently selected from hydrogen, —C$_{1-6}$alkyl, —C$_{2-6}$alkenyl, —C$_{2-6}$alkynyl, halo, —OH, —OC$_{1-6}$alkyl, —OC$_{2-6}$alkenyl, —OC$_{2-6}$alkynyl, —CN, —NO$_2$, —NH$_2$, —NH(C$_{1-6}$alkyl), —N(C$_{1-6}$alkyl)$_2$, —NH(aryl), —N(C$_{1-6}$alkyl)(phenyl), —N(phenyl)$_2$, —CO$_2$H, —CO$_2$C$_{1-6}$alkyl, —CO$_2$C$_{2-6}$alkenyl, —CF$_3$, —CHF$_2$, —CH$_2$F, —OCF$_2$, —OCHF$_2$, —OCH$_2$F, —CO$_2$phenyl, —C(O)NH$_2$, —C(O)NHC$_{1-6}$alkyl, —C(O)N(C$_{1-6}$alkyl)$_2$, —C(O)C$_{1-6}$alkyl, —C(O)C$_{2-6}$alkenyl, —C(O)C$_{2-6}$alkynyl, —S(O)$_2$C$_{1-6}$alkyl, —S(O)$_2$aryl, —S(O)$_2$NH$_2$, —S(O)$_2$NH(C$_{1-6}$alkyl) and —S(O)$_2$N(C$_{1-6}$alkyl)$_2$, especially hydrogen, —C$_{1-6}$alkyl, —CF$_3$, —CHF$_2$, —CH$_2$F, halo, —OH, —OCF$_2$, —OCHF$_2$, —OCH$_2$F, —OC$_{1-6}$alkyl, —CN, —NO$_2$, —NH$_2$, —NH(C$_{1-6}$alkyl), —N(C$_{1-6}$alkyl)$_2$, —CO$_2$H, —CO$_2$C$_{1-6}$alkyl, —CO$_2$NH$_2$, —S(O)$_2$C$_{1-6}$alkyl, —S(O)$_2$NH$_2$, —S(O)NH(C$_{1-6}$alkyl), —S(O)$_2$N(C$_{1-6}$alkyl)$_2$ and —C(O)C$_{1-6}$alkyl, more especially hydrogen, —C$_{1-6}$alkyl, —CF$_3$, —CHF$_2$, —CH$_2$F, halo, —OH, —OCF$_2$, —OCHF$_2$, —OCH$_2$F, —CN, —NO$_2$, —NH$_2$, —CO$_2$H and —CONH$_2$, most especially hydrogen, —C$_{1-6}$alkyl, —CF$_3$ and halo;

R$_{10}$ is selected from hydrogen, C$_{1-6}$alkyl, —C(O)C$_{1-6}$alkyl, —C(O)C$_{2-6}$alkenyl, —C(O)C$_{2-6}$alkynyl, —C(O)C$_{2-6}$alkynyl, —CO$_2$H, —CO$_2$C$_{1-6}$alkyl, —CO$_2$C$_{2-6}$alkenyl, —CO$_2$C$_{2-6}$alkynyl, —C(O)NH$_2$, —C(O)NH(C$_{1-6}$alkyl), —C(O)NH(C$_{2-6}$alkenyl), —C(O)NH(C$_{2-6}$alkynyl), —C(O)N(C$_{1-6}$alkyl)$_2$, —SO$_2$C$_{1-6}$alkyl, —SO$_2$C$_{2-6}$alkenyl, —SO$_2$C$_{2-6}$alkynyl, —SO$_2$NH$_2$, —SO$_2$NH(C$_{1-6}$alkyl), —SO$_2$NH(C$_{2-6}$alkenyl), —SO$_2$NH(C$_{2-6}$alkynyl), —SO$_2$N(C$_{1-6}$alkyl)$_2$, —SO$_2$CF$_3$, —SO$_2$NHC(O)NH$_2$, —SO$_2$NHC(O)NH(C$_{1-6}$alkyl) and —SO$_2$NHC(O)N(C$_{1-6}$alkyl)$_2$, especially hydrogen, C$_{1-6}$alkyl, —C(O)C$_{1-6}$alkyl, —CO$_2$H, —CO$_2$C$_{1-6}$alkyl, —C(O)NH$_2$, —C(O)NH(C$_{1-6}$alkyl), —C(O)N(C$_{1-6}$alkyl)$_2$, —SO$_2$alkyl, —SO$_2$NH$_2$, —SO$_2$NH(C$_{1-6}$alkyl), —SO$_2$N(C$_{1-6}$alkyl)$_2$, —SO$_2$CF$_3$, —SO$_2$NHC(O)NH$_2$, —SO$_2$NHC(O)NH(C$_{1-6}$alkyl) and —SO$_2$NHC(O)N(C$_{1-6}$alkyl)$_2$;

R$_{11}$ is selected from hydrogen or C$_{1-3}$alkyl, especially hydrogen and methyl;

R$_{12}$ is selected from cycloalkyl and aryl, especially C$_{3-6}$cycloalkyl and aryl, more especially cyclopropyl, cyclopentyl, cyclohexyl and phenyl;

Each R$_{13}$ is independently selected from hydrogen, C$_{1-6}$alkyl, C$_{3-6}$cycloalkyl, C$_{5-6}$cycloalkenyl and phenyl;

Each R$_{14}$ is independently selected from hydrogen and fluorine;

Each R$_{15}$ is independently selected from —C$_{1-6}$alkyl, —CF$_3$, —CHF$_2$, —CH$_2$F, halo, —OH, —OC$_{1-6}$alkyl, —OCF$_2$, —OCHF$_2$, —OCH$_2$F, —CO$_2$H, —CO$_2$H, —S(O)$_2$C$_{1-6}$alkyl, —S(O)$_2$aryl, —S(O)$_2$NH$_2$, —S(O)$_2$NH(C$_{1-6}$alkyl), —S(O)$_2$N(C$_{1-6}$alkyl)$_2$, —CN, —NO$_2$, —NH$_2$, —NH(C$_{1-6}$alkyl) and —N(C$_{1-6}$alkyl)$_2$, especially —C$_{1-6}$alkyl, —CF$_3$, —CHF$_2$, —CH$_2$F, halo, —OC$_{1-6}$alkyl, —OCF$_2$, —OCHF$_2$, —OCH$_2$F, —S(O)$_2$C$_{1-6}$alkyl, —S(O)$_2$aryl, —S(O)$_2$NH$_2$, —S(O)$_2$NH(C$_{1-6}$alkyl), —S(O)$_2$N(C$_{1-6}$alkyl)$_2$ and —CN; especially —C$_{1-6}$alkyl, —C$_{1-6}$alkoxy, halo, —C(R$_{14}$)$_3$ and —OC(R$_{14}$)$_3$, especially methyl, methoxy, fluoro, chloro, —CF$_3$ and OCF$_3$; more especially methyl, methoxy, fluoro and chloro;

n is 1, 2 or 3, especially 2 or 3, more especially 3;

m is 1 or 2;

q is 0 or 1 to 3, especially 0 or 1 or 2, more especially 0 or 1.

Particular compounds of formula (I) and (II) are shown in Tables 1 and 2 below:

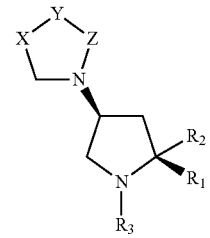

TABLE 1

| Compound | X | Y | Z | R$_1$ | R$_2$ | R$_3$ |
|---|---|---|---|---|---|---|
| 1 | —CH$_2$CH$_2$CH$_2$— | ![benzene] | absent | —CO$_2$H | H | —C(O)CH(phenyl)$_2$ |
| 2 | —CH$_2$CH$_2$CH$_2$— | ![fluorobenzene F] | absent | —CO$_2$H | H | —C(O)CH(phenyl)$_2$ |

TABLE 1-continued

| Compound | X | Y | Z | R₁ | R₂ | R₃ |
|---|---|---|---|---|---|---|
| 3 | —CH₂CH₂CH₂— | 3,4-dimethylphenyl with CH₃ | absent | —CO₂H | H | —C(O)CH(phenyl)₂ |
| 4 | —CH₂CH₂CH₂— | 3,4-dimethylphenyl with OCH₃ | absent | —CO₂H | H | —C(O)CH(phenyl)₂ |
| 5 | —CH₂CH₂CH₂— | 3,4-dimethylphenyl with F | absent | —CO₂H | H | —C(O)CH(phenyl)₂ |
| 6 | —CH₂CH₂CH₂— | 3,4-dimethylphenyl with Cl | absent | —CO₂H | H | —C(O)CH(phenyl)₂ |
| 7 | —CH₂CH₂—O— | 2,3-dimethylphenyl | absent | —CO₂H | H | —C(O)CH(phenyl)₂ |
| 8 | —CH₂CH₂—O— | 3,4-dimethylphenyl with F | absent | —CO₂H | H | —C(O)CH(phenyl)₂ |
| 9 | —CH₂CH₂—O— | 3,4-dimethylphenyl with F | absent | —CO₂H | H | —C(O)CH(phenyl)₂ |
| 10 | —CH₂—O—CH₂— | 2,3-dimethylphenyl | absent | —CO₂H | H | —C(O)CH(phenyl)₂ |
| 11 | —CH₂CH₂CH₂— | dimethylthiophene | absent | —CO₂H | H | —C(O)CH(phenyl)₂ |
| 12 | —CH₂CH₂CH₂— | dimethylpyridine | absent | —CO₂H | H | —C(O)CH(phenyl)₂ |

TABLE 1-continued

| Compound | X | Y | Z | R₁ | R₂ | R₃ |
|---|---|---|---|---|---|---|
| 13 | —CH₂CH₂CH₂CH₂— | 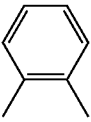 | absent | —CO₂H | H | —C(O)CH(phenyl)₂ |
| 14 | —CH₂CH₂— | 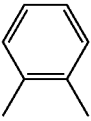 | absent | —CO₂H | H | —C(O)CH(phenyl)₂ |
| 15 | —CH₂CH₂CH₂— |  | absent | —CONH₂ | H | —C(O)CH(phenyl)₂ |
| 16 | —CH₂— | 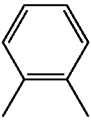 | —CH₂CH₂— | —CO₂H | H | —C(O)CH(phenyl)₂ |
| 17 | —CH₂N(CH₃)— | 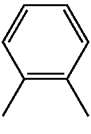 | —CH₂— | —CO₂H | H | —C(O)CH(phenyl)₂ |
| 18 | —CH₂CH₂— |  | —CH₂— | —CO₂H | H | —C(O)CH(phenyl)₂ |
| 19 | —CH₂O— |  | —CH₂— | —CO₂H | H | —C(O)CH(phenyl)₂ |
| 20 | absent | 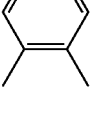 | —CH₂— | —CO₂H | H | —C(O)CH(phenyl)₂ |
| 21 | —CH₂CH₂—O— | 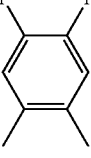 | absent | —CO₂H | H | —C(O)CH(phenyl)₂ |
| 27 | —CH₂CH₂CH₂— |  | absent | —CO₂H | H | —C(O)CH(phenyl)₂ |
| 29 | —CH₂— |  | absent | —CO₂H | H | —C(O)CH(phenyl)₂ |

TABLE 1-continued

| Compound | X | Y | Z | R₁ | R₂ | R₃ |
|---|---|---|---|---|---|---|
| 34 | —CH₂CH₂S(O)₂— | phenyl | absent | —CO₂H | H | —C(O)CH(phenyl)₂ |
| 35 | —CH₂CH₂CH₂— | phenyl | absent | tetrazolyl | H | —C(O)CH(phenyl)₂ |
| 36 | —CH₂CH₂—O— | 4,5-difluorophenyl | absent | —C(O)NHSO₂cyclopropyl | H | —C(O)CH(phenyl)₂ |
| 37 | —CH₂CH₂—O— | 5-fluorophenyl | absent | —C(O)NHSO₂cyclopropyl | H | —C(O)CH(phenyl)₂ |
| 38 | —CH₂CH₂—O— | 4-fluorophenyl | absent | —C(O)NHSO₂cyclopropyl | H | —C(O)CH(phenyl)₂ |
| 39 | —CH₂CH₂—O— | 4,5-difluorophenyl | absent | —C(O)NHSO₂N(CH₃)₂ | H | —C(O)CH(phenyl)₂ |
| 40 | —CH₂CH₂CH₂— | 4,5-difluorophenyl | absent | —C(O)NHSO₂N(CH₃)₂ | H | —C(O)CH(phenyl)₂ |
| 41 | —CH₂CH₂CH₂— | 4,5-difluorophenyl | absent | —C(O)NHSO₂cyclopropyl | H | —C(O)CH(phenyl)₂ |
| 43 | —CH₂CH₂CH₂— | phenyl | absent | —C(O)NHSO₂cyclopropyl | H | —C(O)CH(phenyl)₂ |
| 44 | —CH₂CH₂CH₂— | phenyl | absent | —C(O)NHSO₂N(CH₃)₂ | H | —C(O)CH(phenyl)₂ |

TABLE 1-continued

| Compound | X | Y | Z | R₁ | R₂ | R₃ |
|---|---|---|---|---|---|---|
| 45 | —CH₂— | benzene | —CH₂CH₂— | —CO₂H | H | —C(O)CH(phenyl)₂ |
| 30 | —CH₂CH₂CH₂— | benzene | absent | —CO₂H | —CH₃ | —C(O)CH(phenyl)₂ |
| 31 | —CH₂CH₂CH₂— | 4,5-difluorobenzene | absent | —CO₂H | —CH₃ | —C(O)CH(phenyl)₂ |
| 32 | —CH₂CH₂—O— | 4,5-difluorobenzene | absent | —CO₂H | —CH₃ | —C(O)CH(phenyl)₂ |
| 33 | —CH₂CH₂—O— | 4-fluorobenzene | absent | —CO₂H | —CH₃ | —C(O)CH(phenyl)₂ |
| 42b | —CH₂CH₂—O— | 4,5-difluorobenzene | absent | —C(O)NHSO₂cyclopropyl | —CH₃ | —C(O)CH(phenyl)₂ |

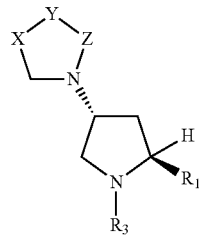

TABLE 2

| Compound | X | Y | Z | R₁ | R₂ | R₃ |
|---|---|---|---|---|---|---|
| 22 | —CH₂CH₂CH₂— | benzene | absent | —CO₂H | H | —C(O)CH(phenyl)₂ |

TABLE 2-continued

| Compound | X | Y | Z | R₁ | R₂ | R₃ |
|---|---|---|---|---|---|---|
| 23 | —CH$_2$CH$_2$CH$_2$— | (methylphenyl) | absent | —CO$_2$H | H | —C(O)CH(phenyl)$_2$ |
| 24 | —CH$_2$CH$_2$—O— | (difluorophenyl) | absent | —CO$_2$H | H | —C(O)CH(phenyl)$_2$ |
| 25 | —CH$_2$CH$_2$—O— | (fluorophenyl) | absent | —CO$_2$H | H | —C(O)CH(phenyl)$_2$ |
| 26 | —CH$_2$CH$_2$—O— | (phenyl) | absent | —CO$_2$H | H | —C(O)CH(phenyl)$_2$ |
| 28 | —CH$_2$CH$_2$CH$_2$— | (pyridyl) | absent | —CO$_2$H | H | —C(O)CH(phenyl)$_2$ |
| 42a | —CH$_2$CH$_2$—O— | (difluorophenyl) | absent | —C(O)NHSO$_2$cyclopropyl | —CH$_3$ | —C(O)CH(phenyl)$_2$ |

In particular embodiments, the compound of formulae (I) or (II) is one of compounds 1 to 9, 11 to 15, 18, 21 to 28, 30 to 41, 42a, 42b, 43, 44, and 45, more especially compounds 1, 2, 4 to 9, 11, 13, 14, 21 to 27, 30 to 34, 36 to 41, 42a, 42b, 43, 44 and 45, more especially compounds 1, 2, 4, 5, 7 to 9, 11, 13, 21, 22, 24 to 27, 30, 32 to 34, 36 to 38, 40, 42a and 43; even more especially compounds 1, 2, 7, 8, 9, 11, 21, 24 to 27, 30, 32, 36, 37 and 42a.

In some embodiments, the compounds of formula (I) are selective AT$_2$ receptor antagonists. In particular embodiments, the selective AT$_2$ receptor antagonists have an IC$_{50}$ at the AT$_2$ receptor of ≤100 nM and an IC$_{50}$ at the AT$_1$ receptor of >100,000 nM (10 μm).

The compounds of the invention are made by methods known in the art from commercially available starting materials.

For preparation of pyrrolidine derivatives, a suitable starting material is a suitably protected compound such as trans-4-hydroxy proline ethyl ester.

R$_2$ may be introduced by removing the hydrogen α— to the carboxylic acid or ester with a suitable base and alkylating with a suitable alkylating agent, such as an alkylhalide.

R$_3$ may be introduced either before or after the introduction of the nitrogen-containing heterocyclic group. If the nitrogen-containing heterocyclic group is introduced prior to the introduction of R$_3$, it may be necessary to protect the ring nitrogen bearing R$_3$ during the amination reaction. Suitable nitrogen protecting groups are known in the art, for example, in Greene & Wutz, Protective Groups in Organic Synthesis, Third Edition, John Wiley & Sons, 1999. A suitable nitrogen protecting group is t-butoxycarbonyl (Boc).

R$_3$ may be introduced by amide formation with a suitable carboxylic acid and the ring nitrogen. Amide formation is well known in the art and may involve the activation of the carboxylic acid, for example, the carboxy group is activated by formation of an acid chloride, carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCI), 1-hydroxybenzotriazole (HOBt), 1-hydroxy-7-azabenzotriazole (HOAt), ethyl-2-cyano-2-cyano-2-(hydroxyimino)acetate (Oxyma Pure), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chloro-1H-benzotriazol-1-yl)-1,1,3,3-tetramethyluronium tetrafluorophosphate (HCTU), O-benzotriazol-1-yl-N,N,N'N'-tetramethyluronium tetrafluoroborate (TBTU), (benzotriazol-1-yloxy) tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

In an alternative approach, $R_3$ may be introduced using an acid chloride such as $Ph_2CHC(O)Cl$, in the presence of base, such as $NaHCO_3$.

The N-containing heterocycle may be introduced by methods known in the art (for example, Reger et al., 2010). For example, 4-hydroxyproline derivatives, optionally with a carboxy protecting group, are treated with an anhydride such as triflic anhydride and a base such as diisopropylethylamine in dichloromethane, followed by treatment at $-30°$ C. with the desired N-containing heterocycle with warming to room temperature. Alternatively, the N-heterocycle (Ring G) may be introduced onto the pyrrolidine ring, before or after the introduction of $R_3$ and in which $R_1$ is optionally protected, where the pyrrolidine ring is a 4-oxopyrrolidine ring. The nitrogen heterocycle and oxo-pyrrolidine are combined and acidified, for example with acetic acid. Subsequently, a borate, such as tetramethylammonium triacetoxyhydroborate, is added under an inert atmosphere.

Subsequently, if necessary, $R_1$ carboxylic acid may be deprotected, for example with base such as LiOH, and $R_3$ may be introduced. $R_1$ and $R_3$ may also be further derivatized if required. For example, $R_1$ carboxylic acid may be reacted with a sulphonamide in the presence of an activating agent such as carbonyldiimidazole to produce an acyl sulphonamide or with a dimethyl sulfonyl urea in the presence of an activating agent such as a carbodiimide.

In some instances where the N-containing heterocyclic ring (Ring G) is not commercially available, this ring or group may be made by known methods. For example, substituted benzo[b]azepines may be prepared from an appropriately substituted 3,4-dihydronaphthalene-1-(2H)-one by reaction with hydroxylamine hydrochloride in the presence of pyridine to provide an oxime followed by reduction and rearrangement, for example with DIBAL and treatment with NaF and water. Substituted benzooxazepines may be prepared from appropriately substituted phenols by treatment with 3-halopropionic acid and cyclization in the presence of triflic acid to give a substituted chroman-4-one, which may be subsequently treated with hydroxylamine hydrochloride and DIBAL as described above to form the substituted benzo[b][1,4]oxazepine.

Methods of the Invention

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several anti-retroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barré syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barré syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. Examples of disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired neuronal conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired nerve conduction velocity is associated with Carpel Tunnel Syndrome, ulnar neuropathy, Guillian-Barré Syndrome, fascioscapulohumeral muscular dystrophy and spinal disc herneation.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance traveled. Sensory nerve conduction is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include alleviation of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal hypersensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®)), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include $5HT_3$ receptor antagonists such as alosetron (Lotronex®).

The $AT_2$ receptor antagonists of the invention are also useful in combination with radiotherapy in cancer patients.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurized pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions may comprise further active ingredients such as other therapies to treat neuropathic or inflammatory pain or the underlying condition that is causing the neuropathic or inflammatory pain or therapies to treat conditions characterized by neuronal hypersensitivity, disorders associated with aberrant nerve regeneration, proliferative disorders or disorders associated with an imbalance between bone resorption and bone formation.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations

AcOH: acetic acid; aq: aqueous; CDI: carbonyldiimidazole; DBU: 1,8-Diazabicyclo[5.4.0]undec-7-ene; DCE: 1,2-dichloroethane; DCC: N,N'-dicyclohexylcarbodiimide; DCM: dichloromethane; DIBAL-H: diisobutylaluminium hydride; DIPEA: diisopropylethylamine; DMAP: dimethylaminopyridine; DMF: N,N,-dimethylformamide; EDC: N-(3-Dimethylaminopropyl)-N'-ethylcarbodiimide hydrochloride; Et$_2$O: diethyl ether; EtOAc: ethyl acetate; (ES$^+$): electrospray ionization, positive mode; h: hours; HATU: (1-[bis(dimethylamino)methylene]-1H-1,2,3-triazolo[4,5-b]pyridinium 3-oxid hexafluorophosphate); HCl: hydrochloric acid; HPLC: high performance liquid chromatography; i-PrOH: isopropanol; LCMS: liquid chromatography-mass spectrometry; LiOH: lithium hydroxide; M: molar; mCPBA: meta-chloroperoxybenzoic acid; [M+H]$^+$: protonated molecular ion; MeCN: acetonitrile; MeOH: methanol; min: minutes; MgSO$_4$: magnesium sulfate; MS: mass spectrometry; m/z: mass-to-charge ratio; NaHCO$_3$: sodium bicarbonate; NaOH: sodium hydroxide; Na$_2$S$_2$O$_3$: sodium thiosulfate; NH$_3$: ammonia; NH$_4$Cl: ammonium chloride; RT: room temperature (ca. 20° C.); R$_t$: retention time; sat: saturated; SCX: strong cation exchange; TFA: trifluoroacetic acid; TFAA: trifluoroacetic anhydride; THF: tetrahydrofuran; UV: ultra-violet General Experimental Conditions All starting materials and solvents were obtained either from commercial sources or prepared according to literature procedure.

Silica gel chromatography was performed on an automated flash chromatography system, such as CombiFlash™ Companion or CombiFlash™ Rf system, using RediSep® Rf pre-packed silica (230-400 mesh, 40-63 μm) cartridges.

Analytical LCMS experiments to determine retention times and associated mass ions were performed using an Agilent 1200 series HPLC system coupled to an Agilent 6110 or 6120 series single quadrupole mass spectrometer running one of the analytical methods described below.

Preparative HPLC purifications were performed using a Waters X-Select™ CSH C18, 5 μm, 19×50 mm column using a gradient of 0.1% formic acid in MeCN and 0.1% aqueous formic acid. Fractions were collected following detection by either UV at a single wavelength measured by a variable wavelength detector on a Gilson 215 or a Varian PrepStar™ preparative HPLC, or by mass ion and UV detection at a single wavelength measured by a ZQ single quadrupole mass spectrometer, with positive and negative ion electrospray, and dual wavelength detection on a Waters FractionLynx™ LCMS.

SCX resin was purchased from Sigma Aldrich or Silicycle and washed with MeOH prior to use.

Analytical Methods

Method 1—Acidic 4 Min Method

Column: Waters X-Select CSH C18, 2.5 μm, 4.6×30 mm
Detection: UV at 254 nm (or 215 nm), MS ionization method—electrospray
Solvent A: Water/0.1% Formic acid
Solvent B: MeCN/0.1% Formic acid
Gradient:

| Time | % A | % B | Flow rate (mL/min) |
|---|---|---|---|
| 0.0 | 95 | 5 | 2.5 |
| 3.0 | 5 | 95 | 2.5 |
| 3.01 | 5 | 95 | 4.5 |
| 3.5 | 5 | 95 | 4.5 |
| 3.6 | 95 | 5 | 3.5 |
| 4.0 | 95 | 5 | 2.5 |

Method 2—Acidic 15 Min Method

Column: Waters X-Select CSH C18, 2.5 μm, 4.6×30 mm
Detection: UV at 254 nm (or 215 nm), MS ionization method—electrospray
Solvent A: Water/0.1% Formic acid
Solvent B: MeCN/0.1% Formic acid
Gradient:

| Time | % A | % B | Flow rate (mL/min) |
|---|---|---|---|
| 0.0 | 95.0 | 5.0 | 2.5 |
| 14.0 | 5.0 | 95.0 | 2.5 |
| 14.01 | 5.0 | 95.0 | 4.5 |
| 14.50 | 5.0 | 95.0 | 4.5 |
| 14.60 | 95.0 | 5.0 | 3.5 |
| 15.00 | 95.0 | 5.0 | 2.5 |

Example 1: Compound 1 (2S,4S)-1-(2,2-Diphenylacetyl)-4-(2,3,4,5-tetrahydro-1H-benzo[b]azepin-1-yl)pyrrolidine-2-carboxylic acid

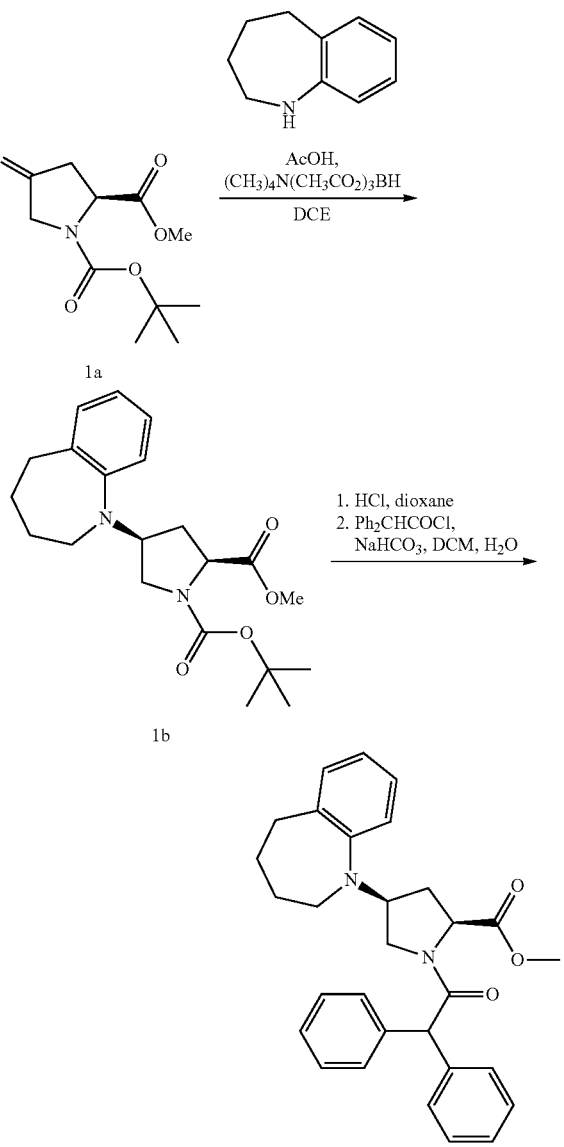

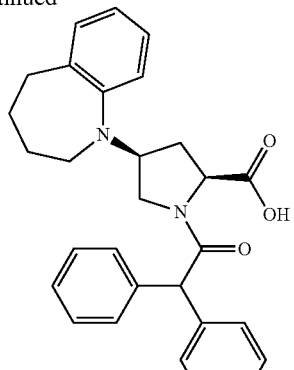

1

Procedure for the Preparation of 1b

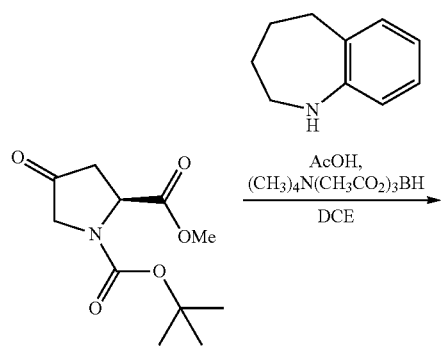

and the residue was purified by silica gel chromatography (40 g, 0-100% EtOAc/isohexane) to afford (2S,4S)-1-tert-butyl 2-methyl 4-(2,3,4,5-tetrahydro-1H-benzo[b]azepin-1-yl)pyrrolidine-1,2-dicarboxylate 1b (570 mg, 70%) as a colourless gum: m/z 375 [M+H]⁺ (ES⁺) at $R_t$ 2.79 min (Method 1).

Procedure for the Preparation of 1c

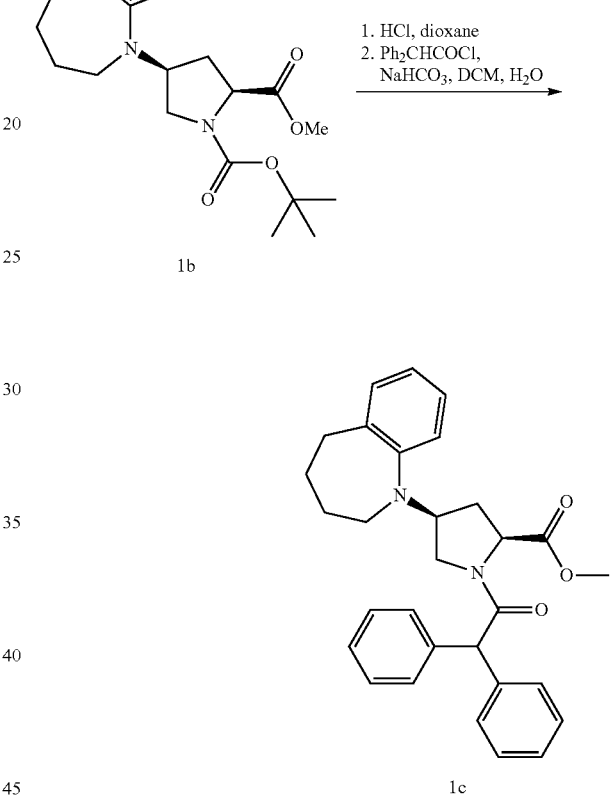

A solution of 2,3,4,5-tetrahydro-1H-benzo[b]azepine (300 mg, 2.05 mmol) in 1,2-dichloroethane (5 mL) was added to a solution of (S)-1-tert-butyl 2-methyl 4-oxopyrrolidine-1,2-dicarboxylate 1a (500 mg, 2.05 mmol) in 1,2-dichloroethane (5 mL) whilst stirring at RT under an atmosphere of nitrogen. After 5 min AcOH (0.23 mL, 4.1 mmol) was added. After 45 min tetramethylammonium triacetoxyhydroborate (650 mg, 2.5 mmol) was added in one portion and the mixture was stirred at RT for 18 h. The mixture was diluted with DCM (40 mL) then washed with saturated aqueous NaHCO₃ (40 mL). The aqueous solution was extracted with DCM (20 mL) then the combined organic solutions were washed with saturated brine (20 mL), dried over Na₂SO₄ and filtered. The solvent was removed in vacuo HCl in dioxane (4 M, 5.4 mL, 21.6 mmol) was added to a solution of (2S,4S)-1-tert-butyl 2-methyl 4-(2,3,4,5-tetrahydro-1H-benzo[b]azepin-1-yl)pyrrolidine-1,2-dicarboxylate 1b (540 mg, 1.4 mmol) in 1,4-dioxane (6 mL). The solution was stirred at RT for 5 h then stored at 4° C. for 16 h. The mixture was concentrated in vacuo and residual solvent co-evaporated with toluene (2×3 mL) to obtain a pale yellow hygroscopic solid. The solid was suspended in DCM (4.5 mL) and NaHCO₃ (300 mg, 3.6 mmol) and water (4.5 mL) were added. The mixture was stirred under nitrogen with ice-bath cooling and 2,2-diphenylacetyl chloride (370 mg, 1.4 mmol) was added. The ice-bath was removed and the mixture was warmed to RT and stirred for 90 min. The biphasic mixture was separated, the organic solution was concentrated in vacuo and the residue was purified by silica gel chromatography (40 g, 0-50% EtOAc/isohexane) to afford (2S,4S)-methyl 1-(2,2-diphenylacetyl)-4-(2,3,4,5-tetrahydro-1H-benzo[b]azepin-1-yl)pyrrolidine-2-carboxylate 1c (450 mg, 65%) as a white foamy solid: m/z 469 [M+H]⁺ (ES⁺) at $R_t$ 2.92 min (Method 1).

Procedure for the Preparation of Compound 1

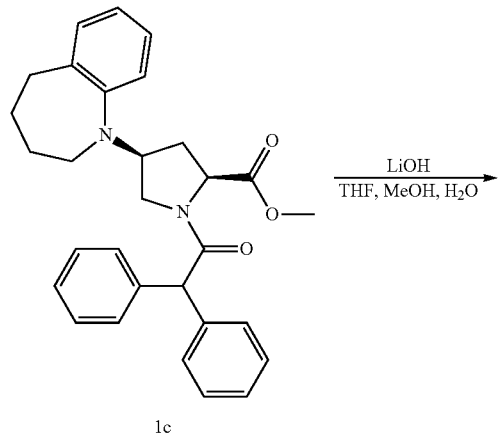

1c

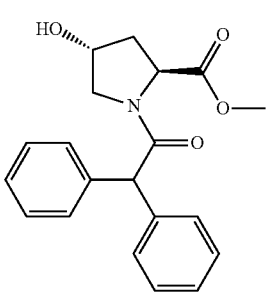

2b

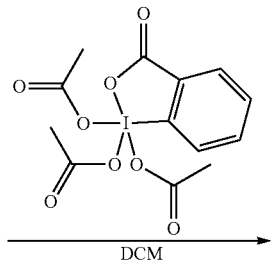

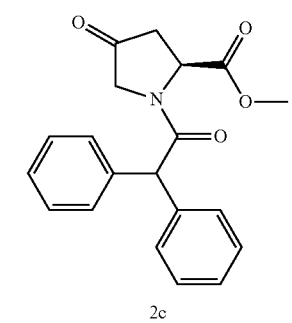

2c

1

Water (0.75 mL) was added to a stirred suspension of (2S,4S)-methyl 1-(2,2-diphenylacetyl)-4-(2,3,4,5-tetrahydro-1H-benzo[b]azepin-1-yl)pyrrolidine-2-carboxylate 1c (440 mg, 0.94 mmol) and LiOH (34 mg, 1.4 mmol) in a mixture of THF (3 mL) and MeOH (0.75 mL). The mixture was stirred at RT for 4.5 h then stood at 4° C. for 18 h. AcOH (2 mL) was added and the mixture was loaded onto a column of SCX. The column was washed with MeOH, then the product was eluted with 1% $NH_3$ in MeOH and the solution was concentrated in vacuo. The residue was purified by preparative HPLC ((0.1% formic acid) 35-65% MeCN in Water) to afford (2S,4S)-1-(2,2-diphenylacetyl)-4-(2,3,4,5-tetrahydro-1H-benzo[b]azepin-1-yl)pyrrolidine-2-carboxylic acid as a white solid 1 (200 mg, 46%): m/z 455 [M+H]$^+$ (ES$^+$), 453 [M−H]$^−$ (ES$^−$) at $R_t$ 7.37 min (Method 2).

Example 2: Compound 2 (2S,4S)-1-(2,2-Diphenylacetyl)-4-(8-fluoro-2,3,4,5-tetrahydro-1H-benzo[b]azepin-1-yl)pyrrolidine-2-carboxylic acid

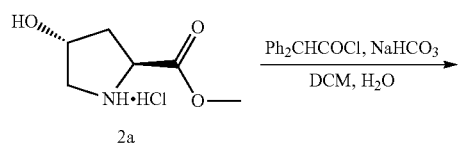

2a

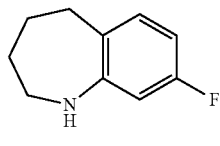

2e

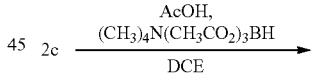

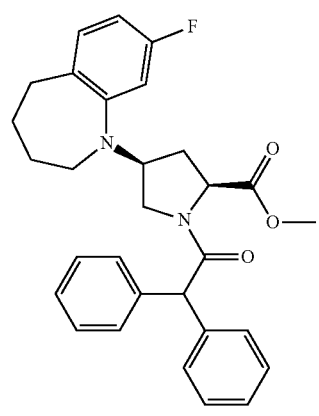

2d

-continued

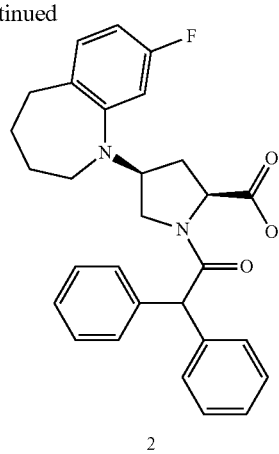

2

Procedure for the Preparation of 2b

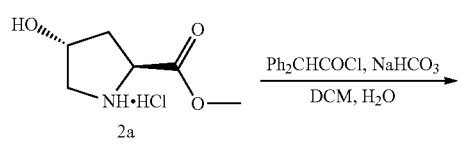

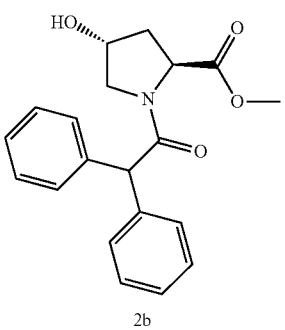

2b 2,2-Diphenylacetyl chloride (12 g, 46 mmol) was added to a stirred mixture of (2S,4R)-methyl 4-hydroxypyrrolidine-2-carboxylate.HCl 2a (10 g, 55 mmol) and NaHCO$_3$ (9.6 g, 115 mmol) in water (200 mL) and DCM (200 mL) under an atmosphere of nitrogen whilst chilling with iced water. The biphasic mixture was allowed to warm to RT and stirred for 1.5 h. The layers were separated and the organic phase was washed with water (150 mL) and saturated brine (150 mL). The organic solution was dried over MgSO$_4$, filtered then concentrated in vacuo to afford a pale yellow gum. The product was purified by silica gel chromatography (220 g, 0-70% EtOAc/isohexane) to afford (2S,4R)-methyl 1-(2,2-diphenylacetyl)-4-hydroxypyrrolidine-2-carboxylate 2b (12 g, 76%) as a white solid: m/z 340 [M+H]$^+$ (ES$^+$) at R$_t$ 1.79 min (Method 1).

Procedure for the Preparation of 2c

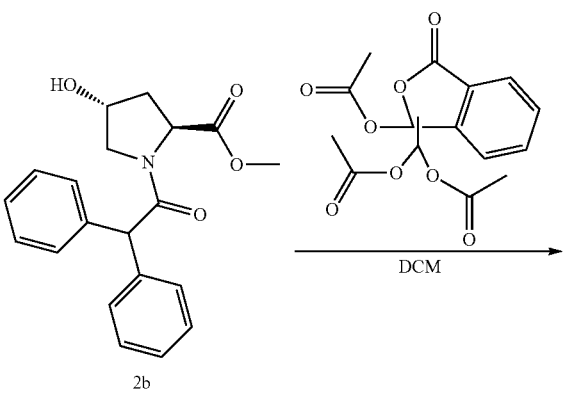

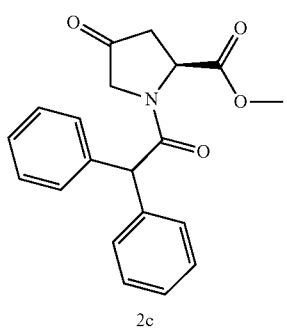

2c

To a solution of (2S,4R)-methyl 1-(2,2-diphenylacetyl)-4-hydroxypyrrolidine-2-carboxylate 2b (5.2 g, 15 mmol) in DCM (150 mL) at 0° C. was added Dess-Martin Periodinane (9.7 g, 23 mmol). The reaction mixture was then warmed to RT and stirred for 4 h. DCM (100 mL) was added followed by 1 M aqueous citric acid solution (100 mL) and the layers were separated. The organic layer was washed with water (100 mL) and saturated brine (100 mL), dried over MgSO$_4$ and concentrated in vacuo to give a white foamy solid. The product was purified by silica gel chromatography (80 g, 0-50% EtOAc/isohexane) to afford (S)-methyl 1-(2,2-diphenylacetyl)-4-oxopyrrolidine-2-carboxylate 2c (4.5 g, 86%) as a white solid: m/z 338 [M+H]$^+$ (ES$^+$) at R$_t$ 2.04 min (Method 1).

Procedure for the Preparation of 2d

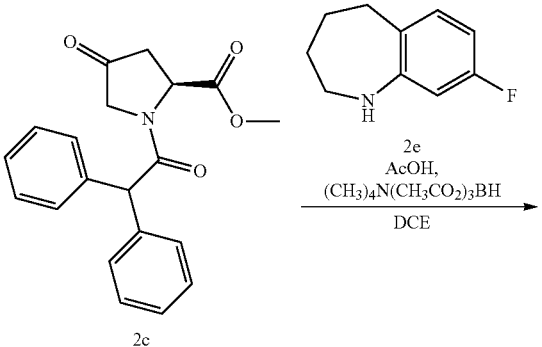

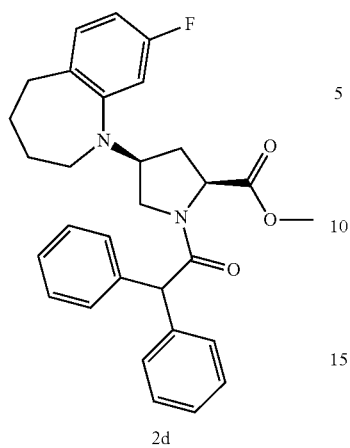

2d

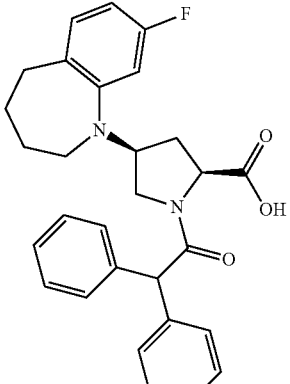

2

A solution of 8-fluoro-2,3,4,5-tetrahydro-1H-benzo[b]azepine 2e (100 mg, 0.6 mmol) in DCE (1.5 mL) was added to a stirred solution of (S)-methyl 1-(2,2-diphenylacetyl)-4-oxopyrrolidine-2-carboxylate 2c (200 mg, 0.6 mmol) in DCE (1.5 mL) whilst stirring at RT. After 5 min AcOH (68 µL, 1.2 mmol) was added. After a further 25 min tetramethylammonium triacetoxyhydroborate (190 mg, 0.71 mmol) was added in one portion and the reaction was placed under nitrogen and stirred at RT for 20 h. The mixture was diluted with DCM (20 mL) and washed with NaHCO₃ (15 mL). The aqueous solution was reextracted with DCM (10 mL) then the combined organic layers washed with saturated brine (10 mL), dried over Na₂SO₄ and filtered. The organic solution was concentrated in vacuo and the residue was purified by silica gel chromatography (12 g, 0-60% EtOAc/isohexane) to afford (2S,4S)-methyl 1-(2,2-diphenylacetyl)-4-(8-fluoro-2,3,4,5-tetrahydro-1H-benzo[b]azepin-1-yl)pyrrolidine-2-carboxylate 2d (100 mg, 34%) as a colourless gum: m/z 487 [M+H]⁺ (ES⁺) at R$_t$ 3.03 min (Method 1).

Procedure for the Preparation of Compound 2

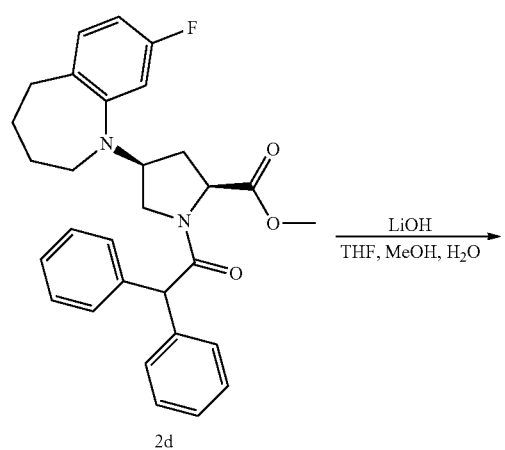

Water (0.5 mL) added to a stirred suspension of (2S,4S)-methyl 1-(2,2-diphenylacetyl)-4-(8-fluoro-2,3,4,5-tetrahydro-1H-benzo[b]azepin-1-yl)pyrrolidine-2-carboxylate 2d (90 mg, 0.2 mmol) and LiOH (7 mg, 0.3 mmol) in THF (2 mL) and MeOH (0.5 mL) and the mixture was stirred at RT for 20 h. The mixture was concentrated in vacuo and the residue was dissolved in MeOH and AcOH (50 µL) for purification by SCX. The SCX column was washed with MeOH, then the product was eluted with 1% NH₃/MeOH. The solution was concentrated in vacuo and the residue was purified by silica gel chromatography (4 g, 0-70% (1% AcOH/EtOAc)/isohexane) to afford (2S,4S)-1-(2,2-diphenylacetyl)-4-(8-fluoro-2,3,4,5-tetrahydro-1H-benzo[b]azepin-1-yl)pyrrolidine-2-carboxylic acid 2 (51 mg, 55%) as a white solid: m/z 473 [M+H]⁺ (ES⁺) at R$_t$ 7.91 min (Method 2).

Procedure for the Preparation of 2e

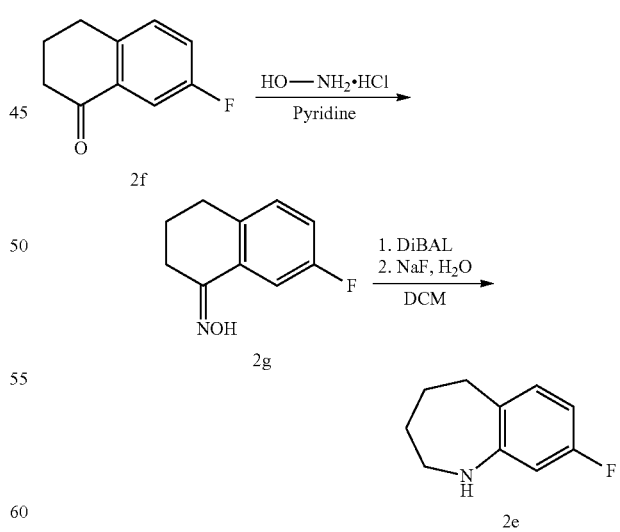

Step 1: Hydroxylamine hydrochloride (0.42 g, 6.1 mmol) was added to a stirred solution of 7-fluoro-3,4-dihydronaphthalen-1(2H)-one 2f (0.5 g, 3 mmol) in pyridine (5 mL). The mixture was stirred at RT for 18 h and then concentrated in vacuo. The residue was partitioned between EtOAc (25 mL)

and water (30 mL). The aqueous layer was reextracted with EtOAc (25 mL) then the combined organic layers were washed with saturated brine (25 mL), dried over MgSO$_4$ and filtered. The solution was concentrated in vacuo and the residue was purified by silica gel chromatography (12 g, 0-100% EtOAc/isohexane) to afford 7-fluoro-3,4-dihydronaphthalen-1(2H)-one oxime 2g (490 mg, 89%) as a white solid: m/z 180 [M+H]$^+$ (ES$^+$) at R$_t$ 1.94 min (Method 1).

Step 2: DIBAL-H (1M in hexane) (15.7 mL, 15.7 mmol) was added portionwise to a stirred solution of 7-fluoro-3,4-dihydronaphthalen-1(2H)-one oxime 2g (470 mg, 2.6 mmol) in DCM (20 mL) over 15 min under an atmosphere of nitrogen and whilst chilling with iced water. After 5 min the solution was warmed to RT and stirred for 3 h. The mixture was cooled with iced water and powdered NaF (3 g) was added, followed by water (1.5 mL) cautiously. The suspension was stirred for 30 min then filtered through celite which was then washed with EtOAc. The filtrate was concentrated in vacuo and the residue was purified by silica gel chromatography (12 g, 0-15% EtOAc/isohexane) to afford 8-fluoro-2,3,4,5-tetrahydro-1H-benzo[b]azepine 2e (270 mg, 59%) as a white solid: m/z 166 [M+H]$^+$ (ES$^+$) at R$_t$ 0.98 min (Method 1).

Example 3: Compound 8 (2S,4S)-1-(2,2-Diphenylacetyl)-4-(7-fluoro-3,4-dihydrobenzo[b][1,4]oxazepin-5(2H)-yl)pyrrolidine-2-carboxylic acid

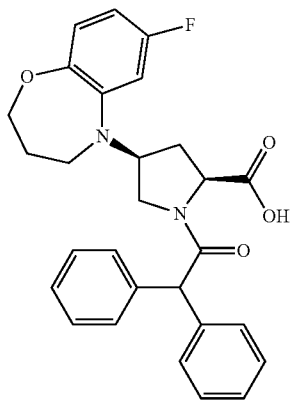 [SMILES: O=C(O)[C@@H]1C[C@H](N2CCCOc3ccc(F)cc32)CN1C(=O)C(c1ccccc1)c1ccccc1]

(2S,4S)-1-(2,2-Diphenylacetyl)-4-(7-fluoro-3,4-dihydrobenzo[b][1,4]oxazepin-5(2H)-yl)pyrrolidine-2-carboxylic acid 8 (19 mg, 49% for final step) was prepared in essentially the same manner as for Compound 2 (Example 2) except that 7-fluoro-2,3,4,5-tetrahydrobenzo[b][1,4]oxazepine (prepared in the same manner as 2e) was used instead of 8-fluoro-2,3,4,5-tetrahydro-1H-benzo[b]azepine 2e in step 3: m/z 475 [M+H]$^+$ (ES$^+$), 473 (M−H)$^-$ (ES$^-$) at R$_t$ 6.93 min (Method 1).

Example 4: Compound 9 (2S,4S)-1-(2,2-diphenylacetyl)-4-(8-fluoro-3,4-dihydrobenzo[b][1,4]oxazepin-5(2H)-yl)pyrrolidine-2-carboxylic acid

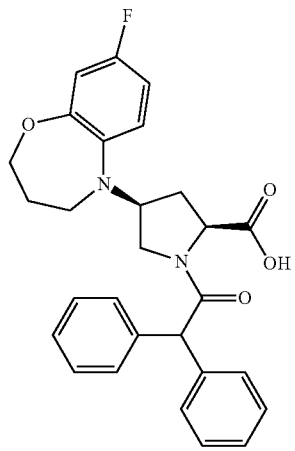 [SMILES: O=C(O)[C@@H]1C[C@H](N2CCCOc3cc(F)ccc32)CN1C(=O)C(c1ccccc1)c1ccccc1]

(2S,4S)-1-(2,2-diphenylacetyl)-4-(8-fluoro-3,4-dihydrobenzo[b][1,4]oxazepin-5 (2H)-yl)pyrrolidine-2-carboxylic acid 9 (51 mg, 64% for final step) was prepared in essentially the same manner as for Compound 2 (Example 2) except that 8-fluoro-2,3,4,5-tetrahydrobenzo[b][1,4]oxazepine (prepared in the same manner as 2e) was used instead of 8-fluoro-2,3,4,5-tetrahydro-1H-benzo[b]azepine 2e in step 3: m/z 475 [M+H]$^+$ (ES$^+$), 473 (M−H)$^-$ (ES$^-$) at R$_t$ 6.78 min (Method 2).

Example 5: Compound 7 (2S,4S)-4-(3,4-dihydrobenzo[b][1,4]oxazepin-5(2H)-yl)-1-(2,2-diphenylacetyl)pyrrolidine-2-carboxylic acid

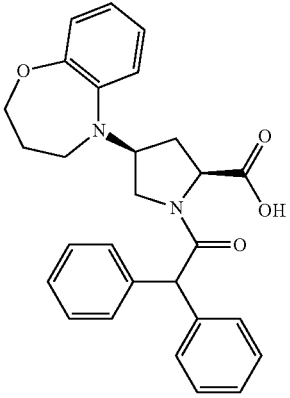 [SMILES: O=C(O)[C@@H]1C[C@H](N2CCCOc3ccccc32)CN1C(=O)C(c1ccccc1)c1ccccc1]

(2S,4S)-4-(3,4-dihydrobenzo[b][1,4]oxazepin-5(2H)-yl)-1-(2,2-diphenylacetyl)pyrrolidine-2-carboxylic acid 7 (56 mg, 89% for final step) was prepared in essentially the same manner as for Compound 2 (Example 2) except that 2,3,4,5-tetrahydrobenzo[b][1,4]oxazepine was used instead of 8-fluoro-2,3,4,5-tetrahydro-1H-benzo[b]azepine 2e in step 3: m/z 457 [M+H]$^+$ (ES$^+$), 455 (M−H)$^-$ (ES$^-$) at R$_t$ 6.30 min (Method 2).

Example 6: Compound 21 (2S,4S)-4-(7,8-difluoro-3,4-dihydrobenzo[b][1,4]oxazepin-5(2H)-yl)-1-(2,2-diphenylacetyl)pyrrolidine-2-carboxylic acid

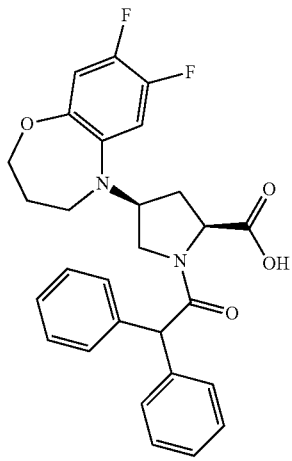 [SMILES: O=C(O)[C@@H]1C[C@H](N2CCCOc3cc(F)c(F)cc32)CN1C(=O)C(c1ccccc1)c1ccccc1]

(2S,4S)-4-(7,8-difluoro-3,4-dihydrobenzo[b][1,4]oxazepin-5(2H)-yl)-1-(2,2-diphenylacetyl)pyrrolidine-2-carboxylic acid 21 (88 mg, 63% for final step) was prepared in essentially the same manner as for Compound 2 (Example 2) except that 7,8-difluoro-2,3,4,5-tetrahydrobenzo[b][1,4]oxazepine 21e was used instead of 8-fluoro-2,3,4,5-tetrahydro-1H-benzo[b]azepine 2e in step 3: m/z 493 [M+H]$^+$ (ES$^+$) at R$_t$ 7.65 min (Method 2).

Procedure for the Preparation of Compound 21e

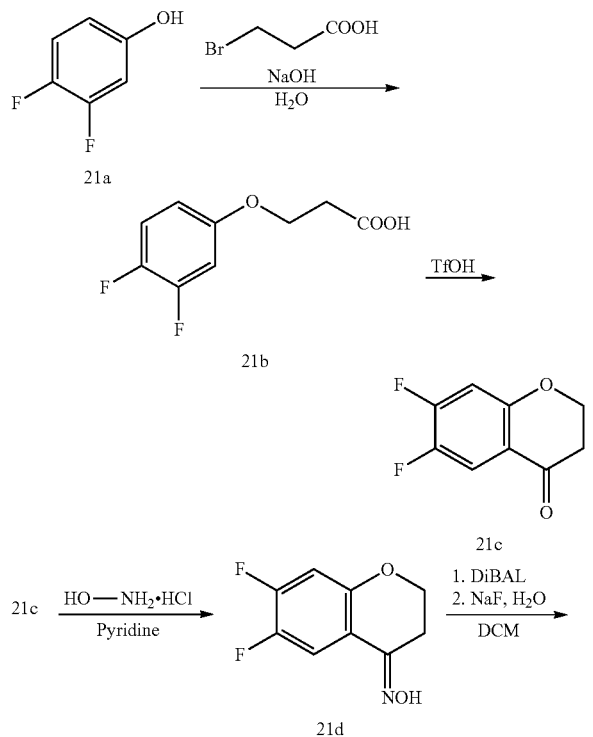

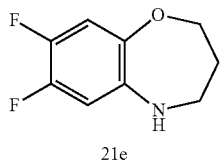

Step 1: A mixture of 3,4-difluorophenol 21a (5.0 g, 38 mmol), 3-bromopropanoic acid (6.5 g, 42 mmol) and NaOH (3.1 g, 77 mmol) in water (50 mL) was refluxed for 4.5 h. After cooling to RT, the pH of the reaction mixture was adjusted to ~2 by the addition of 3M HCl and the product was extracted with EtOAc (200 mL). The organic solution was washed with saturated brine, dried over MgSO$_4$ and filtered. The solution was concentrated in vacuo and the residue was purified by silica gel chromatography (80 g, 0-60% EtOAc/isohexane) to afford 3-(3,4-difluorophenoxy)propanoic acid 21b (1.9 g, 22%) as a cream solid: m/z 201 [M−H]$^−$ (ES$^−$) at R$_t$ 1.71 min (Method 1).

Step 2: A mixture of 3-(3,4-difluorophenoxy)propanoic acid 21b (0.50 g, 2.5 mmol) and triflic acid (5.0 mL, 56 mmol) was stirred at RT for 18 h. After this time, the reaction mixture was poured in to iced water (30 mL). The resultant solid was collected by filtration to yield 6,7-difluorochroman-4-one 21c (370 mg, 81%) as a white solid: m/z 185 [M+H]$^+$ (ES$^+$) at R$_t$ 1.76 min (Method 1).

Step 3: Hydroxylamine hydrochloride (0.3 g, 4 mmol) was added to a stirred solution of 6,7-difluorochroman-4-one 21c (0.4 g, 2 mmol) in pyridine (4 mL). The mixture was stirred at RT for 20 h and then concentrated in vacuo. The residue was partitioned between EtOAc (25 mL) and water (30 mL). The aqueous layer was re-extracted with EtOAc (25 mL) then the combined organic layers were washed with saturated brine (25 mL), dried over MgSO$_4$ and filtered. The solution was concentrated in vacuo and the residue was purified by silica gel chromatography (12 g, 0-50% EtOAc/isohexane) to afford 6,7-difluorochroman-4-one oxime 21d (275 mg, 69%) as a white solid: m/z 200 [M+H]$^+$ (ES$^+$) at R$_t$ 1.85 min (Method 1).

Step 4: DIBAL-H (1M in hexane) (8.1 mL, 8.1 mmol) was added portionwise to a stirred solution of 6,7-difluorochroman-4-one oxime 21d (270 mg, 21.4 mmol) in DCM (12 mL) over 10 min under an atmosphere of nitrogen and whilst chilling with iced water. After 5 min the solution was warmed to RT and stirred for 5 h. The mixture was cooled with iced water and powdered NaF (2 g) was added, followed by water (1 mL) cautiously. The suspension was stirred for 30 min then filtered through celite which was then washed with EtOAc. The filtrate was concentrated in vacuo and the residue was purified by silica gel chromatography (12 g, 0-50% EtOAc/isohexane) to afford 7,8-difluoro-2,3,4,5-tetrahydrobenzo[b][1,4]oxazepine 21e (170 mg, 66%) as a white solid: m/z 186 [M+H]$^+$ (ES$^+$) at R$_t$ 1.56 min (Method 1).

Example 7: Compound 22 (2S,4R)-1-(2,2-diphenylacetyl)-4-(2,3,4,5-tetrahydro-1H-benzo[b]azepin-1-yl)pyrrolidine-2-carboxylic acid

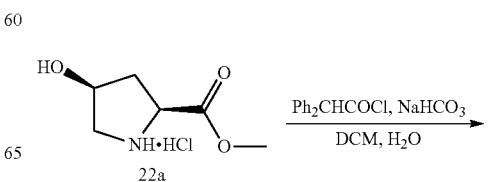

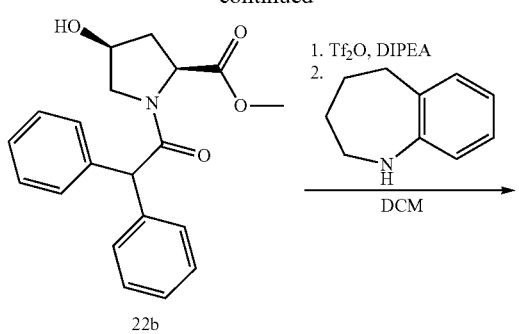

22b

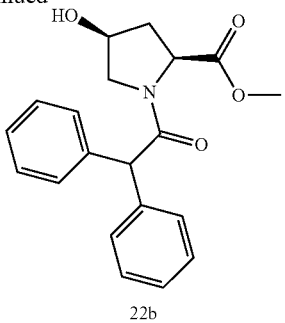

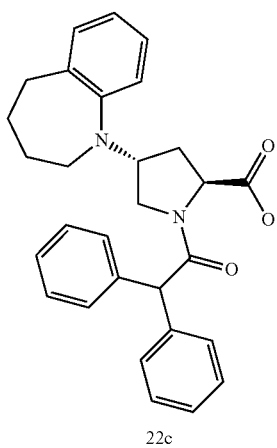

22c

22c  $\xrightarrow{\text{LiOH}}$  
THF, MeOH, H$_2$O

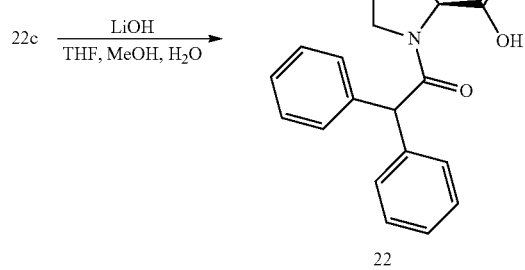

22

Procedure for the Preparation of Compound 22b

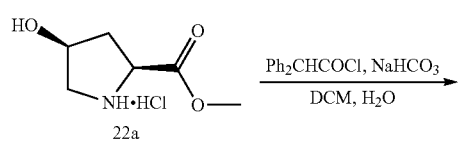

22a  $\xrightarrow{\text{Ph}_2\text{CHCOCl, NaHCO}_3}$  
DCM, H$_2$O

To a bi-phasic mixture of methyl (2S,4S)-4-hydroxypyrrolidine-2-carboxylate hydrochloride 22a (1.1 g, 6.2 mmol) and NaHCO$_3$ (2.1 g, 25 mmol) in water (5 mL) and DCM (5 mL) was added 2,2-diphenylacetyl chloride (1.4 g, 6.2 mmol) at 0° C. The reaction mixture was warmed to RT and stirred for 16 h. The layers were separated and organic solution was washed with saturated brine (3×10 mL), dried over MgSO$_4$ and filtered. The solution was concentrated in vacuo and the residue was purified by silica gel chromatography (24 g, 0-100% EtOAc/isohexane) to afford (2S,4S)-methyl 1-(2,2-diphenylacetyl)-4-hydroxypyrrolidine-2-carboxylate 22b (1.75 g, 82%) as a colourless oil: m/z 340 [M+H]$^+$ (ES$^+$) at R$_t$ 1.80 min (Method 1).

Procedure for the Preparation of Compound 22c

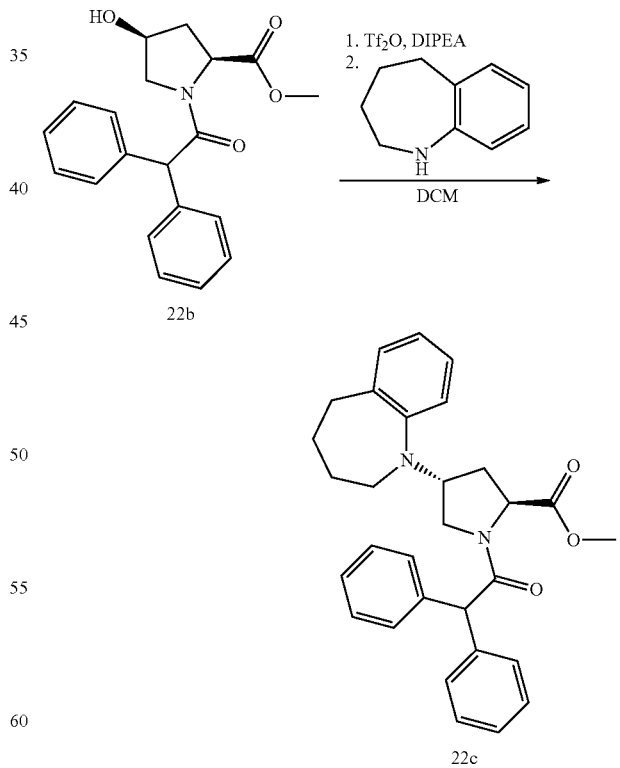

Trifluoromethanesulfonic anhydride (125 µl, 0.743 mmol) was added to a stirred mixture of (2S,4S)-methyl 1-(2,2-diphenylacetyl)-4-hydroxypyrrolidine-2-carboxylate 22b (210 mg, 0.62 mmol) and DIPEA (160 µl, 0.93 mmol) in DCM (1.5 mL) at −78° C. The mixture was warmed to −30° C. and a solution of 2,3,4,5-tetrahydro-1H-benzo[b]azepine (140 mg, 0.93 mmol) in DCM (0.5 mL) was added. The mixture was warmed to RT and stirred for 16 h. Silica gel was added and the mixture was concentrated in vacuo and purified by silica gel chromatography (12 g, 0-50% EtOAc/isohexane) to afford (2S,4R)-methyl 1-(2,2-diphenylacetyl)-4-(2,3,4,5-tetrahydro-1H-benzo[b]azepin-1-yl)pyrrolidine-2-carboxylate 22c (40 mg, 13%) as a white solid: m/z 469 [M+H]$^+$ (ES$^+$) at R$_t$ 2.95 min (Method 1).

Procedure for the Preparation of Compound 22

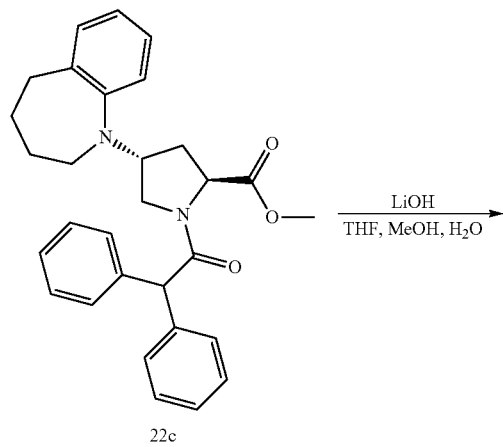

22c

LiOH
THF, MeOH, H$_2$O

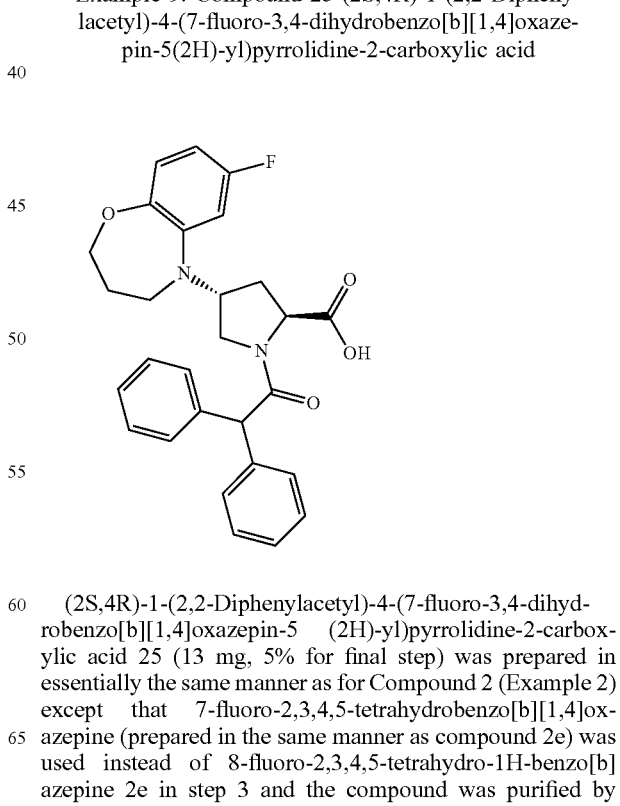

22

LiOH (6.1 mg, 0.26 mmol) was added to a stirred solution of (2S,4R)-methyl 1-(2,2-diphenylacetyl)-4-(2,3,4,5-tetrahydro-1H-benzo[b]azepin-1-yl)pyrrolidine-2-carboxylate 22c (40 mg, 0.08 mmol) in THF (1 mL) and water (0.5 mL). The mixture was stirred at RT for 16 h, then acidified by the addition of AcOH (5 mL) and loaded on to SCX. The SCX column was washed with i-PrOH and the product was eluted with 1% NH$_3$ in MeOH. The solution was concentrated in vacuo to give (2S,4R)-1-(2,2-diphenylacetyl)-4-(2,3,4,5-tetrahydro-1H-benzo[b]azepin-1-yl)pyrrolidine-2-carboxylic acid 22 (28 mg, 71%) as a white solid: m/z 455 [M+H]$^+$ (ES$^+$), 453 (M−H)$^-$ (ES$^-$) at R$_t$ 11.37 min (Method 2).

Example 8: Compound 24 (2S,4R)-4-(7,8-Difluoro-3,4-dihydrobenzo[b][1,4]oxazepin-5(2H)-yl)-1-(2,2-diphenylacetyl)pyrrolidine-2-carboxylic acid

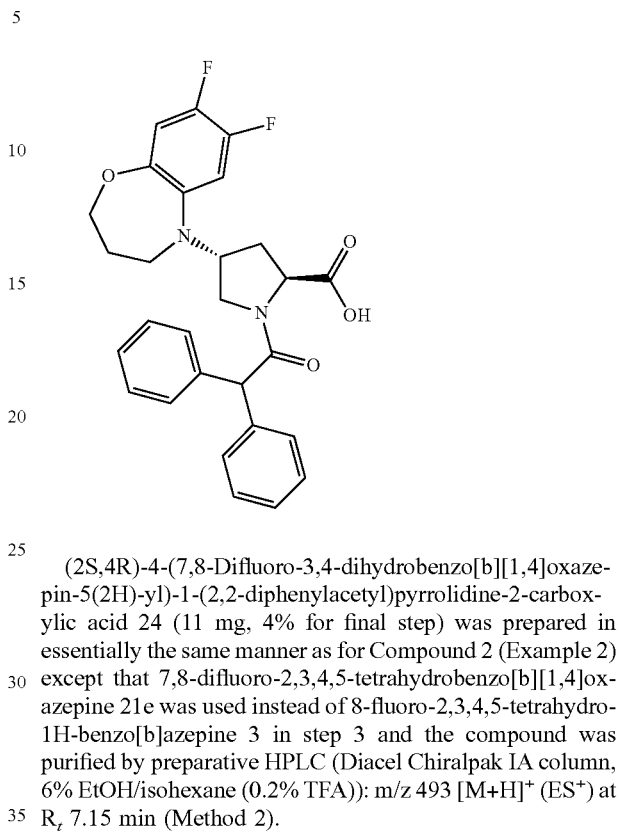

(2S,4R)-4-(7,8-Difluoro-3,4-dihydrobenzo[b][1,4]oxazepin-5(2H)-yl)-1-(2,2-diphenylacetyl)pyrrolidine-2-carboxylic acid 24 (11 mg, 4% for final step) was prepared in essentially the same manner as for Compound 2 (Example 2) except that 7,8-difluoro-2,3,4,5-tetrahydrobenzo[b][1,4]oxazepine 21e was used instead of 8-fluoro-2,3,4,5-tetrahydro-1H-benzo[b]azepine 3 in step 3 and the compound was purified by preparative HPLC (Diacel Chiralpak IA column, 6% EtOH/isohexane (0.2% TFA)): m/z 493 [M+H]$^+$ (ES$^+$) at R$_t$ 7.15 min (Method 2).

Example 9: Compound 25 (2S,4R)-1-(2,2-Diphenylacetyl)-4-(7-fluoro-3,4-dihydrobenzo[b][1,4]oxazepin-5(2H)-yl)pyrrolidine-2-carboxylic acid (2S,4R)-1-(2,2-Diphenylacetyl)-4-(7-fluoro-3,4-dihydrobenzo[b][1,4]oxazepin-5 (2H)-yl)pyrrolidine-2-carboxylic acid 25 (13 mg, 5% for final step) was prepared in essentially the same manner as for Compound 2 (Example 2) except that 7-fluoro-2,3,4,5-tetrahydrobenzo[b][1,4]oxazepine (prepared in the same manner as compound 2e) was used instead of 8-fluoro-2,3,4,5-tetrahydro-1H-benzo[b]azepine 2e in step 3 and the compound was purified by preparative HPLC (Diacel Chiralpak IA column, 6% EtOH/isohexane (0.2% TFA)): m/z 475 [M+H]⁺ (ES⁺) at $R_t$ 6.87 min (Method 2).

Example 10: Compound 26 (2S,4R)-4-(3,4-Dihydrobenzo[b][1,4]oxazepin-5(2H)-yl)-1-(2,2-diphenylacetyl)pyrrolidine-2-carboxylic acid

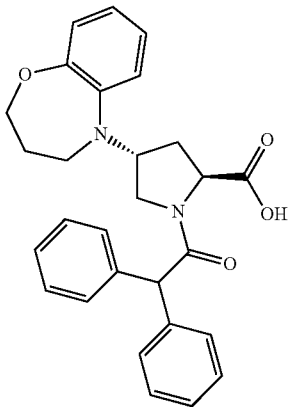 [SMILES: O=C(O)[C@@H]1C[C@@H](N2CCCOc3ccccc32)CN1C(=O)C(c1ccccc1)c1ccccc1]

(2S,4R)-4-(3,4-Dihydrobenzo[b][1,4]oxazepin-5(2H)-yl)-1-(2,2-diphenylacetyl) pyrrolidine-2-carboxylic acid 26 (15 mg, 5% for final step) was prepared in essentially the same manner as for Compound 2 (Example 2) except that 2,3,4,5-tetrahydrobenzo[b][1,4]oxazepine was used instead of 8-fluoro-2,3,4,5-tetrahydro-1H-benzo[b]azepine 2e in step 3 and the compound was purified by preparative HPLC (Diacel Chiralpak IA column, 6% EtOH/isohexane (0.2% TFA)): m/z 457 [M+H]⁺ (ES⁺) at $R_t$ 6.59 min (Method 2).

Example 11: Compound 27 (2S,4S)-4-(7,8-Difluoro-2,3,4,5-tetrahydro-1H-benzo[b]azepin-1-yl)-1-(2,2-diphenylacetyl)pyrrolidine-2-carboxylic acid

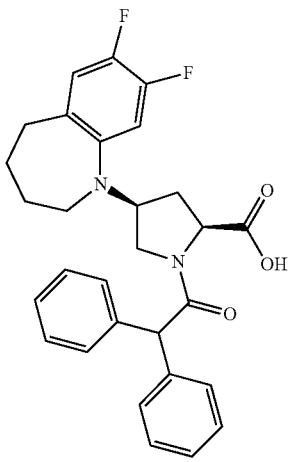 [SMILES: O=C(O)[C@@H]1C[C@H](N2CCCCc3cc(F)c(F)cc32)CN1C(=O)C(c1ccccc1)c1ccccc1]

(2S,4S)-4-(7,8-Difluoro-2,3,4,5-tetrahydro-1H-benzo[b]azepin-1-yl)-1-(2,2-diphenylacetyl)pyrrolidine-2-carboxylic acid 27 (12 mg, 55% for final step) was prepared in essentially the same manner as for Compound 2 (Example 2) except that 7,8-difluoro-2,3,4,5-tetrahydro-1H-benzo[b]azepine 27d was used instead of 8-fluoro-2,3,4,5-tetrahydro-1H-benzo[b]azepine 2e in step 3: m/z 491 [M+H]⁺ (ES⁺), 489 [M−H]⁻ (ES⁻) at $R_t$ 7.96 min (Method 2).

Procedure for the Preparation of 27d

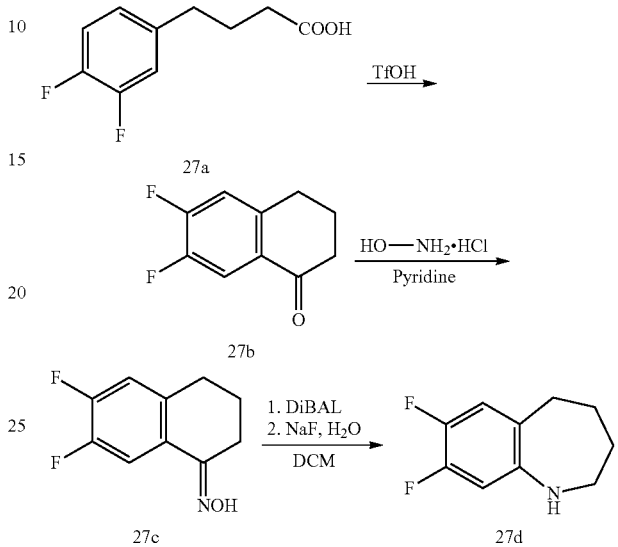

Step 1: A mixture of 4-(3,4-difluorophenyl)butanoic acid 27a (2.5 g, 12.5 mmol) and triflic acid (25.0 mL, 280 mmol) was stirred at RT for 1 h. After this time, the reaction mixture was poured in to iced water (100 mL) and the product was extracted with DCM (240 mL). The organic solution was washed with brine (120 mL), dried over MgSO₄, filtered and concentrated in vacuo to afford 6,7-difluoro-3,4-dihydronaphthalen-1(2H)-one 27b (1.9 g, 84%) as an orange solid: m/z 183 [M+H]⁺ (ES⁺) at $R_t$ 1.93 min (Method 1).

Step 2: Hydroxylamine hydrochloride (1.45 g, 20.9 mmol) was added to a stirred solution of 6,7-difluoro-3,4-dihydronaphthalen-1(2H)-one 27b (1.90 g, 10.4 mmol) in pyridine (20 mL). The mixture was stirred at RT for 16 h and then concentrated in vacuo. The residue was partitioned between EtOAc (50 mL) and water (50 mL). The aqueous layer was reextracted with EtOAc (50 mL) then the combined organic layers were washed with sat. brine (50 mL), dried over MgSO₄ and filtered. The solution was concentrated in vacuo and the residue was purified by silica gel chromatography (40 g, 0-50% EtOAc/isohexane) to 6,7-difluoro-3,4-dihydronaphthalen-1(2H)-one oxime 27c (1.7 g, 84%) as a white solid: m/z 198 [M+H]⁺ (ES⁺) at $R_t$ 2.02 min (Method 1).

Step 3: DIBAL-H (1M in hexane) (52 mL, 52 mmol) was added portionwise to a stirred solution of 6,7-difluoro-3,4-dihydronaphthalen-1(2H)-one oxime 27c (1.7 g, 8.6 mmol) in DCM (100 mL) over 45 min under an atmosphere of nitrogen and whilst chilling with iced water. After 5 min the solution was warmed to RT and stirred for 2 h. The mixture was cooled with iced water and powdered NaF (7 g) was added, followed by water (3 mL) cautiously. The suspension was stirred for 45 min then filtered through celite which was then washed with EtOAc. The filtrate was concentrated in vacuo and the residue was purified by silica gel chromatography (40 g, 0-20% EtOAc/isohexane) to afford 7,8-difluoro-2,3,4,5-tetrahydro-1H-benzo[b]azepine 27d (1.2 g, 66%) as a yellow oil: m/z 184 [M+H]⁺ (ES⁺) at $R_t$ 1.33 min (Method 1).

Example 12: Compound 11 (2S,4S)-1-(2,2-Diphenylacetyl)-4-(5,6,7,8-tetrahydro-4H-thieno[3,2-b]azepin-4-yl)pyrrolidine-2-carboxylic acid

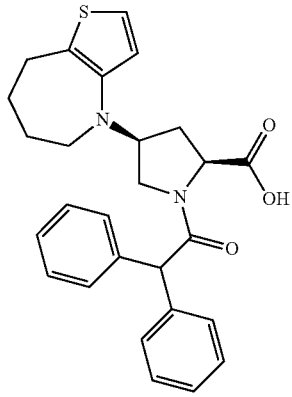 [SMILES: O=C(O)[C@@H]1C[C@H](N2CCCCc3sccc32)CN1C(=O)C(c1ccccc1)c1ccccc1]

(2S,4S)-1-(2,2-Diphenylacetyl)-4-(5,6,7,8-tetrahydro-4H-thieno[3,2-b]azepin-4-yl)pyrrolidine-2-carboxylic acid 11 (45 mg, 44% for final step) was prepared in essentially the same manner as for Compound 2 (Example 2) except that 5,6,7,8-tetrahydro-4H-thieno[3,2-b]azepine was used instead of 8-fluoro-2,3,4,5-tetrahydro-1H-benzo[b]azepine 2e in step 3: m/z 461 [M+H]⁺ (ES⁺) at $R_t$ 6.68 min (Method 2).

Example 13: Compound 13 (2S,4S)-1-(2,2-Diphenylacetyl)-4-(3,4,5,6-tetrahydrobenzo[b]azocin-1(2H)-yl)pyrrolidine-2-carboxylic acid

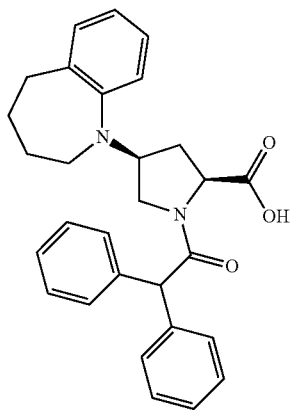 [SMILES: O=C(O)[C@@H]1C[C@H](N2CCCCc3ccccc32)CN1C(=O)C(c1ccccc1)c1ccccc1]

(2S,4S)-1-(2,2-Diphenylacetyl)-4-(3,4,5,6-tetrahydrobenzo[b]azocin-1(2H)-yl)pyrrolidine-2-carboxylic acid 13 (97 mg, 98% for final step) was prepared in essentially the same manner as for Compound 2 (Example 2) except that 1,2,3,4,5,6-hexahydrobenzo[b]azocine hydrochloride was used instead of 8-fluoro-2,3,4,5-tetrahydro-1H-benzo[b]azepine 2e in step 3 and the product was purified by capture and release on SCX (eluting with 1% NH₃/MeOH): m/z 469 [M+H]⁺ (ES⁺) at $R_t$ 7.80 min (Method 2).

Example 14: Compound 4 (2S,4S)-1-(2,2-Diphenylacetyl)-4-(7-methoxy-2,3,4,5-tetrahydro-1H-benzo[b]azepin-1-yl)pyrrolidine-2-carboxylic acid

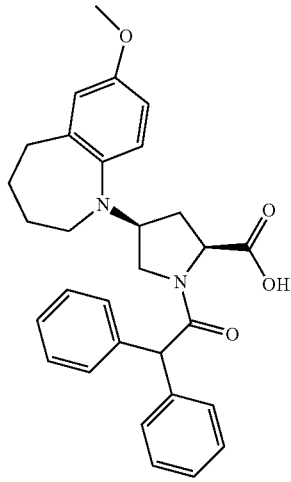 [SMILES: COc1ccc2c(c1)CCCCN2[C@H]1C[C@@H](C(=O)O)N(C(=O)C(c2ccccc2)c2ccccc2)C1]

(2S,4S)-1-(2,2-Diphenylacetyl)-4-(7-methoxy-2,3,4,5-tetrahydro-1H-benzo[b]azepin-1-yl)pyrrolidine-2-carboxylic acid 4 (130 mg, 78% for final step) was prepared in essentially the same manner as for Compound 2 (Example 2) except that 7-methoxy-2,3,4,5-tetrahydro-1H-benzo[b]azepine was used instead of 8-fluoro-2,3,4,5-tetrahydro-1H-benzo[b]azepine 2e in step 3 and the product was purified by capture and release on SCX (eluting with 1% NH₃/MeOH): m/z 485 [M+H]⁺ (ES⁺), 483 [M−H]⁻ (ES⁻) at $R_t$ 6.49 min (Method 2).

Example 15: Compound 5 (2S,4S)-1-(2,2-Diphenylacetyl)-4-(7-fluoro-2,3,4,5-tetrahydro-1H-benzo[b]azepin-1-yl)pyrrolidine-2-carboxylic acid

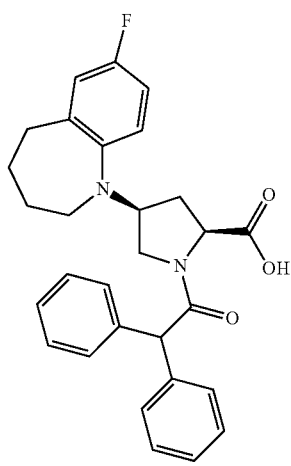 [SMILES: O=C(O)[C@@H]1C[C@H](N2CCCCc3cc(F)ccc32)CN1C(=O)C(c1ccccc1)c1ccccc1]

(2S,4S)-1-(2,2-Diphenylacetyl)-4-(7-fluoro-2,3,4,5-tetrahydro-1H-benzo[b]azepin-1-yl)pyrrolidine-2-carboxylic acid 5 (35 mg, 30% for final step) was prepared in essentially the same manner as for Compound 2 (Example 2) except that 7-fluoro-2,3,4,5-tetrahydro-1H-benzo[b]azepine (prepared in the same manner as compound 3) was used instead of 8-fluoro-2,3,4,5-tetrahydro-1H-benzo[b]azepine 2e in step 3): m/z 473 [M+H]⁺ (ES⁺), 471 [M−H]⁻ (ES⁻) at $R_t$ 7.70 min (Method 2).

Example 16: Compound 6 (2S,4S)-4-(7-Chloro-2,3,4,5-tetrahydro-1H-benzo[b]azepin-1-yl)-1-(2,2-diphenylacetyl)pyrrolidine-2-carboxylic acid

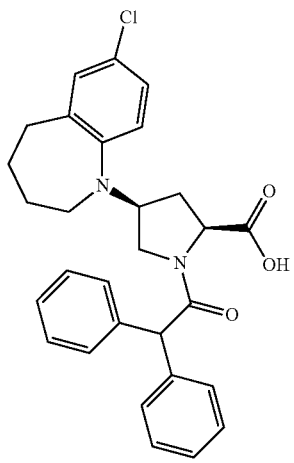 [SMILES: O=C(O)[C@@H]1C[C@H](N2CCCCc3cc(Cl)ccc32)CN1C(=O)C(c1ccccc1)c1ccccc1]

(2S,4S)-4-(7-Chloro-2,3,4,5-tetrahydro-1H-benzo[b]azepin-1-yl)-1-(2,2-diphenylacetyl)pyrrolidine-2-carboxylic acid 6 (72 mg, 55% for final step) was prepared in essentially the same manner as for Compound 2 (Example 2) except that 7-chloro-2,3,4,5-tetrahydro-1H-benzo[b]azepine (prepared in the same manner as compound 3) was used instead of 8-fluoro-2,3,4,5-tetrahydro-1H-benzo[b]azepine 2e in step 3): m/z 489 [M+H]⁺ (ES⁺), 487 [M−H]⁻ (ES⁻) at $R_t$ 7.70 min (Method 2).

Example 17: Compound 18 (2S,4S)-1-(2,2-Diphenylacetyl)-4-(1,3,4,5-tetrahydro-2H-benzo[c]azepin-2-yl)pyrrolidine-2-carboxylic acid

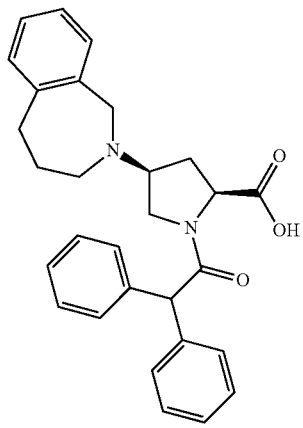 [SMILES: O=C(O)[C@@H]1C[C@H](N2CCCc3ccccc3C2)CN1C(=O)C(c1ccccc1)c1ccccc1]

(2S,4S)-1-(2,2-Diphenylacetyl)-4-(1,3,4,5-tetrahydro-2H-benzo[c]azepin-2-yl)pyrrolidine-2-carboxylic acid 18 (115 mg, 88% for final step) was prepared in essentially the same manner as for Compound 2 (Example 2) except that 2,3,4,5-tetrahydro-1H-benzo[c]azepine was used instead of 8-fluoro-2,3,4,5-tetrahydro-1H-benzo[b]azepine 2e in step 3): m/z 455 [M+H]⁺ (ES⁺) at $R_t$ 6.70 min (Method 2).

Example 18: Compound 28 (2S,4R)-1-(2,2-Diphenylacetyl)-4-(2,3,4,5-tetrahydro-1H-pyrido[3,4-b]azepin-1-yl)pyrrolidine-2-carboxylic acid

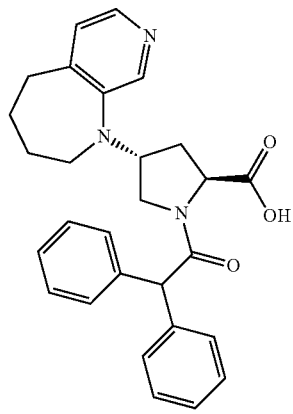 [SMILES: O=C(O)[C@@H]1C[C@@H](N2CCCCc3ccncc32)CN1C(=O)C(c1ccccc1)c1ccccc1]

(2S,4R)-1-(2,2-Diphenylacetyl)-4-(2,3,4,5-tetrahydro-1H-pyrido[3,4-b]azepin-1-yl)pyrrolidine-2-carboxylic acid 28 (15 mg, 31% for final step) was prepared in essentially the same manner as for Compound 2 (Example 2) except that 2,3,4,5-tetrahydro-1H-pyrido[3,4-b]azepine (prepared in the same manner as compound 2e) was used instead of 8-fluoro-2,3,4,5-tetrahydro-1H-benzo[b]azepine 2e in step 3): m/z 456 [M+H]⁺ (ES⁺), 454 [M−H]⁻ (ES⁻) at $R_t$ 2.41 min (Method 2).

Example 19: Compound 3 (2S,4S)-1-(2,2-Diphenylacetyl)-4-(8-methyl-2,3,4,5-tetrahydro-1H-benzo[b]azepin-1-yl)pyrrolidine-2-carboxylic acid

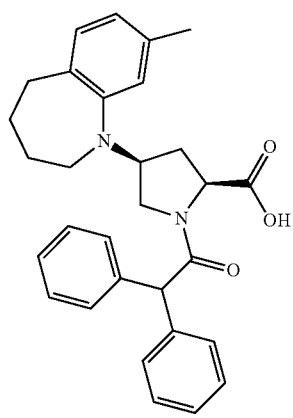 [SMILES: Cc1ccc2c(c1)N([C@H]1C[C@@H](C(=O)O)N(C(=O)C(c3ccccc3)c3ccccc3)C1)CCCC2]

(2S,4S)-1-(2,2-Diphenylacetyl)-4-(8-methyl-2,3,4,5-tetrahydro-1H-benzo[b]azepin-1-yl)pyrrolidine-2-carboxylic acid 3 (104 mg, 81% for final step) was prepared in essentially the same manner as for Compound 2 (Example 2) except that 8-methyl-2,3,4,5-tetrahydro-1H-benzo[b]azepine (prepared in the same manner as compound 3) was used instead of 8-fluoro-2,3,4,5-tetrahydro-1H-benzo[b]azepine 2e in step 3): m/z 469 [M+H]⁺ (ES⁻) at $R_t$ 7.82 min (Method 2).

Example 20: Compound 23 (2S,4R)-1-(2,2-Diphenylacetyl)-4-(8-methyl-2,3,4,5-tetrahydro-1H-benzo[b]azepin-1-yl)pyrrolidine-2-carboxylic acid

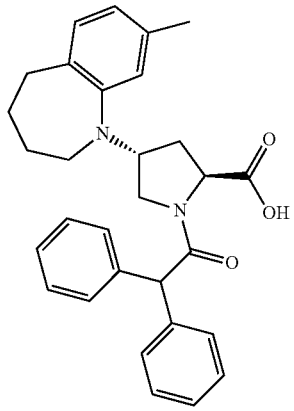 [SMILES: Cc1ccc2c(c1)N([C@@H]1C[C@@H](C(=O)O)N(C(=O)C(c3ccccc3)c3ccccc3)C1)CCCC2]

(2S,4R)-1-(2,2-Diphenylacetyl)-4-(8-methyl-2,3,4,5-tetrahydro-1H-benzo[b]azepin-1-yl)pyrrolidine-2-carboxylic acid 23 (4 mg, 3% for final step) was isolated during the purification of Compound 3 (Example 19): m/z 469 [M+H]$^+$ (ES$^+$) at R$_t$ 8.75 min (Method 2).

Example 21: Compound 29 (2S,4S)-1-(2,2-Diphenylacetyl)-4-(indolin-1-yl)pyrrolidine-2-carboxylic acid

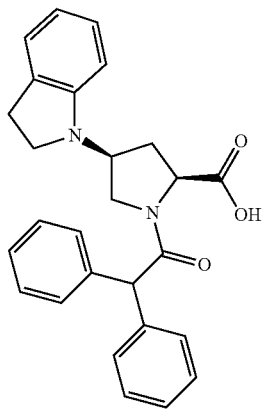 [SMILES: O=C(O)[C@@H]1C[C@H](N2CCc3ccccc32)CN1C(=O)C(c1ccccc1)c1ccccc1]

(2S,4S)-1-(2,2-Diphenylacetyl)-4-(indolin-1-yl)pyrrolidine-2-carboxylic acid 29 (226 mg, 82% for final step) was prepared in essentially the same manner as for Compound 2 (Example 2) except that indoline was used instead of 8-fluoro-2,3,4,5-tetrahydro-1H-benzo[b]azepine 2e in step 3): m/z 427 [M+H]$^+$ (ES$^+$), 425 [M–H]$^-$ (ES$^-$) at R$_t$ 6.76 min (Method 2).

Example 22: Compound 12 (2S,4S)-1-(2,2-Diphenylacetyl)-4-(5,6,7,8-tetrahydro-9H-pyrido[2,3-]azepin-9-yl)pyrrolidine-2-carboxylic acid

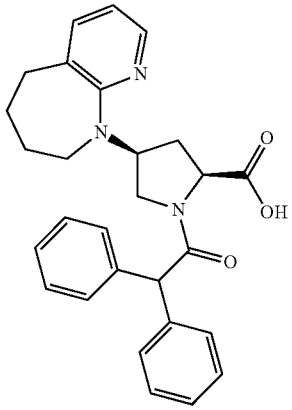 [SMILES: O=C(O)[C@@H]1C[C@H](N2CCCCc3cccnc32)CN1C(=O)C(c1ccccc1)c1ccccc1]

(2S,4S)-1-(2,2-Diphenylacetyl)-4-(5,6,7,8-tetrahydro-9H-pyrido[2,3-b]azepin-9-yl)pyrrolidine-2-carboxylic acid 12 (94 mg, 56% for final step) was prepared in essentially the same manner as for Compound 2 (Example 2) except that 6,7,8,9-tetrahydro-5H-pyrido[2,3-b]azepine (prepared in the same manner as compound 3) was used instead of 8-fluoro-2,3,4,5-tetrahydro-1H-benzo[b]azepine 2e in step 3): m/z 456 [M+H]$^+$ (ES$^+$), 454 [M–H]$^-$ (ES$^-$) at R$_t$ 3.59 min (Method 2).

Example 23: Compound 14 (2S,4S)-4-(3,4-Dihydroquinolin-1(2H)-yl)-1-(2,2-diphenylacetyl)pyrrolidine-2-carboxylic acid

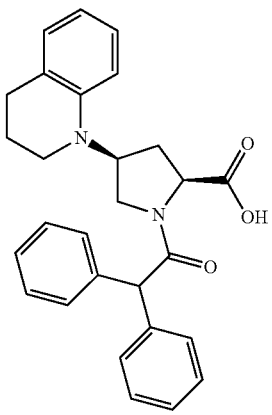 [SMILES: O=C(O)[C@@H]1C[C@H](N2CCCc3ccccc32)CN1C(=O)C(c1ccccc1)c1ccccc1]

(2S,4S)-4-(3,4-Dihydroquinolin-1(2H)-yl)-1-(2,2-diphenylacetyl)pyrrolidine-2-carboxylic acid 14 (69 mg, 38% for final step) was prepared in essentially the same manner as for Compound 1 (Example 1) except that 1,2,3,4-tetrahydroquinoline was used instead of 2,3,4,5-tetrahydro-1H-benzo[b]azepine in step 1): m/z 441 [M+H]$^+$ (ES$^+$), 439 [M–H]$^-$ (ES$^-$) at R$_t$ 7.34 min (Method 2).

Example 24: Compound 30 (2S,4S)-1-(2,2-Diphenylacetyl)-2-methyl-4-(2,3,4,5-tetrahydro-1H-benzo[b]azepin-1-yl)pyrrolidine-2-carboxylic acid

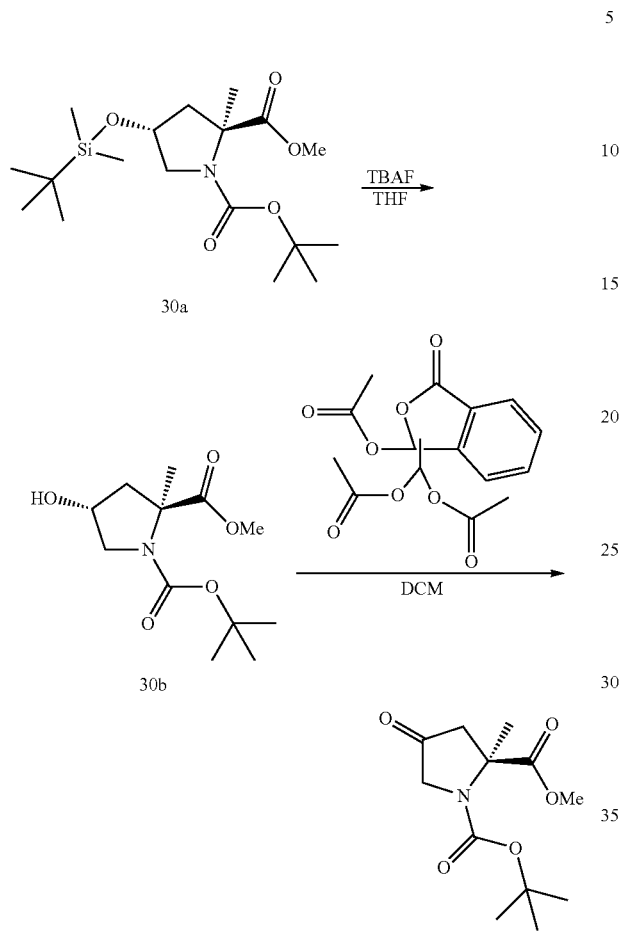

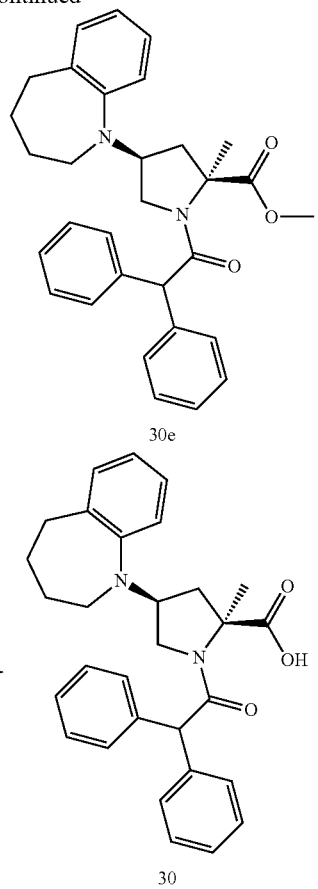

Procedure for the Preparation of 30b

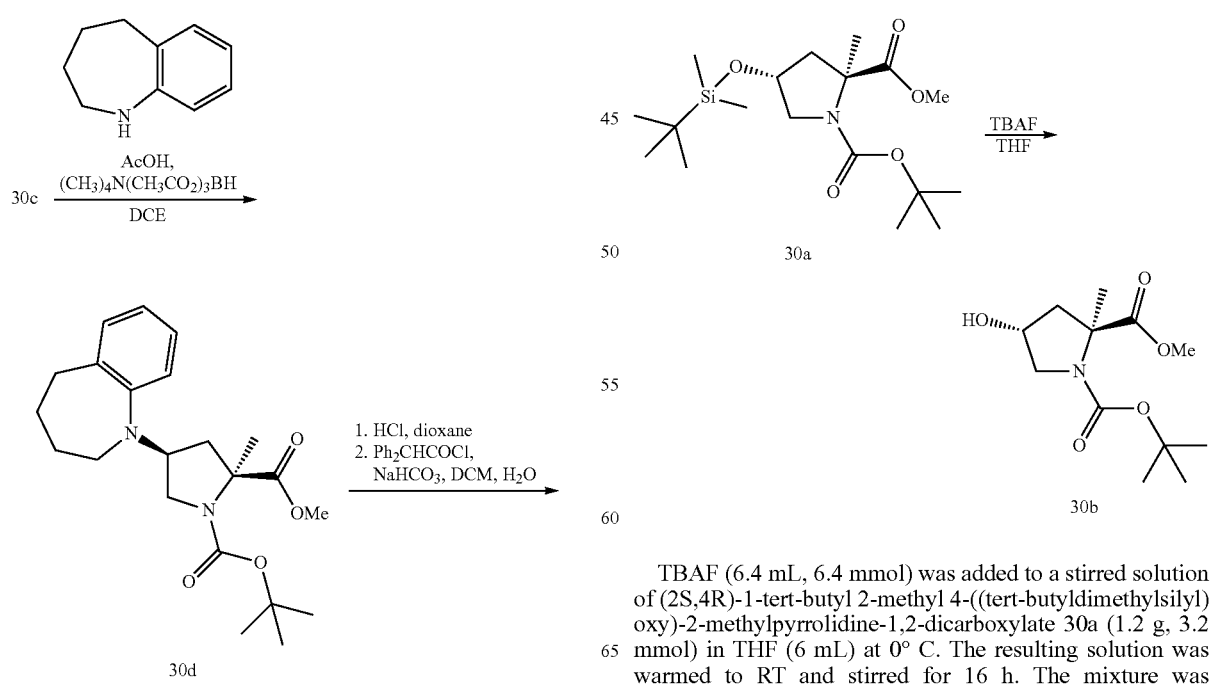

TBAF (6.4 mL, 6.4 mmol) was added to a stirred solution of (2S,4R)-1-tert-butyl 2-methyl 4-((tert-butyldimethylsilyl)oxy)-2-methylpyrrolidine-1,2-dicarboxylate 30a (1.2 g, 3.2 mmol) in THF (6 mL) at 0° C. The resulting solution was warmed to RT and stirred for 16 h. The mixture was concentrated in vacuo onto silica and purified by silica gel chromatography (24 g, 0-60% EtOAc in isohexane) to afford (2S,4R)-1-tert-butyl 2-methyl 4-hydroxy-2-methylpyrrolidine-1,2-dicarboxylate 30b (455 mg, 54%) as a white solid.

Procedure for the Preparation of 30c

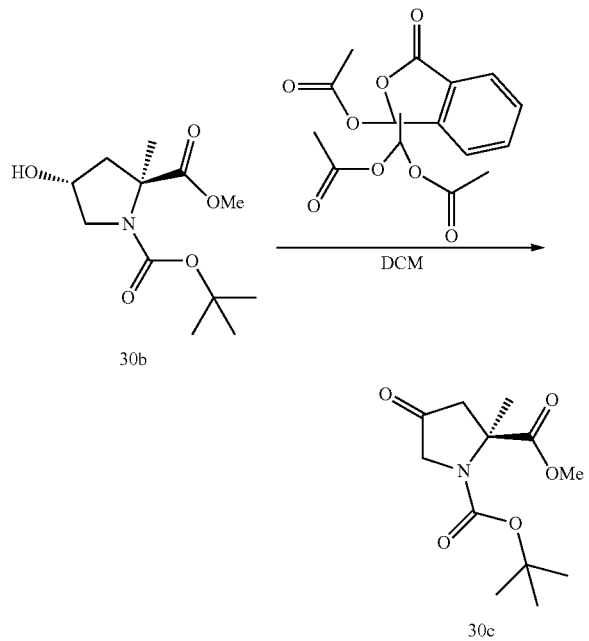

Dess-Martin Periodinane (1.1 g, 2.6 mmol) was added to a solution of (2S,4R)-1-tert-butyl 2-methyl 4-hydroxy-2-methylpyrrolidine-1,2-dicarboxylate 30b (450 mg, 1.7 mmol) in DCM (10 mL) at 0° C. The reaction mixture was then stirred at RT for 16 h. The mixture was diluted with DCM (10 mL) and washed sequentially with sat. NH$_4$Cl (20 mL), water (20 mL) and sat. brine (20 mL). The organic solution was dried over MgSO$_4$, filtered and concentrated in vacuo. The product was purified by silica gel chromatography (12 g, 0-60% EtOAc in isohexane) to afford (S)-1-tert-butyl 2-methyl 2-methyl-4-oxopyrrolidine-1,2-dicarboxylate 30c (360 mg, 79%) as a white solid.

Procedure for the Preparation of 30d

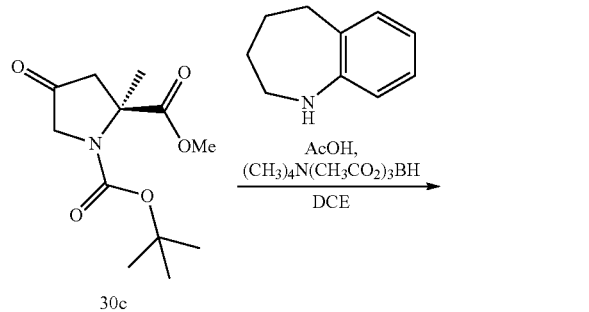

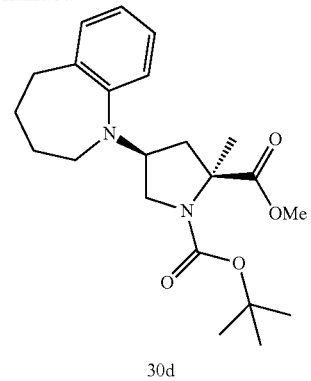

2,3,4,5-Tetrahydro-1H-benzo[b]azepine (92 mg, 0.63 mmol) was added to a stirred solution of (S)-1-tert-butyl 2-methyl 2-methyl-4-oxopyrrolidine-1,2-dicarboxylate 30c (160 mg, 0.63 mmol) in DCE (5 mL). AcOH (72 µL, 1.25 mmol) was added and the mixture was stirred at RT for 15 min before tetramethylammonium triacetoxyhydroborate (210 mg, 0.81 mmol) was added in one portion. The mixture was stirred at RT for 16 h and then concentrated in vacuo on to silica gel and purified by silica gel chromatography (24 g, 0-60% EtOAc in isohexane) to afford (2S,4S)-1-tert-butyl 2-methyl 2-methyl-4-(2,3,4,5-tetrahydro-1H-benzo[b]azepin-1-yl)pyrrolidine-1,2-dicarboxylate 30d (140 mg, 57%) as a white solid: m/z 389 [M+H]$^+$ (ES$^+$) at R$_t$ 2.98 min (Method 1).

Procedure for the Preparation of 30e

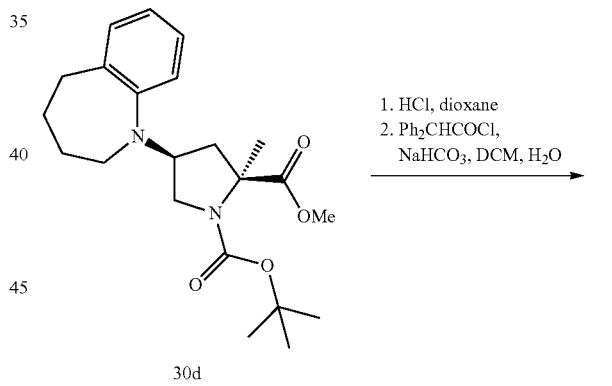

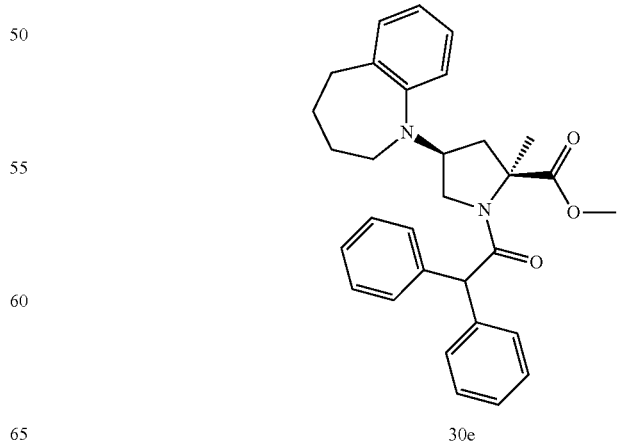

A mixture of (2S,4S)-1-tert-butyl 2-methyl 2-methyl-4-(2,3,4,5-tetrahydro-1H-benzo[b]azepin-1-yl)pyrrolidine-1,2-dicarboxylate 30d (140 mg, 0.35 mmol) and 4M HCl in dioxane (870 μL, 3.5 mmol) was stirred at RT for 30 min. The volatiles were removed in vacuo and the residue was dissolved in DCM (3 mL). Water (3 mL), NaHCO$_3$ (440 mg, 5.2 mmol) and 2,2-diphenylacetyl chloride (80 mg, 0.35 mmol) were added and the resulting mixture was stirred at RT for 16 h. The mixture was concentrated in vacuo onto silica gel and the product was purified by silica gel chromatography (12 g, 0-40% EtOAc in isohexane) to afford (2S,4S)-methyl 1-(2,2-diphenylacetyl)-2-methyl-4-(2,3,4,5-tetrahydro-1H-benzo[b]azepin-1-yl)pyrrolidine-2-carboxylate 30e (120 mg, 71%) as a white solid: m/z 483 [M+H]$^+$ (ES$^+$) at R$_t$ 3.07 min (Method 1).

Procedure for the Preparation of 30

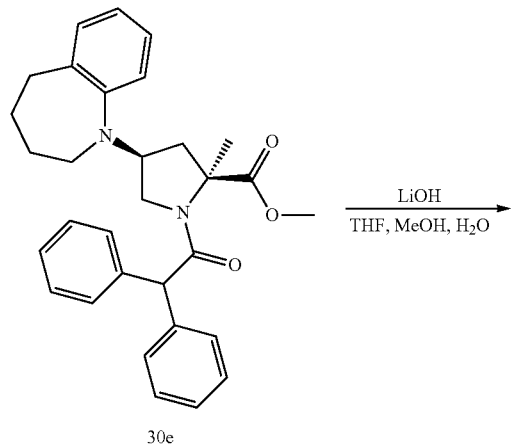

LiOH (18 mg, 0.76 mmol) was added to a stirred solution of (2S,4S)-methyl 1-(2,2-diphenylacetyl)-2-methyl-4-(2,3,4,5-tetrahydro-1H-benzo[b]azepin-1-yl)pyrrolidine-2-carboxylate 30e (120 mg, 0.25 mmol) in THF (10 mL) and water (5 mL). The mixture was stirred at RT for 16 h, then at 60° C. for a further 24 h. The mixture was concentrated in vacuo on to silica gel and the product was purified by silica gel chromatography (12 g, 0-40% EtOAc in isohexane) to afford (2S,4S)-1-(2,2-diphenylacetyl)-2-methyl-4-(2,3,4,5-tetrahydro-1H-benzo[b]azepin-1-yl)pyrrolidine-2-carboxylic acid 30 (78 mg, 55%) as a white solid: m/z 469 [M+H]$^+$ (ES$^+$), 467 [M−H]$^-$ (ES$^-$) at R$_t$ 7.69 min (Method 2).

Example 25: Compound 31 (2S,4S)-4-(7,8-Difluoro-2,3,4,5-tetrahydro-1H-benzo[b]azepin-1-yl)-1-(2,2-diphenylacetyl)-2-methylpyrrolidine-2-carboxylic acid

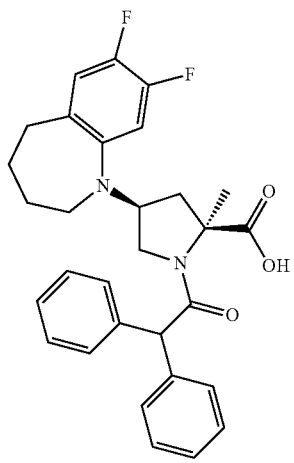 [SMILES: C[C@@]1(C(=O)O)C[C@H](N2CCCCc3cc(F)c(F)cc32)CN1C(=O)C(c1ccccc1)c1ccccc1]

(2S,4S)-4-(7,8-Difluoro-2,3,4,5-tetrahydro-1H-benzo[b]azepin-1-yl)-1-(2,2-diphenylacetyl)-2-methylpyrrolidine-2-carboxylic acid 31 (105 mg, 31% for final step) was prepared in essentially the same manner as for Compound 30 (Example 24) except that 7,8-difluoro-2,3,4,5-tetrahydro-1H-benzo[b]azepine 27d (Example 11) was used instead of 2,3,4,5-tetrahydro-1H-benzo[b]azepine in step 3, NaOH was used instead of LiOH in step 5 and the product was purified by preparative HPLC (Diacel Chiralpak IA column, 70% (0.2% TFA in isohexane), 23% MTBE, 7% EtOH, isocratic): m/z 505 [M+H]$^+$ (ES$^+$) at R$_t$ 9.01 min (Method 2).

Example 26: Compound 32 (2S,4S)-4-(7,8-Difluoro-3,4-dihydrobenzo[b][1,4]oxazepin-5(2H)-yl)-1-(2,2-diphenylacetyl)-2-methylpyrrolidine-2-carboxylic acid

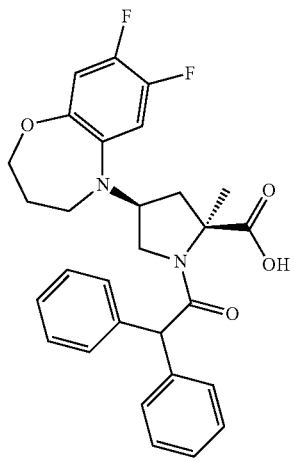 [SMILES: C[C@@]1(C(=O)O)C[C@H](N2CCCOc3cc(F)c(F)cc32)CN1C(=O)C(c1ccccc1)c1ccccc1]

(2S,4S)-4-(7,8-Difluoro-3,4-dihydrobenzo[b][1,4]oxazepin-5(2H)-yl)-1-(2,2-diphenylacetyl)-2-methylpyrrolidine-2-carboxylic acid 32 (12 mg, 19% for final step) was prepared in essentially the same manner as for Compound 30 (Example 24) except 7,8-difluoro-2,3,4,5-tetrahydrobenzo[b][1,4]oxazepine 21e (Example 6) was used instead of 2,3,4,5-tetrahydro-1H-benzo[b]azepine in step 3, NaOH was used instead of LiOH in step 5 and the product was purified by preparative HPLC (Diacel Chiralpak IA column, 70% (0.2% TFA in isohexane), 23% MTBE, 7% EtOH, isocratic): m/z 507 [M+H]+ (ES+) at $R_t$ 8.01 min (Method 2).

Example 27: Compound 33 (2S,4S)-1-(2,2-Diphenylacetyl)-4-(8-fluoro-3,4-dihydrobenzo[b][1,4]oxazepin-5(2H)-yl)-2-methylpyrrolidine-2-carboxylic acid

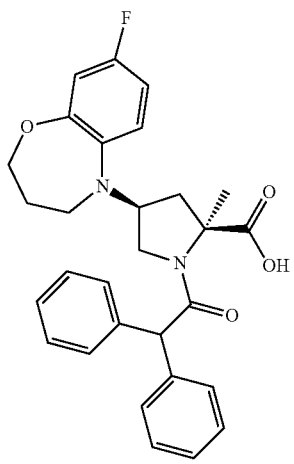 [SMILES: C[C@@]1(C(=O)O)C[C@H](N2CCCOc3cc(F)ccc32)CN1C(=O)C(c1ccccc1)c1ccccc1]

(2S,4S)-1-(2,2-Diphenylacetyl)-4-(8-fluoro-3,4-dihydrobenzo[b][1,4]oxazepin-5(2H)-yl)-2-methylpyrrolidine-2-carboxylic acid 33 (12 mg, 8% for final step) was prepared in essentially the same manner as for Compound 30 (Example 24) except 8-fluoro-2,3,4,5-tetrahydrobenzo[b][1,4]oxazepine was used instead of 2,3,4,5-tetrahydro-1H-benzo[b]azepine in step 3): m/z 487 [M+H]+ (ES+) at $R_t$ 8.61 min (Method 2).

Example 28: Compound 34 (2S,4S)-4-(1,1-Dioxido-3,4-dihydrobenzo[b][1,4]thiazepin-5(2H)-yl)-1-(2,2-diphenylacetyl)pyrrolidine-2-carboxylic acid

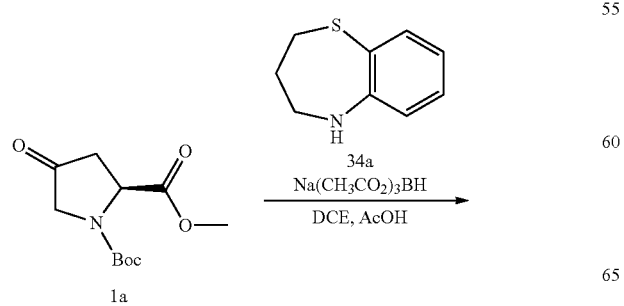

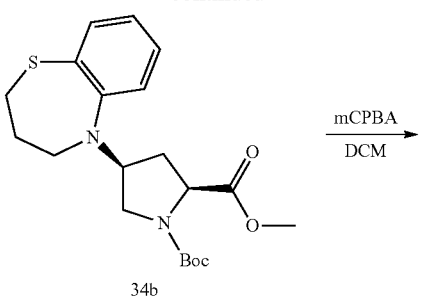

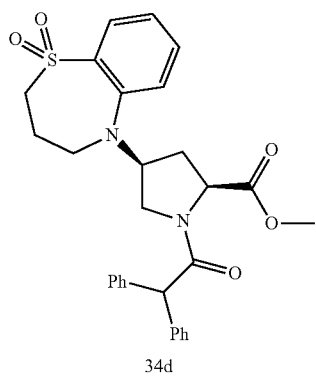

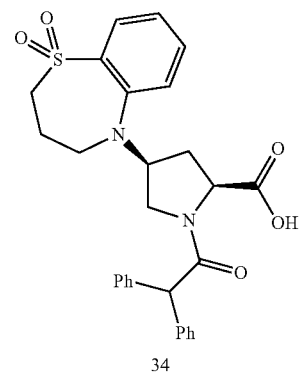

Procedure for the Preparation of 31a

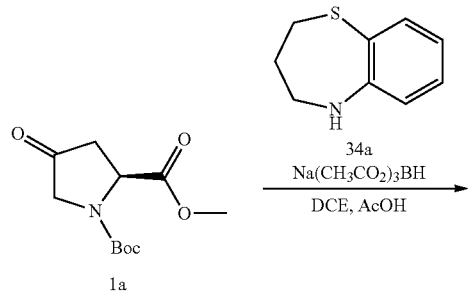

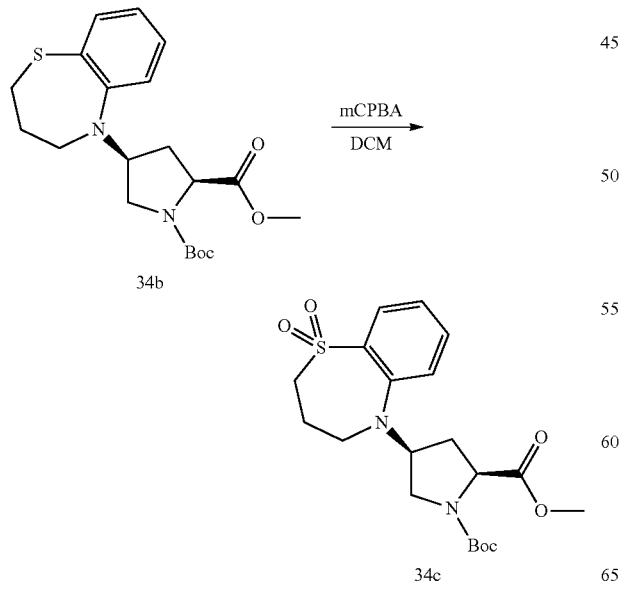

Sodium triacetoxyhydroborate (1.8 g, 8.5 mmol) was added to a stirred mixture of 2,3,4,5-tetrahydrobenzo[b][1,4]thiazepine 34a (0.70 g, 4.3 mmol) and (S)-1-tert-butyl 2-methyl 4-oxopyrrolidine-1,2-dicarboxylate 1a (1.1 g, 4.7 mmol) in DCE (3 mL) and AcOH (3 mL). The mixture was stirred at RT for 16 h and then concentrated in vacuo onto silica gel for purification by silica gel chromatography (40 g, 0-50% EtOAc in iso-hexane) to afford (2S,4S)-1-tert-butyl 2-methyl 4-(3,4-dihydrobenzo[b][1,4]thiazepin-5(2H)-yl)pyrrolidine-1,2-dicarboxylate 34b (0.8 g, 45%) as a yellow oil: m/z 393 [M+H]$^+$ (ES$^+$) at R$_t$ 2.68 min (Method 1).

Procedure for the Preparation of 34c

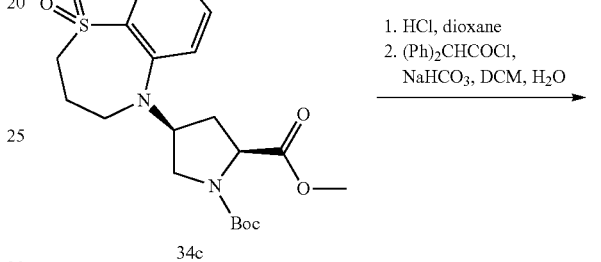

mCPBA (2.2 g, 5.2 mmol) was added to a stirred solution of (2S,4S)-1-tert-butyl 2-methyl 4-(3,4-dihydrobenzo[b][1,4]thiazepin-5(2H)-yl)pyrrolidine-1,2-dicarboxylate 34b (0.8 g, 2.1 mmol) in DCM (15 mL) at RT. After stirring at RT for 1 h the mixture was diluted with DCM (50 mL) and then washed sequentially with 5% Na$_2$S$_2$O$_3$ (50 mL) and 5% NaHCO$_3$ (50 mL). The organic solution was dried over MgSO$_4$, filtered and concentrated in vacuo. The product was purified by silica gel chromatography (40 g, 0-70% EtOAc in iso-hexane) to afford (2S,4S)-1-tert-butyl 2-methyl 4-(1,1-dioxido-3,4-dihydrobenzo[b][1,4]thiazepin-5(2H)-yl)pyrrolidine-1,2-dicarboxylate 34c (0.6 g, 67%) as a colourless oil: m/z 325 [M-Boc+H]$^+$ (ES$^+$) at R$_t$ 2.70 min (Method 1).

Procedure for the Preparation of 34d

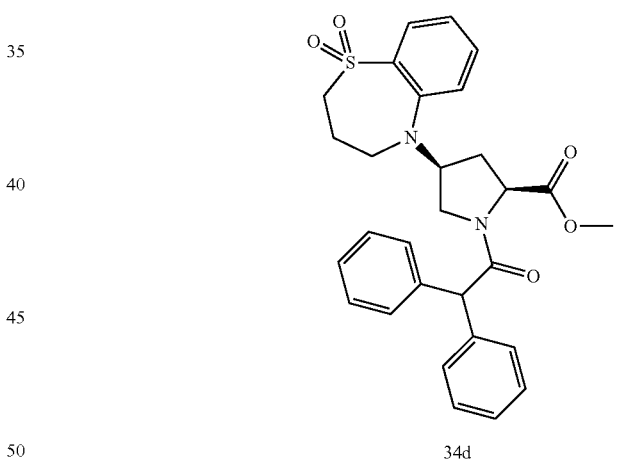

A mixture of (2S,4S)-1-tert-butyl 2-methyl 4-(1,1-dioxido-3,4-dihydrobenzo[b][1,4]thiazepin-5(2H)-yl)pyrrolidine-1,2-dicarboxylate 34c (570 mg, 1.35 mmol) and 4M HCl in dioxane (3.4 μL, 13.5 mmol) was stirred at RT for 4 h. The mixture was concentrated in vacuo and the residue was dissolved in DCM (30 mL) and water (30 mL) was added. NaHCO$_3$ (1.7 g, 20 mmol) and 2,2-diphenylacetyl chloride (310 mg, 1.35 mmol) were added and the biphasic mixture was stirred at RT for 16 h. The mixture was concentrated in vacuo onto silica gel for purification by chromatography (24 g, 0-40% EtOAc in iso-hexane) to afford (2S,4S)-methyl 4-(1,1-dioxido-3,4-dihydrobenzo[b][1,4]thiazepin-5(2H)-yl)-1-(2,2-diphenylacetyl)pyrrolidine-2-carboxylate 34d (440 mg, 59%) as a white solid: m/z 519 [M+H]$^+$ (ES$^+$) at R$_t$ 2.31 min (Method 1).

Procedure for the Preparation of 34

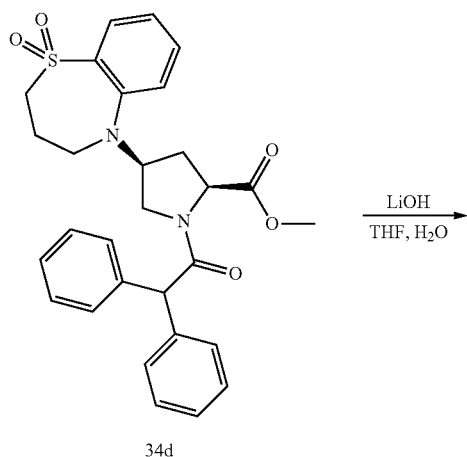

34d

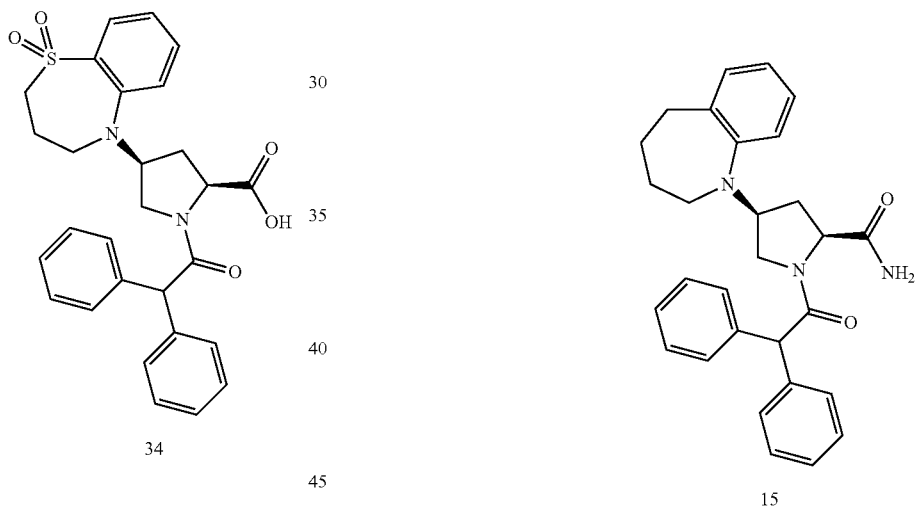

34

Example 29: Compound 15 (2S,4S)-1-(2,2-Diphenylacetyl)-4-(2,3,4,5-tetrahydro-1H-benzo[b]azepin-1-yl)pyrrolidine-2-carboxamide

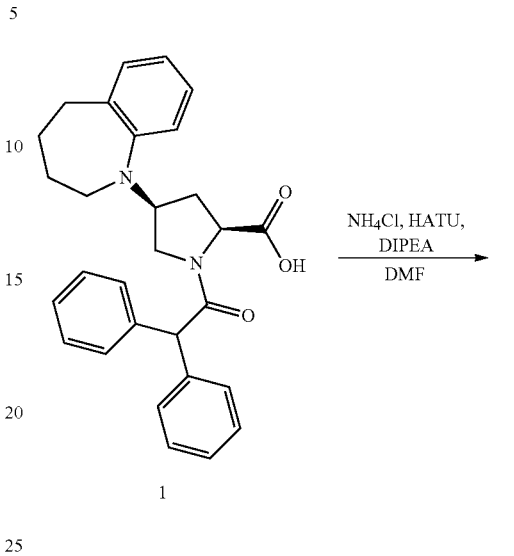

1

15

LiOH (60 mg, 2.5 mmol) was added to a stirred solution of (2S,4S)-methyl 4-(1,1-dioxido-3,4-dihydrobenzo[b][1,4]thiazepin-5(2H)-yl)-1-(2,2-diphenylacetyl)pyrrolidine-2-carboxylate 34d (430 mg, 0.83 mmol) in THF (7 mL), water (3 mL) and MeOH (0.5 mL). The mixture was stirred at RT for 1 h and then concentrated in vacuo onto silica gel for purification by chromatography (12 g, 0-100% (1% AcOH) EtOAc in iso-hexane) to afford (2S,4S)-4-(1,1-dioxido-3,4-dihydrobenzo[b][1,4]thiazepin-5(2H)-yl)-1-(2,2-diphenylacetyl)pyrrolidine-2-carboxylic acid 34 (320 mg, 76%) as a white solid: m/z 505 [M+H]$^+$ (ES$^+$) at R$_t$ 5.91 min (Method 2).

A mixture of (2S,4S)-1-(2,2-diphenylacetyl)-4-(2,3,4,5-tetrahydro-1H-benzo[b]azepin-1-yl)pyrrolidine-2-carboxylic acid 1 (60 mg, 0.13 mmol), ammonium chloride (14 mg, 0.26 mmol), HATU (75 mg, 0.20 mmol) and DIPEA (70 μL, 0.40 mmol) in DMF (1 mL) was stirred at RT for 20 h. The mixture was diluted with EtOAc (20 mL) then washed with water (10 mL), followed by sat. brine (5 mL). The organic solution was then dried over MgSO$_4$, filtered and concentrated in vacuo. The product was purified by silica gel chromatography (12 g, 0-100% EtOAc in iso-hexane) to afford (2S,4S)-1-(2,2-diphenylacetyl)-4-(2,3,4,5-tetrahydro-1H-benzo[b]azepin-1-yl)pyrrolidine-2-carboxamide 15 (53 mg, 84%) as a white solid: m/z 454 [M+H]$^+$ (ES$^+$) at R$_t$ 6.25 min (Method 2).

Example 30: Compound 35 2,2-Diphenyl-1-((2S,4S)-4-(2,3,4,5-tetrahydro-1H-benzo[b]azepin-1-yl)-2-(2H-tetrazol-5-yl)pyrrolidin-1-yl)ethan-1-one

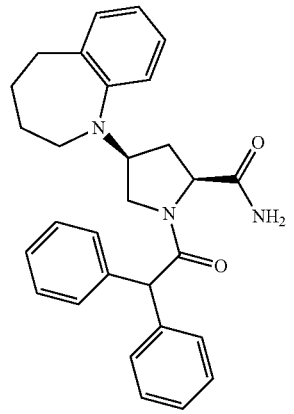

15

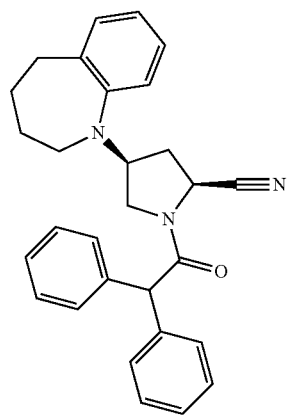

35a

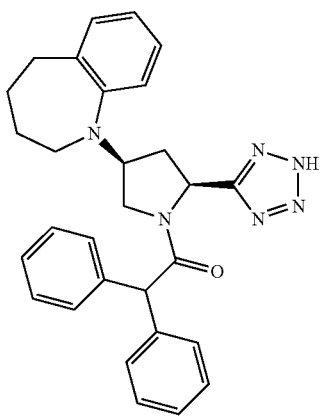

35

Procedure for the Preparation of 35a

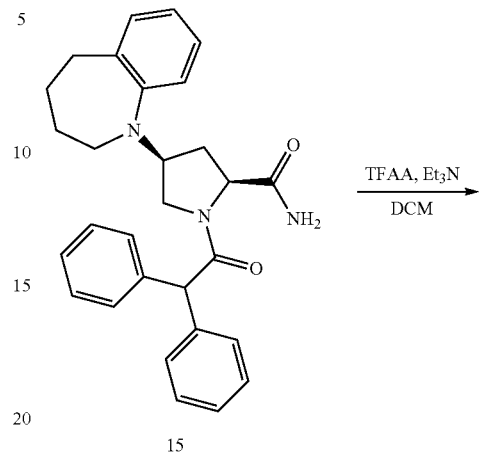

15

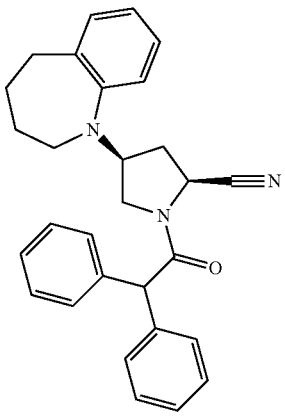

35a

Et$_3$N (230 µL, 1.64 mmol) was added to a solution of (2S,4S)-1-(2,2-diphenylacetyl)-4-(2,3,4,5-tetrahydro-1H-benzo[b]azepin-1-yl)pyrrolidine-2-carboxamide 15 (495 mg, 1.09 mmol) in DCM (5 mL) at 0° C. The resulting mixture stirred at 0° C. for 15 min. before TFAA (185 µl, 1.31 mmol) was added dropwise. The mixture continued to stir at 0° C. for 30 min, then was warmed to RT and stirred for a further 16 h. The reaction was quenched by the addition of sat. aq. NaHCO$_3$ (3 mL), the layers were separated and any residual product was extracted from the aqueous solution with further DCM (9 mL). The combined organic solutions were dried over MgSO$_4$, filtered and concentrated in vacuo. The product was purified by silica gel chromatography (4 g, EtOAc in iso-hexane) to afford (2S,4S)-1-(2,2-diphenylacetyl)-4-(2,3,4,5-tetrahydro-1H-benzo[b]azepin-1-yl)pyrrolidine-2-carbonitrile 35a (144 mg, 30%) as a brown oil: m/z 436 [M+H]$^+$ (ES$^+$) at R$_t$ 2.88 min (Method 1).

Procedure for the Preparation of 35

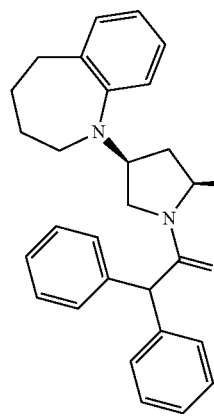

Example 31: Compound 36 (2S,4S)—N-(Cyclopropylsulfonyl)-4-(7,8-difluoro-3,4-dihydrobenzo[b][1,4]oxazepin-5(2H)-yl)-1-(2,2-diphenylacetyl)pyrrolidine-2-carboxamide

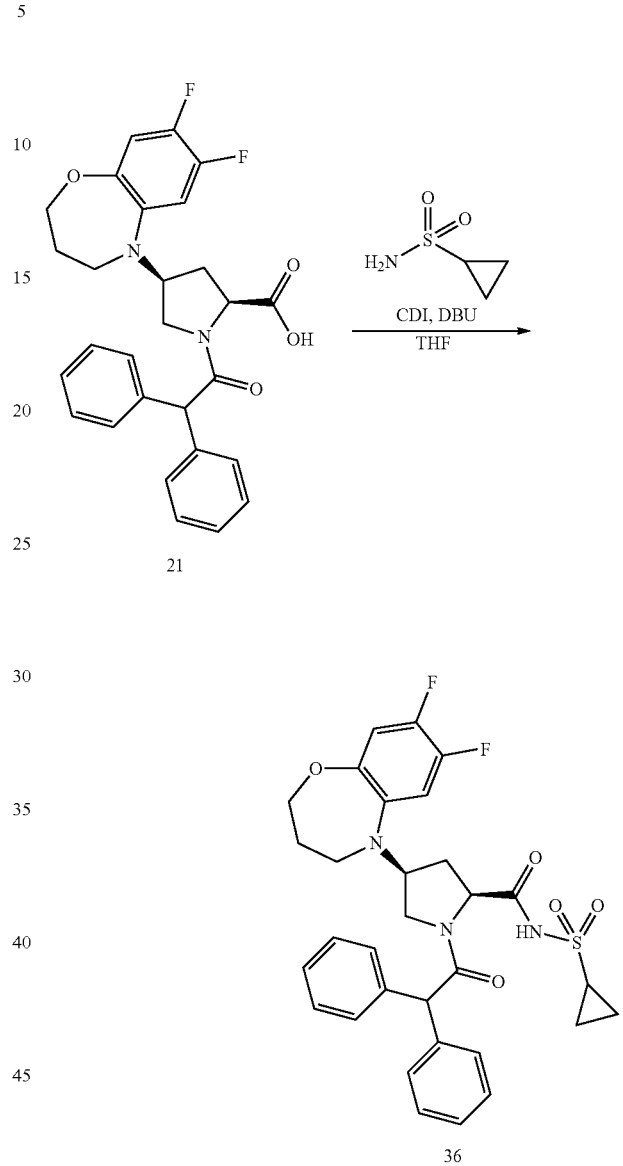

Sodium azide (90 mg, 1.38 mmol) and ammonium chloride (100 mg, 1.9 mmol) were added to a stirred solution of (2S,4S)-1-(2,2-diphenylacetyl)-4-(2,3,4,5-tetrahydro-1H-benzo[b]azepin-1-yl)pyrrolidine-2-carbonitrile 35a (120 mg, 0.28 mmol) in DMF (0.8 mL) at RT. The resulting mixture was heated and stirred at 100° C. for 16 h. After cooling to RT the mixture was diluted with water (5 mL) and EtOAc (20 mL). The layers were separated and the organic solution was dried over MgSO$_4$, filtered and concentrated in vacuo. The product was purified by silica gel chromatography (4 g, 0-10% (1% NH$_3$ in MeOH) in DCM) to afford 2,2-diphenyl-1-((2S,4S)-4-(2,3,4,5-tetrahydro-1H-benzo[b]azepin-1-yl)-2-(2H-tetrazol-5-yl)pyrrolidin-1-yl)ethan-1-one 35 (57 mg, 40%) an off-white solid: m/z 479 [M+H]$^+$ (ES$^+$) at R$_t$ 7.45 min (Method 2).

CDI (13 mg, 0.08 mmol) was added to a solution of (2S,4S)-4-(7,8-difluoro-3,4-dihydrobenzo[b][1,4]oxazepin-5(2H)-yl)-1-(2,2-diphenylacetyl)pyrrolidine-2-carboxylic acid 21 (example 6) (30 mg, 0.058 mmol) in THF (1 mL). The mixture was stirred at RT for 5 h, then cyclopropanesulfonamide (12 mg, 0.10 mmol) was added followed by DBU (24 μL, 0.16 mmol). The mixture was stirred at RT for a further 18 h then partitioned between DCM (4 mL) and 1M HCl (4 mL). The mixture was passed through a hydrophobic membrane and the organic solution was concentrated in vacuo. The product was purified by silica gel chromatography (4 g, 0-100% EtOAc in iso-hexane) to afford (2S,4S)—N-(Cyclopropylsulfonyl)-4-(7,8-difluoro-3,4-dihydrobenzo[b][1,4]oxazepin-5(2H)-yl)-1-(2,2-diphenylacetyl) pyrrolidine-2-carboxamide 36 (15 mg, 37%) as a colourless gum: m/z 596 [M+H]$^+$ (ES$^+$), 594 [M−H]$^-$ (ES$^-$) at R$_t$ 7.64 min (Method 2).

Example 32: Compound 37 (2S,4S)—N-(Cyclopropylsulfonyl)-1-(2,2-diphenylacetyl)-4-(7-fluoro-3,4-dihydrobenzo[b][1,4]oxazepin-5(2H)-yl)pyrrolidine-2-carboxamide

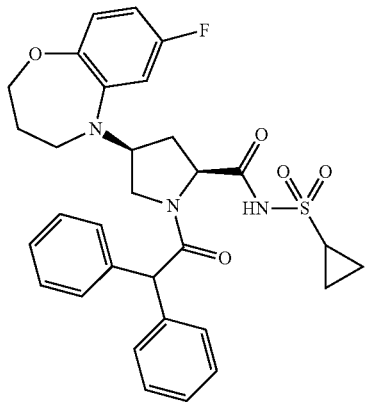 [SMILES: O=C(NS(=O)(=O)C1CC1)[C@@H]1C[C@H](N2CCCOc3ccc(F)cc32)CN1C(=O)C(c1ccccc1)c1ccccc1]

(2S,4S)—N-(Cyclopropylsulfonyl)-1-(2,2-diphenylacetyl)-4-(7-fluoro-3,4-dihydrobenzo[b][1,4]oxazepin-5(2H)-yl)pyrrolidine-2-carboxamide 37 (49 mg, 47% for final step) was prepared in essentially the same manner as for Compound 36 (Example 31) except (2S,4S)-1-(2,2-diphenylacetyl)-4-(7-fluoro-3,4-dihydrobenzo[b][1,4]oxazepin-5(2H)-yl)pyrrolidine-2-carboxylic acid 8 was used instead of (2S,4S)-4-(7,8-difluoro-3,4-dihydrobenzo[b][1,4]oxazepin-5(2H)-yl)-1-(2,2-diphenylacetyl)pyrrolidine-2-carboxylic acid 21: m/z 578 [M+H]$^+$ (ES$^+$), 576 [M−H]$^-$ (ES$^-$) at R$_t$ 7.37 min (Method 2).

Example 33: Compound 38 (2S,4S)—N-(Cyclopropylsulfonyl)-1-(2,2-diphenylacetyl)-4-(8-fluoro-3,4-dihydrobenzo[b][1,4]oxazepin-5(2H)-yl)pyrrolidine-2-carboxamide

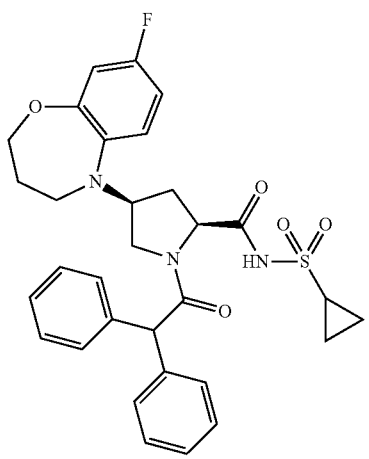 [SMILES: O=C(NS(=O)(=O)C1CC1)[C@@H]1C[C@H](N2CCCOc3cc(F)ccc32)CN1C(=O)C(c1ccccc1)c1ccccc1]

(2S,4S)—N-(Cyclopropylsulfonyl)-1-(2,2-diphenylacetyl)-4-(8-fluoro-3,4-dihydrobenzo[b][1,4]oxazepin-5(2H)-yl)pyrrolidine-2-carboxamide 38 (38 mg, 63% for final step) was prepared in essentially the same manner as for Compound 36 (Example 31) except (2S,4S)-1-(2,2-diphenylacetyl)-4-(8-fluoro-3,4-dihydrobenzo[b][1,4]oxazepin-5(2H)-yl)pyrrolidine-2-carboxylic acid 9 was used instead of (2S,4S)-4-(7,8-difluoro-3,4-dihydrobenzo[b][1,4]oxazepin-5(2H)-yl)-1-(2,2-diphenylacetyl)pyrrolidine-2-carboxylic acid 21: m/z 578 [M+H]$^+$ (ES$^+$), 576 [M−H]$^-$ (ES$^-$) at R$_t$ 7.32 min (Method 2).

Example 34: Compound 39 (2S,4S)-4-(7,8-Difluoro-3,4-dihydrobenzo[b][1,4]oxazepin-5(2H)-yl)-N—(N,N-dimethylsulfamoyl)-1-(2,2-diphenylacetyl)pyrrolidine-2-carboxamide

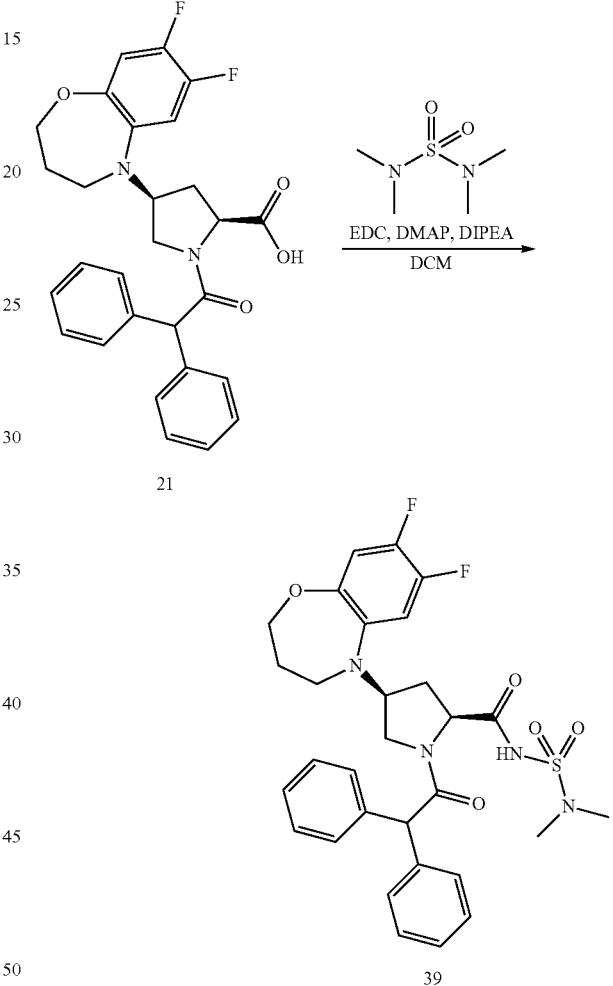

A mixture of (2S,4S)-4-(7,8-difluoro-3,4-dihydrobenzo[b][1,4]oxazepin-5(2H)-yl)-1-(2,2-diphenylacetyl)pyrrolidine-2-carboxylic acid 21 (85 mg, 0.173 mmol), dimethylsulfamide (36 mg, 0.29 mmol), DMAP (2 mg, 0.02 mmol), EDC (46 mg, 0.24 mmol) and DIPEA (90 μL, 0.52 mmol) in DCM (5 mL) was stirred at RT for 16 h. The reaction mixture was partitioned between DCM (5 mL) and 1M HCl (5 mL) and then passed through a hydrophobic membrane. The organic solution was concentrated in vacuo and the product was purified by silica gel chromatography (4 g, 0-60% EtOAc in iso-hexane). The product was further purified by preparative HPLC ((0.1% Formic acid) 50-65% MeCN in Water) to afford (2S,4S)-4-(7,8-difluoro-3,4-dihydrobenzo[b][1,4]oxazepin-5(2H)-yl)-N—(N,N-dimethylsulfamoyl)-1-(2,2-diphenylacetyl) pyrrolidine-2-carboxamide 39 (6 mg, 6%) as an off-white solid: m/z 599 [M+H]+ (ES+), 597 [M−H]− (ES−) at R_t 7.74 min (Method 2).

Example 35: Compound 40 (2S,4S)-4-(7,8-Difluoro-2,3,4,5-tetrahydro-1H-benzo[b]azepin-1-yl)-N—(N,N-dimethylsulfamoyl)-1-(2,2-diphenylacetyl)pyrrolidine-2-carboxamide

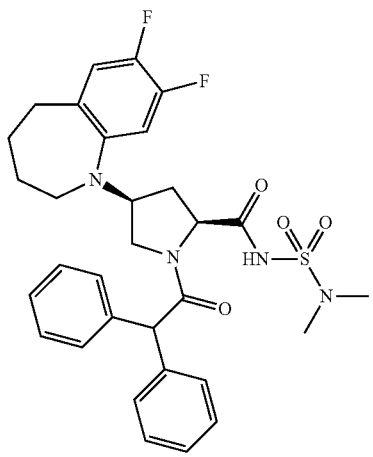 [SMILES: CN(C)S(=O)(=O)NC(=O)[C@@H]1C[C@H](N2CCCCc3cc(F)c(F)cc32)CN1C(=O)C(c1ccccc1)c1ccccc1]

(2S,4S)-4-(7,8-Difluoro-2,3,4,5-tetrahydro-1H-benzo[b]azepin-1-yl)-N—(N,N-dimethylsulfamoyl)-1-(2,2-diphenylacetyl)pyrrolidine-2-carboxamide 40 (6 mg, 5%) was prepared from (2S,4S)-4-(7,8-difluoro-2,3,4,5-tetrahydro-1H-benzo[b]azepin-1-yl)-1-(2,2-diphenylacetyl) pyrrolidine-2-carboxylic acid 27 using a procedure essentially the same as for Compound 39 (Example 34): m/z 597 [M+H]+ (ES+), 595 [M−H]− (ES−) at R_t 8.59 min (Method 2).

Example 36: Compound 41 (2S,4S)—N-(Cyclopropylsulfonyl)-4-(7,8-difluoro-2,3,4,5-tetrahydro-1H-benzo[b]azepin-1-yl)-1-(2,2-diphenylacetyl)pyrrolidine-2-carboxamide

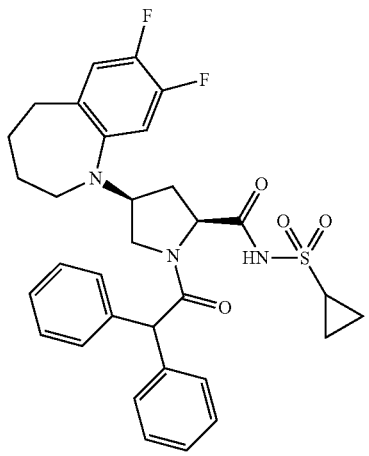 [SMILES: O=C(NS(=O)(=O)C1CC1)[C@@H]1C[C@H](N2CCCCc3cc(F)c(F)cc32)CN1C(=O)C(c1ccccc1)c1ccccc1]

(2S,4S)—N-(Cyclopropylsulfonyl)-4-(7,8-difluoro-2,3,4,5-tetrahydro-1H-benzo[b]azepin-1-yl)-1-(2,2-diphenylacetyl)pyrrolidine-2-carboxamide 41 (5 mg, 4%) was prepared from (2S,4S)-4-(7,8-difluoro-2,3,4,5-tetrahydro-1H-benzo[b]azepin-1-yl)-1-(2,2-diphenylacetyl) pyrrolidine-2-carboxylic acid 27 and cyclopropanesulfonamide using a procedure essentially the same as for Compound 39 (Example 34): m/z 594 [M+H]+ (ES+) at R_t 8.43 min (Method 2).

Example 37: Compounds 42a (2S,4S)—N-(Cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide and 42b (2S,4R)—N-(cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide

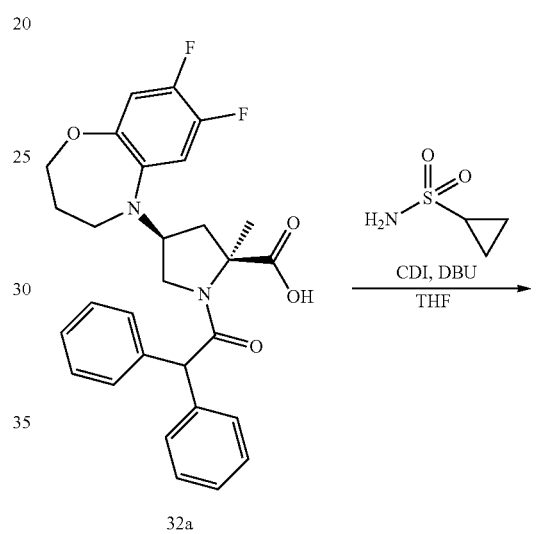

32a

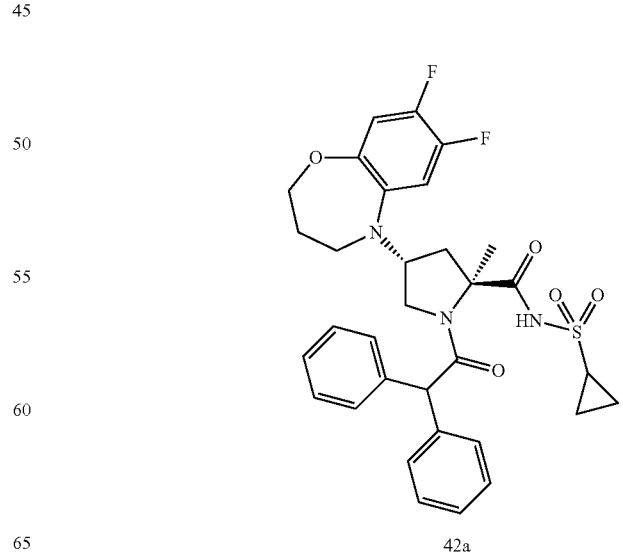

42a

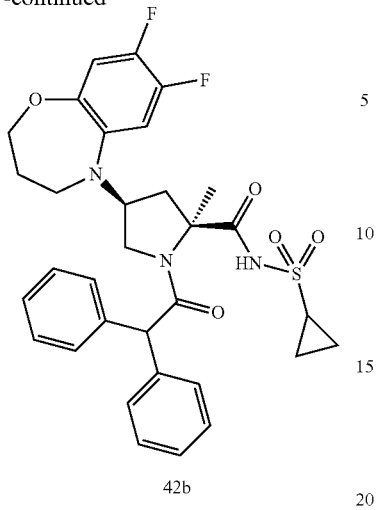

42b

CDI (110 mg, 0.67 mmol) was added to a solution of (2S)-4-(7,8-difluoro-3,4-dihydrobenzo[b][1,4]oxazepin-5(2H)-yl)-1-(2,2-diphenylacetyl)-2-methylpyrrolidine-2-carboxylic acid (32a, Example 26: 85:15 cis:trans mixture obtained prior to chiral HPLC purification) (170 mg, 0.34 mmol) in THF (1 mL) and the resulting mixture was stirred at 50° C. for 16 h. Cyclopropanesulfonamide (81 mg, 0.67 mmol) was added followed by DBU (150 µL, 1.0 mmol) and the mixture continued to stir at 50° C. for a further 16 h. The mixture was cooled to RT, diluted with Et₂O (5 mL) and washed with 1M AcOH (10 mL). The organic solution was dried over MgSO₄, filtered concentrated in vacuo. The products were purified by silica gel chromatography (12 g, 0-50% EtOAc in iso-hexane) to afford: (2S,4R)—N-(cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide 42a (17 mg, 8%) as white solid: m/z 610 [M+H]⁺ (ES⁺) at $R_t$ 8.73 min (Method 2) and (2S,4S)—N-(cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide 42b (89 mg, 39%) as a white solid: m/z 610 [M+H]⁺ (ES⁺) at $R_t$ 2.71 min (Method 1).

Example 38: Compound 43 (2S,4S)—N-(Cyclopropylsulfonyl)-1-(2,2-diphenylacetyl)-4-(2,3,4,5-tetrahydro-1H-benzo[b]azepin-1-yl)pyrrolidine-2-carboxamide

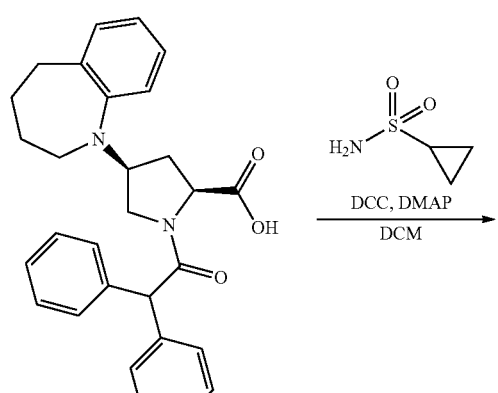

1

A mixture of (2S,4S)-1-(2,2-diphenylacetyl)-4-(2,3,4,5-tetrahydro-1H-benzo[b]azepin-1-yl)pyrrolidine-2-carboxylic acid 1 (94 mg, 0.21 mmol), cyclopropanesulfonamide (28 mg, 0.23 mmol), DMAP (8 mg, 0.06 mmol) and DCC (85 mg, 0.41 mmol) was stirred at RT for 16 h. The mixture was concentrated in vacuo onto silica gel for purification by silica gel chromatography (12 g, 0-6% (1% NH₃/MeOH) in DCM) to afford (2S,4S)—N-(cyclopropylsulfonyl)-1-(2,2-diphenylacetyl)-4-(2,3,4,5-tetrahydro-1H-benzo[b]azepin-1-yl)pyrrolidine-2-carboxamide 43 (6 mg, 5%) as a white solid: m/z 558 [M+H]⁺ (ES⁺), 556 [M−H]⁻ (ES⁻) at $R_t$ 7.95 min (Method 2).

Example 39: Compound 44 (2S,4S)—N—(N,N-Dimethylsulfamoyl)-1-(2,2-diphenylacetyl)-4-(2,3,4,5-tetrahydro-1H-benzo[b]azepin-1-yl)pyrrolidine-2-carboxamide

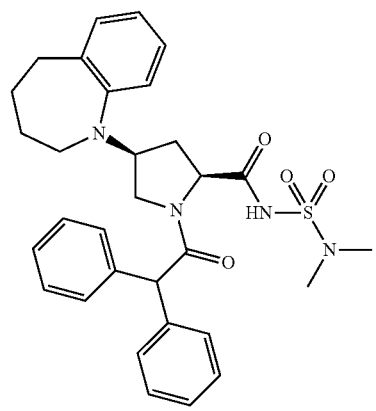 [SMILES: CN(C)S(=O)(=O)NC(=O)[C@@H]1C[C@H](N2CCCCc3ccccc32)CN1C(=O)C(c1ccccc1)c1ccccc1]

(2S,4S)—N—(N,N-Dimethylsulfamoyl)-1-(2,2-diphenylacetyl)-4-(2,3,4,5-tetrahydro-1H-benzo[b]azepin-1-yl)pyrrolidine-2-carboxamide 44 (4 mg, 3%) was prepared in essentially the same manner as for Compound 43 (Example 38) except dimethylsulfamide was used instead of cyclopropanesulfonamide: m/z 561 [M+H]⁺ (ES⁺), 559 [M−H]⁻ (ES⁻) at $R_t$ 8.20 min (Method 2).

Example 40: Compound 45 (2S,4S)-1-(2,2-Diphenylacetyl)-4-(1,2,4,5-tetrahydro-3H-benzo[d]azepin-3-yl)pyrrolidine-2-carboxylic acid

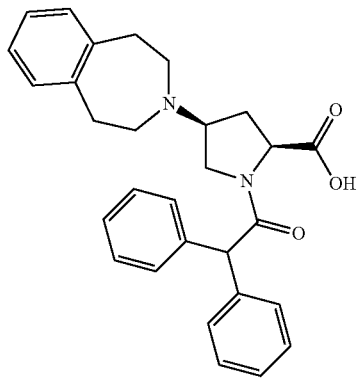 [SMILES: O=C(O)[C@@H]1C[C@H](N2CCc3ccccc3CC2)CN1C(=O)C(c1ccccc1)c1ccccc1]

(2S,4S)-1-(2,2-Diphenylacetyl)-4-(1,2,4,5-tetrahydro-3H-benzo[d]azepin-3-yl)pyrrolidine-2-carboxylic acid 45 (115 mg, 88% for final step) was prepared in essentially the same manner as for Compound 2 (Example 2) except that 2,3,4,5-tetrahydro-1H-benzo[d]azepine was used instead of 8-fluoro-2,3,4,5-tetrahydro-1H-benzo[b]azepine 2e in step 3: m/z 455 [M+H]$^+$ (ES$^+$) at R$_t$ 6.70 min (Method 2).

Example 41: Compound 10 (2S,4S)-4-(2,3-Dihydrobenzo[e][1,4]oxazepin-1(5H)-yl)-1-(2,2-diphenylacetyl)pyrrolidine-2-carboxylic acid

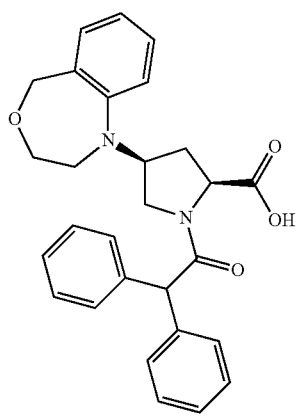 [SMILES: O=C(O)[C@@H]1C[C@H](N2CCOCc3ccccc32)CN1C(=O)C(c1ccccc1)c1ccccc1]

(2S,4S)-4-(2,3-Dihydrobenzo[e][1,4]oxazepin-1(5H)-yl)-1-(2,2-diphenylacetyl) pyrrolidine-2-carboxylic acid 10 (17 mg, 29% for final step) was prepared in essentially the same manner as for Compound 2 (Example 2) except that 1,2,3,5-tetrahydrobenzo[e][1,4]oxazepine was used instead of 8-fluoro-2,3,4,5-tetrahydro-1H-benzo[b]azepine 2e in step 3: m/z 457 [M+H]$^+$ (ES$^+$), 455 [M-H]$^-$ (ES$^-$) at R$_t$ 6.16 min (Method 2).

Example 42: Compound 17 (2S,4S)-1-(2,2-Diphenylacetyl)-4-(1-methyl-1,2,3,5-tetrahydro-4H-benzo[e][1,4]diazepin-4-yl)pyrrolidine-2-carboxylic acid

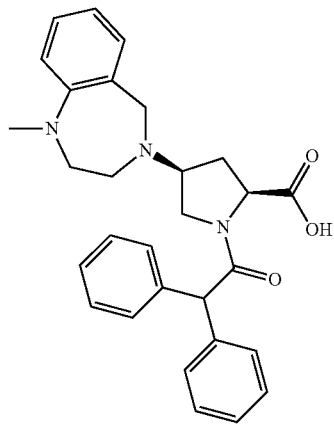 [SMILES: CN1CCN([C@H]2C[C@@H](C(=O)O)N(C(=O)C(c3ccccc3)c3ccccc3)C2)Cc2ccccc21]

(2S,4S)-1-(2,2-Diphenylacetyl)-4-(1-methyl-1,2,3,5-tetrahydro-4H-benzo[e][1,4]diazepin-4-yl)pyrrolidine-2-carboxylic acid 17 (120 mg, 99% for final step) was prepared in essentially the same manner as for Compound 2 (Example 2) except that 1-methyl-2,3,4,5-tetrahydro-1H-benzo[e][1,4]diazepine was used instead of 8-fluoro-2,3,4,5-tetrahydro-1H-benzo[b]azepine 2e in step 3: m/z 470 [M+H]$^+$ (ES$^+$), 468 [M-H]$^-$ (ES$^-$) at R$_t$ 4.52 min (Method 2).

Example 43: Compound 20 (2S,4S)-1-(2,2-Diphenylacetyl)-4-(isoindolin-2-yl)pyrrolidine-2-carboxylic acid

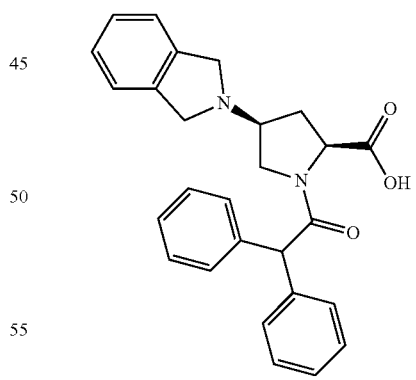

(2S,4S)-1-(2,2-Diphenylacetyl)-4-(isoindolin-2-yl)pyrrolidine-2-carboxylic acid 20 (208 mg, 80% for final step) was prepared in essentially the same manner as for Compound 2 (Example 2) except that isoindoline was used instead of 8-fluoro-2,3,4,5-tetrahydro-1H-benzo[b]azepine 2e in step 3: m/z 427 [M+H]$^+$ (ES$^+$) at R$_t$ 4.44 min (Method 2).

Example 44: Compound 19 (2S,4S)-4-(2,3-Dihydrobenzo[f][1,4]oxazepin-4(5H)-yl)-1-(2,2-diphenylacetyl)pyrrolidine-2-carboxylic acid

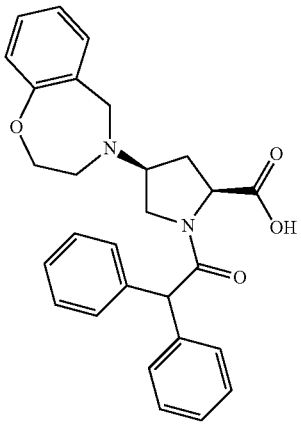 [SMILES: O=C(O)[C@@H]1C[C@H](N2CCOc3ccccc3C2)CN1C(=O)C(c1ccccc1)c1ccccc1]

(2S,4S)-4-(2,3-Dihydrobenzo[f][1,4]oxazepin-4(5H)-yl)-1-(2,2-diphenylacetyl)pyrrolidine-2-carboxylic acid 19 (184 mg, 97% for final step) was prepared in essentially the same manner as for Compound 1 (Example 1) except that 2,3,4,5-tetrahydrobenzo[f][1,4]oxazepine was used instead of 2,3,4,5-tetrahydro-1H-benzo[b]azepine in step 1): m/z 457 [M+H]$^+$ (ES$^+$), 455 [M−H]$^-$ (ES$^-$) at $R_t$ 4.93 min (Method 2).

Biological Example 1: AT$_2$ Receptor Binding

Materials

Reagents were purchased from Sigma-Aldrich, unless otherwise specified. Dialyzed fetal bovine serum (FBS) was from Life Technologies (cat. no. 10073772). Valiscreen® human angiotensin AT$_2$ receptor cell line (cat. no. ES-070-C), [$^{125}$I]CGP 42112A (cat. no. NEX324025UC) and MicroScint™ 40 (cat. no. 6013641) were purchased from PerkinElmer. CGP 42112A (cat. no. 2569) and PD 123,319 ditrifluoroacetate (cat. no. 1361) were from Tocris Biosciences. EMA401 [(S)-2-(diphenylacetyl)-1,2,3,4-tetrahydro-6-methoxy-5-(phenylmethoxy)-3-isoquinoline carboxylic acid] was obtained by synthesis using the method described in WO2012/010843.

Media and Solutions
1. Growth medium
   EX-CELL® CHO DHFR$^-$ medium
   10% FBS, dialysed
   1 mM sodium pyruvate
   2 mM L-glutamine
2. Harvesting buffer
   PBS
   2 mM EDTA
3. Suspension buffer
   50 mM Tris-HCl, pH 7.4
   10 mM EDTA
4. Resuspension buffer
   50 mM Tris-HCl, pH 7.4
   0.1 mM EDTA
   0.1% sucrose
5. Binding assay buffer
   50 mM Tris-HCl, pH 7.4
   5 mM MgCl$_2$
   1 mM EDTA
   0.1% gelatin
6. Wash buffer
   50 mM Tris-HCl, pH 7.4

Procedure for Membrane Preparation
   Valiscreen® CHO-K1 cells stably expressing the human AT$_2$ receptor were cultured in growth medium.
   Cells were seeded into T-175 flasks and grown to 70-80% confluence.
   Medium was removed from confluent flasks and cells were washed with warm PBS.
   Cells were harvested by incubating with harvesting buffer for 10 min at 37° C., and then transferred to a centrifuge tube on ice.
   Cells were centrifuged at 200 g for 5 min at 4° C.
   Cell pellets were homogenised in ice-cold suspension buffer.
   Homogenates were centrifuged at 40,000 g for 15 min at 4° C.
   Pellets were resuspended in ice-cold resuspension buffer and centrifuged at 40,000 g for 15 min at 4° C.
   Final pellets were homogenised in ice-cold resuspension buffer.
   Protein concentrations were determined by BCA assay method with BSA as standard.

Compound Preparation
   Compounds were prepared from 10 mM stock solutions in 100% DMSO. Dilutions were made using electronic multichannel pipettes. The compounds CGP 42112A (from 1 mM stock in water) and EMA401 (from 10 mM stock in 100% DMSO) were included as standards in each experiment.

Dose Plate Preparation (96-Well Plate)
   Compounds dilutions were prepared in 100% DMSO at 100× final assay concentration.
   Compounds were diluted in 100% DMSO to the appropriate maximal concentration.
   30 µL compound was added to row A.
   21.6 µL of 100% DMSO was added to rows B-H.
   Transfer 10 µL from row A into row B (half log dilution).
   Transfer 10 µL from row B into row C (half log dilution).
   Transfer 10 µL from row C into row D (half log dilution).
   Transfer 10 µL from row D into row E (half log dilution).
   Transfer 10 µL from row E into row F (half log dilution).
   Transfer 10 µL from row F into row G (half log dilution).
   Transfer 10 µL from row G into row H (half log dilution).

Working Plate Preparation (96-Well Plate)
   Compounds were diluted 10-fold in assay buffer.
   10 µL compound solution from dose plate was transferred to corresponding well of working plate.
   90 µL assay buffer was added to the wells of working plate.
   Working solutions contained 10% DMSO in assay buffer (1% DMSO final assay concentration).

Controls
   Total binding (high control) was determined in the absence of unlabelled ligand. A solution of 10% DMSO in assay buffer was prepared.
   Non-specific binding (low control) was determined in the presence of a vast excess (10 µM) of PD 123,319. 1 mM stock solution of PD 123,319 in water was diluted 10-fold with 10% DMSO in assay buffer.

Assay Plate Preparation (96-Well Plate)
   15 µL compound solution was transferred to duplicate wells of assay plate. 5 compounds were tested per plate. 15 µL control solutions were transferred to columns 1 and 12 of assay plate.

Procedures for AT$_2$ Receptor Binding Assay
- 15 μL of [$^{125}$I]CGP 42112A, at a final concentration of 0.05 nM was added to wells of assay plate.
- Membranes were dispersed using a 21 gauge needle and diluted to the appropriate protein concentration in assay buffer.
- 120 μL membrane suspension (15 μg protein/well) was added to wells of assay plate.
- Assay plates were incubated at RT for 2 h.
- Incubations were stopped by rapid filtration through Multiscreen® GF/C plates (Millipore, cat. no. MAFC-NOB50), using Multiscreeng®$_{HTS}$ vacuum manifold (Millipore, cat. no. MSVMHTS00) after pre-wetting filters with wash buffer.
- Filters were washed five times with ice-cold wash buffer.
- Filters were dried at RT.
- 50 μL MicroScint™ 40 was added to each well.
- Bound $^{125}$I was determined using MicroBeta scintillation counter in Trilux mode, for 1 min per well.

Data Analysis

Data were fitted with a 4 parameter logistic using Dotmatics Studies to determine IC$_{50}$ values. K$_i$ values were derived using the Cheng-Prussoff equation, using an estimate of [$^{125}$I]CGP 42112A K$_d$ (0.15 nM) determined in a separate saturation binding experiment. Typical assay performance parameters were SB=11; Z'=0.60. Dissociation constants (pK$_i$) for standard compounds were as follows (mean±S.E.M.): CGP 42112A 9.75±0.06; EMA401 8.71±0.06.

The results are shown in the following Table:

| Compound | Ki (nM) |
|---|---|
| 1 | 2.7 |
| 2 | 4.7 |
| 3 | 34 |
| 4 | 8.8 |
| 5 | 9.8 |
| 6 | 22.8 |
| 7 | 2.0 |
| 8 | 1.4 |
| 9 | 3.1 |
| 10 | 148 |
| 11 | 4.9 |
| 12 | 81.0 |
| 13 | 8.7 |
| 14 | 23.8 |
| 15 | 66.8 |
| 17 | 178 |
| 18 | 79.7 |
| 19 | 99 |
| 20 | 359 |
| 21 | 2.3 |
| 22 | 9.8 |
| 23 | 15.9 |
| 24 | 1.4 |
| 25 | 1.6 |
| 26 | 4.1 |
| 27 | 2.8 |
| 28 | 33.0 |
| 29 | 224.7 |
| 30 | 3.3 |
| 31 | 11.8 |
| 32 | 3.7 |
| 33 | 7.0 |
| 34 | 10.0 |
| 35 | 36.2 |
| 36 | 2.6 |
| 37 | 4.1 |
| 38 | 6.0 |
| 39 | 10.2 |
| 40 | 9.3 |
| 41 | 15.1 |
| 42a | 5.0 |
| 42b | 11.0 |
| 43 | 8.6 |
| 44 | 16.9 |
| 45 | 28.2 |

Biological Example 2: Human Hepatocyte Stability Assay Protocol

A human hepatocyte (cryopreserved) incubation mixture containing, 0.5 million cells/mL and phosphate buffered saline (pH 7.4) was pre-incubated at 37° C. and the reaction then initiated by the addition of 1 μM test compound. The incubations were performed in duplicate. The final organic concentration was 1% (consisting of 90% acetonitrile and 10% DMSO). Positive control markers for Phase I and II metabolism were included. Samples were removed at 6 time-points over 60 min and each reaction terminated by the addition of methanol containing internal standard. After vortexing and centrifugation, the resultant supernatant was analysed by UPLC-MS.

Intrinsic clearance is calculated from the resulting concentration-time profile. For substrate concentrations significantly below K$_m$, metabolism follows first order kinetics, which means that the compound concentration-time profile can be described by:

$$C(t) = C(0) \times e^{-kt}$$

Where C(t) is the compound concentration at time t, C(0) is the starting concentration and k is the elimination rate constant.

The ln(concentration) vs time profile can be mathematically described by:

$$\ln C(t) = \ln C(0) - kt$$

Where k represents the slope of the regression line. Solving for k results in:

$$k = \frac{\ln C(0) - \ln C(t)}{t} \, \text{min}^{-1}$$

Once k is known, half-life (t½) can be calculated using:

$$t_{1/2} = \frac{\ln 2}{k} \, \text{min}$$

Furthermore, CLint can be calculated by introducing the cell density ([cell]) in 10$^6$/ml:

$$CL_{int} = \frac{\ln 2}{t_n \times [\text{cell}]} = \frac{k}{[\text{cell}]} \mu l \times \text{min}^{-1} \, (10^{th} \text{ cells})^{-1}$$

The results for test compounds are shown in the table below.

| Compound | Clint (μL/min/million cells) | T½ (min) |
|---|---|---|
| 36 | <3 | >460 |
| 32 | <3 | >460 |

REFERENCES

Chakrabarty et al., 2008, Estrogen elicits dorsal root ganglion axon sprouting via a rennin-angiotensin system. *Endocrinology*, 149(7):3452-3460.

Clere et al., 2010, Deficiency or blockade of angiotensin II type 2 receptor delays tumorigenesis by inhibiting malignant cell proliferation and angiogenesis. *Int. J. Cancer*, 127: 2279-2291.

Izu et al., 2009, Angiotensin II Type 2 receptor blockade increases bone mass. *J. Biol. Chem.*, 284(8):4857-4864.

Reger et al., 2010, Heterocycle-substituted proline dipeptides as potent VLA-4 antagonists. *Biorg. & Med. Chem. Lett.*, 20:1173-1176.

Steckelings et al., 2005, The $AT_2$ receptor—A matter of love and hate. *Peptides*, 26:1401-1409.

Wallinder et al., 2008, Selective angiotensin II $AT_2$ receptor agonists: Benzamide structure-activity relationships. *Bioorganic & Medicinal Chemistry*, 16:6841-6849.

Wan et al., 2004, Design, Synthesis and biological evaluation of the first selective nonpeptide $AT_2$ receptor agonist. *J. Med. Chem.*, 47:5995-6008.

Wexler et al., 1996, Nonpeptide angiotensin II receptor antagonists: The next generation in antihypertensive therapy. *J. Med. Chem.*, 39(3):325-656.

The claims defining the invention are as follows:

1. A compound of formula (I):

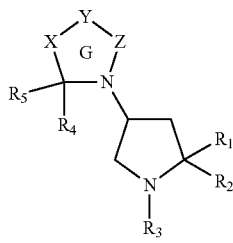

wherein Ring G is a 5 to 8 membered ring and

X is absent or is selected from —$(CR_6R_7)_n$—, —W—, —$(CR_6R_7)_m$—W—, —W—$(CR_6R_7)_m$— and —$(CR_6R_7)_p$—W—$(CR_6R_7)_p$—;

Y is —$CR_8CR_9$— wherein $R_8$ and $R_9$ together with the carbon atoms to which they are attached form an optionally substituted aromatic or heteroaromatic ring or optionally substituted aromatic or heteroaromatic ring system;

Z is absent or is selected from —$CR_4R_5$—, —$CR_6R_7CR_4R_5$—, —W—$CR_4R_5$—;

W is selected from —O—, —S—, —S(O)—, —$S(O)_2$—, —C(O)—, —$NR_{10}$—, —$C(O)N(R_{11})$—, —$N(R_{11})C(O)$—, —C(O)O—, —OC(O)—, —$S(O)_2N(R_{11})$—, —$N(R_{11})S(O)_2$—, —$N(R_{11})C(O)N(R_{11})$— and —$N(R_{11})S(O)_2N(R_{11})$—;

$R_1$ is selected from —$CO_2H$, —$CH_2CO_2H$, —C(O)C(O)OH, —$CH_2OH$, —$C(O)NH_2$, —CN, —$CH_2C(O)NH_2$, —$CH_2CN$, a carboxylic acid bioisostere and —$CH_2$carboxylic acid bioisostere;

$R_2$ is selected from hydrogen, alkyl, alkenyl, alkynyl, —$C_{1-6}$alkyleneR$_{12}$, —$C_{2-6}$alkenyleneR$_{12}$ and —$C_{2-6}$alkynyleneR$_{12}$;

$R_3$ is selected from —C(O)CH(aryl)(aryl) and —C(O)N(aryl)(aryl);

Each $R_4$ and $R_5$ are independently selected from hydrogen —$C_{1-6}$alkyl, —$C_{2-6}$alkenyl, —$C_{2-6}$alkynyl, halo, —OH, —$OC_{1-6}$alkyl, —$OC_{2-6}$alkenyl, —$OC_{2-6}$alkynyl, —$CF_3$, —$CHF_2$, —$CH_2F$, —$OCF_3$, —$OCHF_2$, —$OCH_2F$, —CN, —$NO_2$, —$NH_2$, —$NH(C_{1-6}$alkyl), —$N(C_{1-6}$alkyl)$_2$, —NH(aryl), —$N(C_{1-6}$alkyl)(phenyl), —$N(phenyl)_2$, —$CO_2H$, —$CO_2C_{1-6}$alkyl, —$CO_2C_{6}$alkenyl, —$CO_2$phenyl, —$C(O)NH_2$, —$C(O)NHC_{1-6}$alkyl, —$C(O)N(C_{1-6}$alkyl)$_2$, —$C(O)C_{1-6}$alkyl, —$C(O)C_{2-6}$alkenyl, —$C(O)C_{2-6}$alkynyl, —$S(O)_2C_{1-6}$alkyl, —$S(O)_2$aryl, —$S(O)_2NH_2$, —$S(O)NH(C_{1-6}$alkyl) and —$S(O)_2N(C_{1-6}$alkyl)$_2$;

$R_6$ and $R_7$ are independently selected from hydrogen, alkyl, alkenyl, alkynyl, —$OR_{13}$, —$SR_{13}$, halo, —CN, —$NO_2$, —$N(R_{13})_2$, —$CO_2R_{13}$, —$C(O)R_{13}$, —$C(O)N(R_{13})_2$, —$S(O)_2R_{13}$, $S(O)_2N(R_{13})_2$, —$C(R_{14})_3$, —$OC(R_{14})_3$, cycloalkyl, cycloalkenyl, aryl, heterocyclyl and heteroaryl, or $R_6$ and $R_7$ taken together form a carbonyl group;

$R_{10}$ is selected from hydrogen, $C_{1-6}$alkyl, —$C(O)C_{1-6}$alkyl, —$C(O)C_{2-6}$alkenyl, —$C(O)C_{2-6}$alkynyl, —$CO_2H$, —$CO_2C_{1-6}$alkyl, —$CO_2C_{2-6}$alkynyl, —$CO_2C_{2-6}$alkenyl, —$C(O)NH_2$, —$C(O)NH(C_{1-6}$alkyl), —$C(O)NH(C_{2-6}$alkenyl), —$C(O)NH(C_{2-6}$alkynyl), —$C(O)N(C_{1-6}$alkyl)$_2$, —$SO_2C_{1-6}$alkyl, —$SO_2C_{2-6}$alkenyl, —$SO_2C_{2-6}$alkynyl, —$SO_2NH_2$, —$SO_2NH(C_{1-6}$alkyl), —$SO_2NH(C_{2-6}$alkenyl), —$SO_2NH(C_{2-6}$alkynyl), —$SO_2N(C_{1-6}$alkyl)$_2$, —$SO_2CF_3$, —$SO_2NHC(O)NH_2$, —$SO_2NHC(O)NH(C_{1-6}$alkyl) and —$SO_2NHC(O)N(C_{1-6}$alkyl)$_2$;

$R_{11}$ is selected from hydrogen and $C_{1-3}$alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;

m is selected from an integer from 1 to 3;

p is selected from an integer of 1 or 2;

wherein each alkyl, alkenyl, alkynyl, cycloalkyl, cycloalkenyl, aryl, heterocyclyl and heteroaryl may be optionally substituted; or a pharmaceutically acceptable salt thereof.

2. A compound according to claim 1 wherein X is absent or is selected from —$(CR_6R_7)_n$—, —W—, —$(CR_6R_7)_m$—W— and —$(CR_6R_7)_p$—W—$(CR_6R_7)_p$—.

3. A compound according to claim 1 wherein Y is selected from —$CR_8CR_9$— wherein $R_8$ and $R_9$ together with the carbon atoms to which they are attached form a five or six membered monocyclic or eight to ten membered bicyclic aromatic or heteroaromatic ring selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl[b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, each of which may be optionally substituted.

4. A compound according to claim 1 wherein Z is absent or is selected from —$CR_4R_5$— and —$CR_6R_7CR_4R_5$—.

5. A compound according to claim 4 wherein W is selected from —O—, —C(O)—, —S(O)₂—, —N(R₁₀)—, —C(O)N(R₁₁)—, —N(R₁₁)C(O)—, —S(O)₂N(R₁₁)— and —N(R₁₁)S(O)₂—.

6. A compound according to claim 5 wherein W is —O— or —NR₁₀—.

7. A compound according to claim 1 wherein R₁ is selected from —CO₂H, —CH₂CO₂H, —C(O)C(O)OH, —C(O)NH₂, —CN, —C(O)NHSO₂C₁₋₆alkyl, —C(O)NHSO₂C₃₋₈cycloalkyl, —C(O)NHSO₂phenyl, —C(O)NHSO₂N(C₁₋₆ alkyl)₂, —C(O)NHSO₂N(C₃₋₈cycloalkyl)₂, —C(O)NHSO₂N(C₁₋₆alkyl)(C₃₋₈cycloalkyl), —C(O)NHSO₂CF₃, tetrazole and tetrazolate.

8. A compound according to claim 1 wherein R₂ is selected from hydrogen, —C₁₋₆alkyl, —C₁₋₄alkyleneR₁₂, —C₂₋₄alkenyleneR₁₂ and —C₂₋₄alkynyleneR₁₂.

9. A compound according to claim 1 wherein R₃ is selected from —C(O)CH(phenyl)(phenyl) and —C(O)N(phenyl)(phenyl).

10. A compound according to claim 1 wherein each of R₆ and R₇ are independently selected from hydrogen —C₁₋₆alkyl, —C₂₋₆alkenyl, —C₂₋₆alkynyl, halo, —OH, —OC₁₋₆alkyl, —OC₂₋₆alkenyl, —OC₂₋₆alkynyl, —CN, —NO₂, —NH₂, —NH(C₁₋₆ alkyl), —N(C₁₋₆alkyl)₂, —NH(aryl), —N(C₁₋₆alkyl)(phenyl), —N(phenyl)₂, —CO₂H, —CO₂C₁₋₆alkyl, —CO₂C₂₋₆alkenyl, —CF₃, —CHF₂, —CH₂F, —OCF₃, —OCHF₂, —OCH₂F, —CO₂phenyl, —C(O)NH₂, —C(O)NHC₁₋₆alkyl, —C(O)N(C₁₋₆alkyl)₂, —C(O)C₁₋₆alkyl, —C(O)C₂₋₆alkenyl, —C(O)C₂₋₆alkynyl, —S(O)₂C₁₋₆alkyl, —S(O)₂aryl, —S(O)₂NH₂, —S(O)₂NH(C₁₋₆alkyl) and —S(O)₂N(C₁₋₆alkyl)₂.

11. A compound according to claim 1 wherein R₁₂ is selected from cycloalkyl and aryl.

12. A compound according to claim 1 wherein each R₁₃ is independently selected from hydrogen, C₁₋₆alkyl, C₃₋₆cycloalkyl, C₅₋₆ cycloalkenyl and phenyl.

13. A compound according to claim 1 wherein n is 2 or 3.

14. A compound according to claim 1 wherein m is 1 or 2.

15. A compound according to claim 1 which is a compound of formula (II):

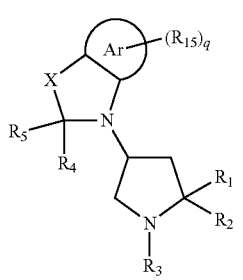

(II)

wherein
X is selected from —(CR₆R₇)ₙ—, —W—, —(CR₆R₇)ₘ—W—, —W—(CR₆R₇)ₘ— and —(CR₆R₇)ₚ—W—(CR₆R₇)ₚ—;
Ar is an aromatic or heteroaromatic ring or ring system;
R₁ is selected from —CO₂H, —CH₂CO₂H, —C(O)C(O)OH, —CH₂OH, —C(O)NH₂, —CN, —CH₂C(O)NH₂, —CH₂CN, a carboxylic acid bioisostere and —CH₂carboxylic acid bioisostere;
R₂ is selected from hydrogen, alkyl, alkenyl, alkynyl, —C₁₋₆alkyleneR₁₂, —C₂₋₆alkenyleneR₁₂ and —C₂₋₆alkynyleneR₁₂;

R₃ is selected from —C(O)CH(aryl)(aryl) and —C(O)N(aryl)(aryl);
Each R₄ and R₅ are independently selected from hydrogen, —C₁₋₆alkyl, —C₂₋₆alkenyl, —C₂₋₆alkynyl, halo, —OH, —OC₁₋₆alkyl, —OC₂₋₆alkenyl, —OC₂₋₆alkynyl, —CF₃, —CHF₂, —CH₂F, —OCF₃, —OCHF₂, —OCH₂F, —CN, —NO₂, —NH₂, —NH(C₁₋₆alkyl), —N(C₁₋₆alkyl)₂, —NH(aryl), —N(C₁₋₆alkyl)(phenyl), —N(phenyl)₂, —CO₂H, —CO₂C₁₋₆alkyl, —CO₂C₂₋₆alkenyl, —CO₂phenyl, —C(O)NH₂, —C(O)NHC₁₋₆alkyl, —C(O)N(C₁₋₆alkyl)₂, —C(O)C₁₋₆alkyl, —C(O)C₂₋₆alkenyl, —C(O)C₂₋₆alkynyl, —S(O)₂C₁₋₆alkyl, —S(O)₂aryl, —S(O)₂NH₂, —S(O)₂NH(C₁₋₆alkyl) and —S(O)₂N(C₁₋₆alkyl)₂;
R₆ and R₇ are independently selected from hydrogen, alkyl, alkenyl, alkynyl, —OR₁₃, —SR₁₃, halo, —CN, —NO₂, —N(R₁₃)₂, —CO₂R₁₃, —C(O)R₁₃, —C(O)N(R₁₃)₂, —S(O)₂R₁₃, S(O)₂N(R₁₃)₂, —C(R₁₄)₃, —OC(R₁₄)₃, cycloalkyl, cycloalkenyl, aryl, heterocyclyl and heteroaryl, or R₆ and R₇ taken together form a carbonyl group;
W is selected from —O—, —S—, —S(O)—, —S(O)₂—, —C(O)—, —NR₁₀—, —C(O)N(R₁₁)—, —N(R₁₁)C(O)—, —C(O)O—, —OC(O)—, —S(O)₂N(R₁₁)—, —N(R₁₁)S(O)₂—, —N(R₁₁)C(O)N(R₁₁)— and —N(R₁₁)S(O)₂N(R₁₁)—;
R₁₀ is selected from hydrogen, C₁₋₆alkyl, —C(O)C₁₋₆alkyl, —C(O)C₂₋₆alkynyl, —CO₂H, —CO₂C₁₋₆alkyl, —CO₂C₂₋₆alkenyl, —CO₂C₂₋₆alkynyl, —C(O)NH₂, —C(O)NH(C₁₋₆alkyl), —C(O)NH(C₂₋₆ alkenyl), —C(O)NH(C₂₋₆alkynyl), —C(O)N(C₁₋₆alkyl)₂, —SO₂C₁₋₆alkyl, —SO₂C₂₋₆alkenyl, —SO₂C₂₋₆alkynyl, —SO₂NH₂, —SO₂NH(C₁₋₆alkyl), —SO₂NH(C₂₋₆alkenyl), —SO₂NH(C₂₋₆alkynyl), —SO₂N(C₁₋₆alkyl)₂, —SO₂CF₃, —SO₂NHC(O)NH₂, —SO₂NHC(O)NH(C₁₋₆alkyl) and —SO₂NHC(O)N(C₁₋₆alkyl)₂;
R₁₁ is selected from hydrogen and C₁₋₃alkyl;
R₁₂ is selected from cycloalkyl, cycloalkenyl, aryl, heterocyclyl and heteroaryl;
Each R₁₃ is independently selected from hydrogen, alkyl, alkenyl, alkynyl, cycloalkyl, cycloalkenyl, aryl, heterocyclyl and heteroaryl;
Each R₁₄ is independently selected from hydrogen and halo;
Each R₁₅ is independently selected from —C₁₋₆alkyl, —C₂₋₆alkenyl, —C₂₋₆alkynyl, —OR₁₃, —SR₁₃, halo, —CN, —NO₂, —N(R₁₃)₂, —CO₂R₁₃, —CON(R₁₃)₂, —C(O)R₁₃, —S(O)₂R₁₃, —S(O)₂N(R₁₃)₂, —C(R₁₄)₃, —OC(R₁₄)₃, cycloalkyl, cycloalkenyl, aryl, heterocyclyl and heteroaryl;
m is selected from an integer from 1 to 3;
n is selected from an integer from 1 to 4;
p is selected from an integer of 1 or 2; and
q is 0 or an integer of 1 to 4;
wherein each alkyl, alkenyl, alkynyl, cycloalkyl, cycloalkenyl, aryl, heterocyclyl and heteroaryl may be optionally substituted; or
a pharmaceutically acceptable salt thereof.

16. A pharmaceutical composition comprising a compound of formula (I) according to claim 1 or a pharmaceutically acceptable salt thereof and a pharmaceutically acceptable carrier.

17. A method of treating or preventing neuropathic pain or inflammatory pain in a subject comprising administering a compound of formula (I) according to claim 1 or a pharmaceutically acceptable salt thereof.

18. A method of treating or preventing a condition characterized by neuronal hypersensitivity, impaired nerve conduction velocity, a cell proliferative disorder, a disorder associated with an imbalance between bone resorption and bone formation, or a disorder associated with aberrant nerve regeneration, in a subject comprising administering a compound of formula (I) according to claim 1 or a pharmaceutically acceptable salt thereof.

19. A method of producing analgesia in a subject comprising administering a compound of formula (I) according to claim 1 or a pharmaceutically acceptable salt thereof.

20. A compound according to claim 1 selected from the group consisting of:
- (2S,4S)-1-(2,2-Diphenylacetyl)-4-(2,3,4,5-tetrahydro-1H-benzo[b]azepin-1-yl)pyrrolidine-2-carboxylic acid;
- (2S,4S)-1-(2,2-Diphenylacetyl)-4-(8-fluoro-2,3,4,5-tetrahydro-1H-benzo[b]azepin-1-yl)pyrrolidine-2-carboxylic acid;
- (2S,4S)-1-(2,2-Diphenylacetyl)-4-(7-fluoro-3,4-dihydrobenzo[b][1,4]oxazepin-5(2H)-yl)pyrrolidine-2-carboxylic acid;
- (2S,4S)-1-(2,2-diphenylacetyl)-4-(8-fluoro-3,4-dihydrobenzo[b][1,4]oxazepin-5(2H)-yl)pyrrolidine-2-carboxylic acid;
- (2S,4S)-4-(3,4-dihydrobenzo[b][1,4]oxazepin-5(2H)-yl)-1-(2,2-diphenylacetyl)pyrrolidine-2-carboxylic acid;
- (2S,4S)-4-(7,8-difluoro-3,4-dihydrobenzo[b][1,4]oxazepin-5(2H)-yl)-1-(2,2-diphenylacetyl)pyrrolidine-2-carboxylic acid;
- (2S,4R)-1-(2,2-diphenylacetyl)-4-(2,3,4,5-tetrahydro-1H-benzo[b]azepin-1-yl) pyrrolidine-2-carboxylic acid;
- (2S,4R)-4-(7,8-Difluoro-3,4-dihydrobenzo[b][1,4]oxazepin-5(2H)-yl)-1-(2,2-diphenylacetyl)pyrrolidine-2-carboxylic acid;
- (2S,4R)-1-(2,2-Diphenylacetyl)-4-(7-fluoro-3,4-dihydrobenzo[b][1,4]oxazepin-5(2H)-yl)pyrrolidine-2-carboxylic acid;
- (2S,4R)-4-(3,4-Dihydrobenzo[b][1,4]oxazepin-5(2H)-yl)-1-(2,2-diphenylacetyl)pyrrolidine-2-carboxylic acid;
- (2S,4S)-4-(7,8-Difluoro-2,3,4,5-tetrahydro-1H-benzo[b]azepin-1-yl)-1-(2,2-diphenylacetyl)pyrrolidine-2-carboxylic acid;
- (2S,4S)-1-(2,2-Diphenylacetyl)-4-(5,6,7,8-tetrahydro-4H-thieno[3,2-b]azepin-4-yl)pyrrolidine-2-carboxylic acid;
- (2S,4S)-1-(2,2-Diphenylacetyl)-4-(3,4,5,6-tetrahydrobenzo[b]azocin-1 (2H)-yl)pyrrolidine-2-carboxylic acid;
- (2S,4S)-1-(2,2-Diphenylacetyl)-4-(7-methoxy-2,3,4,5-tetrahydro-1H-benzo[b]azepin-1-yl)pyrrolidine-2-carboxylic acid;
- (2S,4S)-1-(2,2-Diphenylacetyl)-4-(7-fluoro-2,3,4,5-tetrahydro-1H-benzo[b]azepin-1-yl)pyrrolidine-2-carboxylic acid;
- (2S,4S)-4-(7-Chloro-2,3,4,5-tetrahydro-1H-benzo[b]azepin-1-yl)-1-(2,2-diphenylacetyl)pyrrolidine-2-carboxylic acid;
- (2S,4S)-1-(2,2-Diphenylacetyl)-4-(1,3,4,5-tetrahydro-2H-benzo[c]azepin-2-yl)pyrrolidine-2-carboxylic acid;
- (2S,4R)-1-(2,2-Diphenylacetyl)-4-(2,3,4,5-tetrahydro-1H-pyrido[3,4-b]azepin-1-yl)pyrrolidine-2-carboxylic acid;
- (2S,4S)-1-(2,2-Diphenylacetyl)-4-(8-methyl-2,3,4,5-tetrahydro-1H-benzo[b]azepin-1-yl)pyrrolidine-2-carboxylic acid;
- (2S,4R)-1-(2,2-Diphenylacetyl)-4-(8-methyl-2,3,4,5-tetrahydro-1H-benzo[b]azepin-1-yl)pyrrolidine-2-carboxylic acid;
- (2S,4S)-1-(2,2-Diphenylacetyl)-4-(indolin-1-yl)pyrrolidine-2-carboxylic acid;
- (2S,4S)-1-(2,2-Diphenylacetyl)-4-(5,6,7,8-tetrahydro-9H-pyrido[2,3-b]azepin-9-yl)pyrrolidine-2-carboxylic acid;
- (2S,4S)-4-(3,4-Dihydroquinolin-1(2H)-yl)-1-(2,2-diphenylacetyl)pyrrolidine-2-carboxylic acid;
- (2S,4S)-1-(2,2-Diphenylacetyl)-2-methyl-4-(2,3,4,5-tetrahydro-1H-benzo[b]azepin-1-yl)pyrrolidine-2-carboxylic acid;
- (2S,4S)-4-(7,8-Difluoro-2,3,4,5-tetrahydro-1H-benzo[b]azepin-1-yl)-1-(2,2-diphenylacetyl)-2-methylpyrrolidine-2-carboxylic acid;
- (2S,4S)-4-(7,8-Difluoro-3,4-dihydrobenzo[b][1,4]oxazepin-5(2H)-yl)-1-(2,2-diphenylacetyl)-2-methylpyrrolidine-2-carboxylic acid;
- (2S,4S)-1-(2,2-Diphenylacetyl)-4-(8-fluoro-3,4-dihydrobenzo[b][1,4]oxazepin-5(2H)-yl)-2-methylpyrrolidine-2-carboxylic acid;
- (2S,4S)-4-(1,1-Dioxido-3,4-dihydrobenzo[b][1,4]thiazepin-5(2H)-yl)-1-(2,2-diphenylacetyl)pyrrolidine-2-carboxylic acid;
- (2S,4S)-1-(2,2-Diphenylacetyl)-4-(2,3,4,5-tetrahydro-1H-benzo[b]azepin-1-yl)pyrrolidine-2-carboxamide;
- 2,2-Diphenyl-1-((2S,4S)-4-(2,3,4,5-tetrahydro-1H-benzo[b]azepin-1-yl)-2-(2H-tetrazol-5-yl)pyrrolidin-1-yl)ethan-1-one;
- (2S,4S)—N-(Cyclopropylsulfonyl)-4-(7,8-difluoro-3,4-dihydrobenzo[b][1,4]oxazepin-5(2H)-yl)-1-(2,2-diphenylacetyl)pyrrolidine-2-carboxamide;
- (2S,4S)—N-(Cyclopropylsulfonyl)-1-(2,2-diphenylacetyl)-4-(7-fluoro-3,4-dihydrobenzo[b][1,4]oxazepin-5(2H)-yl)pyrrolidine-2-carboxamide;
- (2S,4S)—N-(Cyclopropylsulfonyl)-1-(2,2-diphenylacetyl)-4-(8-fluoro-3,4-dihydrobenzo[b][1,4]oxazepin-5(2H)-yl)pyrrolidine-2-carboxamide;
- (2S,4S)-4-(7,8-Difluoro-3,4-dihydrobenzo[b][1,4]oxazepin-5(2H)-yl)-N—(N, N-dimethylsulfamoyl)-1-(2,2-diphenylacetyl)pyrrolidine-2-carboxamide;
- (2S,4S)-4-(7,8-Difluoro-2,3,4,5-tetrahydro-1H-benzo[b]azepin-1-yl)-N—(N, N-dimethylsulfamoyl)-1-(2,2-diphenylacetyl)pyrrolidine-2-carboxamide;
- (2S,4S)—N-(Cyclopropylsulfonyl)-4-(7,8-difluoro-2,3,4,5-tetrahydro-1H-benzo[b]azepin-1-yl)-1-(2,2-diphenylacetyl)pyrrolidine-2-carboxamide;
- (2S,4S)—N-(Cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide;
- (2S,4R)—N-(cyclopropylsulfonyl)-4-(7,8-difluoro-3,4-dihydrobenzo[b][1,4]oxazepin-5(2H)-yl)-1-(2,2-diphenylacetyl)-2-methylpyrrolidine-2-carboxamide;
- (2S,4S)—N-(Cyclopropylsulfonyl)-1-(2,2-diphenylacetyl)-4-(2,3,4,5-tetrahydro-1H-benzo[b]azepin-1-yl)pyrrolidine-2-carboxamide;
- (2S,4S)—N—(N, N-Dimethylsulfamoyl)-1-(2,2-diphenylacetyl)-4-(2,3,4,5-tetrahydro-1H-benzo[b]azepin-1-yl)pyrrolidine-2-carboxamide;
- (2S,4S)-1-(2,2-Diphenylacetyl)-4-(1,2,4,5-tetrahydro-3H-benzo[d]azepin-3-yl)pyrrolidine-2-carboxylic acid;
- (2S,4S)-4-(2,3-Dihydrobenzo[e][1,4]oxazepin-1(5H)-yl)-1-(2,2-diphenylacetyl)pyrrolidine-2-carboxylic acid;
- (2S,4S)-1-(2,2-Diphenylacetyl)-4-(1-methyl-1,2,3,5-tetrahydro-4H-benzo[e][1,4]diazepin-4-yl)pyrrolidine-2-carboxylic acid;

(2S,4S)-1-(2,2-Diphenylacetyl)-4-(isoindolin-2-yl)pyrrolidine-2-carboxylic acid; and (2S,4S)-4-(2,3-Dihydrobenzo[f][1,4]oxazepin-4(5H)-yl)-1-(2,2-diphenylacetyl)pyrrolidine-2-carboxylic acid; or a pharmaceutically acceptable salt thereof.

21. A pharmaceutical composition comprising a compound of formula (I) according to claim 20 or a pharmaceutically acceptable salt thereof and a pharmaceutically acceptable carrier.

* * * * *